United States Patent [19]

Schatz et al.

[11] Patent Number: 5,733,731
[45] Date of Patent: *Mar. 31, 1998

[54] PEPTIDE LIBRARY AND SCREENING METHOD

[75] Inventors: Peter J. Schatz, Mountain View; Millard G. Cull, Oakland; Jeff F. Miller, Los Angeles; Willem Peter Christiaan Stemmer, Los Gatos; Christian M. Gates, Morgan Hill, all of Calif.

[73] Assignee: Affymax Technologies N.V., Greenford, England

[ * ] Notice: The term of this patent shall not extend beyond the expiration date of Pat. No. 5,498,530 and 5,338,665.

[21] Appl. No.: 548,540

[22] Filed: Oct. 26, 1995

(Under 37 CFR 1.47)

Related U.S. Application Data

[63] Continuation-in-part of Ser. No. 290,641, Aug. 15, 1994, Pat. No. 5,498,530, which is a continuation of Ser. No. 963,321, Oct. 15, 1992, Pat. No. 5,338,665, which is a continuation-in-part of Ser. No. 778,233, Oct. 16, 1991, Pat. No. 5,270,170.

[51] Int. Cl.$^6$ .............................. C12Q 1/68; C12N 1/21; C12N 15/72

[52] U.S. Cl. .................. 435/6; 435/172.3; 435/252.33; 435/320.1; 530/413; 536/23.4

[58] Field of Search ........................ 435/172.3, 6, 320.1, 435/252.3, 252.33; 530/413; 536/23.4

[56] References Cited

U.S. PATENT DOCUMENTS

| | | | |
|---|---|---|---|
| 4,359,535 | 11/1982 | Pieczenik | 435/320.1 |
| 4,593,002 | 6/1986 | Dulbecco | 435/172.3 |
| 4,643,969 | 2/1987 | Inouye et al. | 435/69.1 |
| 4,833,092 | 5/1989 | Geysen | 436/501 |
| 4,910,140 | 3/1990 | Dower | 435/172.3 |
| 5,028,530 | 7/1991 | Lai et al. | 435/69.1 |
| 5,143,854 | 9/1992 | Pirrung et al. | 436/518 |
| 5,223,409 | 6/1993 | Ladner | 435/69.7 |
| 5,270,170 | 12/1993 | Schatz et al. | 435/7.37 |
| 5,338,665 | 8/1994 | Schatz et al. | 435/6 |
| 5,498,530 | 3/1996 | Schatz et al. | 435/69.1 |

FOREIGN PATENT DOCUMENTS

| | | |
|---|---|---|
| 469897 | 2/1992 | European Pat. Off. . |
| 2183661 | 6/1987 | United Kingdom . |
| 87/01374 | 12/1987 | WIPO . |
| 88/05085 | 7/1988 | WIPO . |
| 88/06630 | 9/1988 | WIPO . |
| 89/06694 | 7/1989 | WIPO . |
| 90/02809 | 3/1990 | WIPO . |
| 90/05144 | 5/1990 | WIPO . |
| 90/14424 | 11/1990 | WIPO . |
| 90/14430 | 11/1990 | WIPO . |
| 90/14443 | 11/1990 | WIPO . |
| 91/10737 | 7/1991 | WIPO . |
| 91/18980 | 12/1991 | WIPO . |
| 92/01047 | 1/1992 | WIPO . |
| 92/06204 | 4/1992 | WIPO . |
| 92/07077 | 4/1992 | WIPO . |
| 92/09690 | 6/1992 | WIPO . |
| 92/15677 | 9/1992 | WIPO . |
| 92/15679 | 9/1992 | WIPO . |
| 92/15702 | 9/1992 | WIPO . |
| 92/18619 | 10/1992 | WIPO . |

OTHER PUBLICATIONS

Aruffo et al., "Molecular cloning of a CD28 cDNA by a high-efficiency cos cell expression system", *Proc. Natl. Acad. Sci. USA*, 84:8573–8577 (1987).

Barbas III et al., "Assembly of combinatorial antibody libraries on phage surfaces; the gene III site", *Proc. Natl. Acad. Sci. USA*, 88:7978–7982 (1991).

Barrett and Goldstein, "A Monoclonal Antibody Specific for a Dynorphin Precursor", *Neuropeptides*, 6:113–120 (1985).

Barrett et al., "Selective enrichment and characterization of high affinity ligands from collections of random peptides on filamentous phage", *Analytical Biochemistry*, 204:357–364 (1992).

Bass et al., "Hormone phage: an enrichment method for variant proteins with altered binding properties", *Proteins: Structure, Functions and Genetics*, 8:309–314 (1990).

Besse et al., "Synthetic lac operator mediates repression through lac repressor when introduced upstream and downstream from lac promoter", *EMBO J.*, 5(6):1377–1381 (1986).

Better et al., "*Escherichia coli* selection of an active chimeric antibody fragment," *Science*, 240:1041–1043 (1988).

Boeke et al., "A prokaryotic membrane anchor sequence: carboxyl terminus of bacteriophage f1 gene iii protein retains it in the membrane", *Proc. Natl. Acad. Sci. USA*, 79:5200–5204 (1982).

Böttger, "High–efficiency generation of plasmid cDNA libraries using electro–transformation", *BioTechniques*, 6:878–880 (1988).

Bowie and Sauer, "Identification of C–terminal extension that Protects Proteins from Intracellular Proteolysis", *J. Biol. Chem.*, 264(13):7596–7602 (1989).

Brake et al., "Beta–Galactosidase chimeras: Primary structure of a lac repressor–b–galactosidase protein", *Proc. Natl. Acad. Sci. USA*, 75(10):4824–4827 (1978).

Cwirla et al., "Peptides on phage: A vast library of peptides for identifying ligands", *Proc. Natl. Acad. Sci. USA*, 87:6378–6382 (1990).

(List continued on next page.)

*Primary Examiner*—James Ketter
*Attorney, Agent, or Firm*—Joe Liebeschuetz; Lauren L. Stevens

[57] ABSTRACT

A random peptide library constructed by transforming host cells with a collection of recombinant vectors that encode a fusion protein comprised of a DNA binding protein and a random peptide and also encode a binding site for the DNA binding protein can be used to screen for novel ligands. The screening method results in the formation of a complex comprising the fusion protein bound to a receptor through the random peptide ligand and to the recombinant DNA vector through the DNA binding protein.

27 Claims, 11 Drawing Sheets

OTHER PUBLICATIONS

Daly and Matthews, "Characterization and Modification of a Monomeric Mutant of the Lactose Repressor Protein", *Biochemistry*, 25:5474–5478 (1986).

de la Cruz et al., "Immunogenicity and epitope mapping of foreign sequences via genetically engineered filamentous phage", *J. Biol. Chem.*, 263(9):4318–4322 (1988).

Devlin et al., "Random Peptide Libraries: A Source of Specific Protein Binding Molecules", *Science*, 249:404–406 (1990).

Dower et al., "High efficiency transformation of *E. coli* by high voltage electroporation", *Nucleic Acids Res.*, 16(13):6217–6145 (1988).

Dower et al., "Creating vast peptide expression libraries: Electroporation as a tool to construct plasmid libraries of greater than $10^9$ recombinants", *Electroporation and Electrofusion*, 291–301 (1992).

Ellington and Szostack, "In vitro selection of RNA molecules that bind specific ligands", *Nature*, 346:818–822 (1990).

Felici et al., "Selection of antibody ligands from a large library of oligopeptides expressed on a multivalent exposition vector", *J. Mol. Biol.*, 222:301–310 (1991).

Flashner and Gralla, "Dual mechanism of repression at a distance in the lac operon", *Proc. Natl. Acad. Sci. USA*, 85:8968–8972 (1988).

Garrard et al., "$F_{ab}$ assembly and enrichment in a monovalent phage display system", *Bio/Technology*, 9:1373–1377 (1991).

Geysen et al., "Strategies for epitope analysis using peptide synthesis", *J. Immunol. Meth.*, 102:259–274 (1987).

Goldsmith et al., "Adsorption protein of the bacteriophage fd: isolation, molecular properties, and location in the virus", *Biochem.*, 16(12):2686–2694 (1977).

Gordon et al., "Missense Mutation in the LacI Gene of *Escherichia coli*; Inferences on the Structure of the Repressor Protein", *J. Mol. Biol.*, 200:239–251 (1988).

Greenwood et al., "Multiple display of foreign peptides on a filamentous bacteriophage", *J. Mol. Biol.*, 220:821–827 (1991).

Harlow et al., "Antibodies: A Laboratory Manual", *Cold Spring Harbor Laboratory*, 23–35 (1988).

Hoogenboom et al., "Multi-subunit proteins on the surface of filamentous phage: methodologies for displaying antibody (fab) heavy and light chains", *Nucleic Acids Res.*, 19(15):4133–4137 (1991).

Hsieh et al., "Influence of Sequence and Distance between Two Operators on Interaction with the lac Repressor", *J. Biol. Chem.*, 262(30):14583–14591 (1987).

Hu and Davidson, "Targeting the *Escherichia coli* lac repressor to the mammalian cell nucleus", *Gene*, 99:141–150 (1991).

Huse et al., "Generation of a large combinatorial library of the immunoglobulin repertoire in phage lambda", *Science*, 246:1275–1281 (1989).

Huse, "Antibody Engineering: A Practical Guide", Borrebaeck, ed., W. H. Freeman Company, 103 (1992).

Il'ichev et al., "M13 filamentous bacteriophage in protein engineering," *Molekulyarnaya Biologiya* 24(2):530–535 (1990).

Jacobs et al., "High-efficiency electro-transformation of *Escherichia coli* with DNA from ligation mixtures", *Nucleic Acids Research*, 18:1653 (1990).

Kang et al., "Linkage of recognition and replication functions by assembling combinatorial antibody fab libraries along phage surfaces," *Proc. Natl. Acad. Sci. USA* 88:4363–4366 (1991).

Kania and Brown, "The functional repressor parts of a tetrameric lac repressor-β-galactosidase chimaera are organized as dimers," *Proc. Natl. Acad. Sci. USA* 73(10):3529–3533 (1976).

Kleina and Miller, "Genetic Studies of the lac Repressor XIII. Extensive Amino Acid Replacements Generated by the Use of Natural and Synthetic Nonsense Supporters,". *J. Mol. Biol.* 212:295–318 (1990).

Knight et al., "The Arc and Mnt repressors; A new class of sequence-specific DNA Binding Protein," *J. Biol. Chem.* 264(7):3639–3642 (1989).

Koob and Szybalski, "Cleaving Yeast and *Escherichia coli* Genomes at a Single Site," *Science* 250:271–273 (1990).

Krämer et al., "Lac repressor forms loops with linear DNA carrying two suitably spaced lac operators," *EMBO J.* 6(5):1481–1491 (1987).

Labow et al., "Converse of the lac Repressor into an Allosterically regulated Transcriptional Activator for Mammalian Cells," *Mol. Cell. Biol.* 10(7):3343–3356 (1990).

Levens, et al., "Novel Method for Identifying Sequence-Specific DNA-Binding Proteins," *Mol. Cell. Biol.* 5(9):2307–2315 (1985).

Lundeberg et al., "Rapid colorimetric quantification of PCR-amplified DNA," *Bio/Tech.* 10(1):68–75 (1991).

McCafferty et al., "Phage antibodies: filamentous phage displaying antibody variable domains," *Nature* 348:552–554 (1990).

Maurizot and Grebert, "Thermodynamic parameters of the binding of the tight binding I12X86 lac repressor to operator and non-operator DNA," *FEBS Lett.* 239(1):105–108 (1988).

Mossing and Record, "Upstream Operators Enhance Repression of the lac Promoter," *Science* 233:889–892 (1986).

Müller-Hill and Kania, "Lac repressor can be fused to β-galactosidase," *Nature* 249:561–563 (1974).

Oliphant et al., "Cloning of random-sequence oligodeoxynucleo-tides," *Gene* 44:177–183 (1986).

Panayotatos et al., "Biosynthesis of a Repressor/Nuclease Hybrid protein," *J. Biol. Chem.* 264(25):15066–15069 (1989).

Parmley and Smith, "Antibody-selectable filamentous fd phage vectors: affinity purification of target genes," *Gene* 73:305–318 (1988).

Parmley et al., "Filamentous fusion phage cloning vectors for the study of epitopes and design of vaccines," *Adv. Exp. Med. Biol.* 251:215–218 (Abstract) (1989).

Plückthun and Ge, "The rationality of random screening—efficient methods of selection of peptides and oligonucleotide ligands," *Angew. Chem. Int. Ed. Engl.* 30(3):296–298 (1991).

Sadler et al., "A perfectly symmetric lac operator binds the lac repressor very tightly," *Proc. Natl. Acad. Sci. USA* 80:6785–6789 (1983).

Scott et al., "Searching for peptide ligands with an epitope library," *Science* 249:386–390 (1990).

Scott et al., "An Epitope Library," *Advances in Gene Technology: The Molecular Biology of Immune Diseases and the Immune Response*, Proceedings of the 1990 Miami Bio/Technology Winter Symposia (eds. Streilein et al., IRL Press, New York), p. 224.

Shigekawa and Dower, "Electroporation of eukaryotes and Prokaryotes: A general approach to the introduction of macromolecules into cells," *BioTechniques* 6:742–751 (1988).

Simons et al., "Possible ideal lac opeator: *Escherichia coli* lac operator–like sequences from eukaryotic genomes lack the central G–C pair," *Proc. Natl. Acad. Sci. USA* 81:1624–1628 (1984).

Skerra et al., "Assembly of a functional immunoglobulin $f_v$ fragment in *Escherichia coli*," *Science* 240:1038–1041 (1988).

Smith "Filamentous fusion phage: novel expression vectors that display cloned antigens on the virion surface," *Science* 228:1315–1317 (1985).

Smith et al., "An Epitope Library," *J. Cell Biochem. Supp.* 14C:246, abst. CK319 (19th Ann. Mtg., UCLA Symp. Mol. Cell Biol. (1990)).

Thiesen and Bach, "Target Detection Assay (TDA): a versatile procedure to determine DNA binding sites as demonstrated on SP1 protein, " *Nucleic Acids Res.* 18(11):3203–3209 (1990).

Tuerk and Gold, "Systematic Evolution of Ligands by Exponential Enrichment: RNA Ligands to Bacteriophage T4 DNA Polymerase," *Science* 249:505–510 (1990).

Ward et al., "Binding activities of a repertoire of single immunoglobulin variable domains secreted from *Escherichia coli*," *Nature* 341:544–545 (1989).

Whitson et al., "Influence of Supercoiling and Sequence Context on Operator DNA Binding with lac Repressor," *J. Biol. Chem.* 262(30):14592–14599 (1987).

Wilson and Gough, "High voltage *E. coli* electro–transformation with DNA following ligation," *Nucleic Acids Research* 16:11820 (1988).

Winnacker, "From Genes to Clones, Introduction to Gene Technology," pp. 46–53 (Publisher: VCH, Weinheim, Germany, 1987).

Young et al., "Yeast polymerase II genes: isolation with antibody probes," *Science* 222:778–782 (1983).

Zacher et al., "A new filamentous phage cloning vector: fd–tet," *Gene* 9:127–140 (1980).

David Levens and Peter Howley, "Novel Method for Identifying Sequence–Specific DNA–Binding Proteins", *Molecular and Cellular Biology*, 5(9) 2307–2315 (1985).

Joakim Lundeberg et al., "Rapid Colorimetric Quantification of PCR–Amplified DNA", *BioTechniques*, 10(1) 68–75 (1991).

Craig Tuerk and Larry Gold, "Systematic Evolution of Ligands by Exponential Enrichment: RNA Ligands to Bacteriophage T4 DNA Polymerase", *Science* 24(9) 505–510 (1990).

Millard G. Cull et al., "Screening for receptor ligands using large libraries of peptides linked to the C terminus of the lac repressor", *Proc. Natl. Acad. Sci. USA* 89 1865–1869 (1992).

Peter J. Schatz, "Construction and screening of biological peptide libraries", *Current Opinion in Biotechnology*, 5(5) 487–494 (1994).

Michael J. Calcutt et al., "Isolation and Characterization of Nucleic Acid–Binding Antibody Fragments from Autoimmune Mice–Derived Bacteriophage Display Libraries," *Gene*, 137, (1993) pp. 77–83.

X. Cheng et al., "Identification of a Biologically Significant DNA–Binding Peptide Motif by Use of a Random Phage Display Library," *Gene*, 171, (1996), pp. 1–8.

Christian M. Gates et al., "Affinity Selective Isolation of Ligands from Peptide Libraries Through Display on a Iac Repressor 'Headpiece Dimer'," *J. Mol. Biol.*, Edited by P. E. Wright, vol. 255, Janvier 1996, pp. 373–386.

Alexander Gragerov et al., "Specify of Dnak–Peptide Binding," *J. Mol. Biol.*, 1994, vol. 235, Edited by P. von Hippel, pp. 848–854.

Margareta Krook et al., "Selection of Peptides With Affinity for Single Stranded DNA Using a Phage Display Library," *Biochemical and Biophysical Research Communications*, Oct. 28, 1994, vol. 204, No. 2, pp. 849–854.

| #/Rnd/ELISA | | | PEPTIDE SEQUENCE |
|---|---|---|---|
| dynB | | 1.0 | .....YGGFLR\|RQFKVV\|T |
| 21 | 4 | 1.2 | .......TGK\|RGFKVV\|CNS |
| 22 | 4 | 1.2 | ........K\|RNFKVV\|GSPCG |
| 10 | 4 | 0.3 | ...SDSGNGLGI\|RRFKVS\|S* |
| 30 | 4 | 0.9 | .........GT\|RPFKVS\|EYIL |
| 35 | 4 | 0.2 | ...SLKDENNKR\|RIFKVS\|S* |
| 57 | 3 | 0.9 | ........SYLR\|REFKVS\|GV |
| 24 | 4 | 0.9 | ......GWRSCP\|RQFKVT\| |
| 45 | 3 | 0.9 | .........IK\|RGFKIT\|SAMS |
| 47 | 3 | 0.8 | .......VRFIA\|RPFRIT\|G |
| 71 | 2 | 1.1 | ..........A\|RAFRVT\|RIAGV |
| 74 | 2 | 0.2 | .......KNETR\|RPFRQT\|A |
| 68 | 2 | 0.6 | ........VNH\|RRFSVV\|HSY |
| 48 | 3 | 0.4 | .......VSSS\|RTFNVT\|RR |
| 46 | 3 | 0.3 | .........G\|RSFHVT\|SFGSV |
| 4 | 4 | 1.1 | ......RSTTV\|RQHKVV\|G |
| 15 | 4 | 1.2 | .......ERPN\|RLHKVV\|HA |
| 73 | 2 | 0.5 | ........WQN\|RTHKVV\|SGR |
| 78 | 2 | 1.1 | ..........A\|RKHKVT\|H |
| 40 | 3 | 1.1 | ........RQVT\|RLHKVI\|H |
| 11 | 4 | 1.0 | ........CPGE\|RMHKAV\|RA |
| 2 | 4 | 1.0 | .........SRC\|RNHRVV\|TSQ |
| 26 | 4 | 0.8 | .........NDG\|RPHRVV\|RCG |
| 9 | 4 | 0.8 | ..........EI\|RRHRVT\|ERVD |
| 56 | 3 | 1.1 | ..........LR\|RLHRVT\|NTMT |
| 69 | 2 | 1.1 | ........VKQ\|RLHSVV\|RPG |
| 7 | 4 | 1.1 | .......VTQRV\|RSNKVV\|S |
| 20 | 4 | 1.1 | ......HVEKIK\|RLNKVV\| |
| 23 | 4 | 1.2 | ........RLKT\|RLNKVV\|MD |
| 63 | 2 | 0.4 | ..........V\|RMNKVV\|CEKLW |
| 49 | 3 | 0.3 | ........DLK\|RLNRVV\|GH |
| 19 | 4 | 0.8 | .........RI\|RNNKVI\|AYHS |
| 36 | 4 | 0.5 | ........SRV\|RSNKVI\|MSI |
| 77 | 2 | 0.6 | .........SC\|RLNKVI\|ARPV |
| 33 | 4 | 0.5 | ......RALSKD\|RLNKVT\| |
| 58 | 3 | 1.1 | ......CTTERS\|RQWKVT\| |
| 16 | 4 | 1.1 | ..........A\|RPWKIT\|RNEPG |
| 72 | 2 | 0.3 | .......GVSEC\|RKWKIV\|Q |
| 6 | 4 | 1.2 | ........TTL\|RRYKVT\|GER |
| 34 | 4 | 1.1 | .......IADR\|RPYRVT\|RP |
| 76 | 2 | 1.2 | ......AGKVL\|RAYKIV\|E |
| 8 | 4 | 1.0 | .........QK\|RLMKVI\|FEGR |
| 55 | 3 | 1.0 | ......EVPHRF\|RWTKHM\| |

ELISA+ brace spans rows 2–55.

*FIG. 3A.*

| #/Rnd/ELISA | PEPTIDE SEQUENCE |
|---|---|
| 13 4 0.1 | . . . . . . S T T G R\|R S F K V S\|S * |
| 14 4 0.2 | . . . . . . R L P G\|R M F K V S\|S * |
| 28 4 0.1 | . . . . . . V G S F K\|R T F K V S\|C |
| 29 4 0.1 | . . . . . . . . R G\|R M F K V S\|S * |
| 54 3 0.1 | . P G R W V R G V G I\|R C F K V S\|S * |
| 60 2 0.1 | . . . . . . . R M S\|R L F K V S\|S * |
| 1 4 0.1 | . . P D V L R A V A T\|R Q H K V S\|S * |
| 27 4 0.2 | . . . . . . . . R V\|R G H R V V\|M Y N E |
| 64 2 0.1 | . . . . . . E C L H R\|R V H K I L\|S |
| 61 2 0.1 | . . . . . . G L K C\|R P M K V N\|A D |
| 50 3 0.1 | . . . . . . . . R H\|R P F G W V\|N K R S |
| 52 3 0.2 | . . . . . . . . A A\|R L F S Q I\|R R F P |
| 53 3 0.1 | . . . . . . . . R V\|R W H M V T\|G D K G |
| 31 4 0.1 | . . . . . . . . R F\|R N C S I I\|S A R G |
| 62 2 0.1 | . . . . . . . Y G V P\|R I V A H Q\|L M |

ELISA⁻ brackets rows 27 through 62.

pJS141 (cys free lacI) and pJS142 (WT lacI) LIBRARY VECTORS: (SEQ. ID NOS. 88, 89)

```
————lacI————————————linker————————————
                                   Sfi I                        Eag I
Xho I                              Stu I        Hpa I                    Sfi I
L   E   S   G   Q   V   V   H   G   E   Q   V   G   G   E   A   S   G   A   V   N   G   R   G   L
CTCGAGAGCGGGCAGgtggtgcatggggagcaggtggtggtgagGCCTCCGGGGCCGTTAACGGCCGTGGCCT
GAGCTCTCGCCCGTCcaccacgtaccccctcgtccaccactcCGGAGGCCCCGGCAATTGCCGGCACCGGA Msc I         Sal I
A   G   Q   *STOP
AGCTGGCCAA|TAAgtcgac 99
TCGACCGGTT ATTcagctg
```

LIBRARY CONSTRUCTION AFTER SfiI DIGESTION: (SEQ. ID NOS. 90, 91)

```
————lacI————————————linker————————————library——
                                   Sfi I                                              BspEI
Xho I                              Stu I                    G   G   G   Xn    *
L   E   S   G   Q   V   V   H   G   E   Q   V   G   G   E   A   S   G   G   G   gagtggt (NNK)n taactaa
CTCGAGAGCGGGCAGtggtgcatggggagcaggtggtggtgagGCCTCCG gagtggt (NNK)n taactaa        attgatt
GAGCTCTCGCCCGTCcaccacgtaccccctcgtccaccactcCGGA ggcctccacca Msc I     Sal I
gta|aagc TGGCCA|ATAAgtcgac
catt TCGACCGGTTATTcagctg
```

| ISOLATE | HEADPIECE AA SEQUENCE | LINKERS |
|---|---|---|
| A. (Hp #1) | MKPVTLYDVAEYAGVSYQTVSRVVNQASHVSAKTREKVEAAMAELNYIP | XXXXX |
| (Hp #2) | KPVTLYDVAEYAGVSYQTVSRVVNQASHVSAKTREKVEAAMAELNYIP | XXXX-EPITOPE |
| B. B7 | ................................................ | GRCR |
| | ................................................ | GPNQ-RQFKVVT |
| B10 | RTSNVIRCRRVCRCLLSDRFPRGEPGQPRFCENAGKSGSGDGGAD.... | VYCR |
| | ................................................ | DHPV-RQFKVVT |
| C4 | ................................................ | TVVL |
| | ................................................ | RRYP-RQFKVVT |
| C5 | -LSNVIRCRRVCRCLLSDRFPRGEPGQPRFCENAGKSGSGDG...... | KMCM |
| | ................................................ | PAQS-RQFKVVT |
| C. A4.2 | ???????????????......R..............G..P.....V. | GRCR |
| | ..........................................T.???? | ????-??????? |
| A4.3 | ......................R........................ | LRRC |
| | ................................................ | LSKR-RQFKVVT |
| A4.5 | ................T...P..R..............G.E....G. | GRCR |
| A4.7 | ......................R.................E...... | RSQE-RRFKVVT |
| | ................................................ | SCVP |
| A4.8 | .......................D..E.................... | KRRV-RQFKVVT |
| | .................R.............................. | SCVP |
| | ................................................ | ????-??????? |
| B4.5 | ..M...................R........A............... | GRCR |
| | ................................................ | GPNQ-RQFKVVT |
| B4.7 | .........A..............................G...... | GRCR |
| | ................................................ | GPNQ-RQFKVVT |
| B4.8 | ...............................G.............V. | GRCR |
| | ................................................ | EHAR-RQFK??? | pCMG14 LIBRARY VECTOR, CLONING SITES AT 3' END OF HEADPIECE DIMER GENE:

```
--------HEADPIECE--------><----LINKER---->
                          Sfi I            Eag I
                    Stu I      Hpa I    Sfi I    Msc I      Sal I
E  A  A  M  A  E  L  N  Y  I  P  R  S  Q  E  A  S  G  A  V  N  G  R  G  L  A  G  Q  *
GAAGCGGGCGATGGCGGAGCTGAATTACATTCCCcggtcgcaggagGCCTCCGGGGCCGTTAACGGCCGTAGCTGGCCAATAAgtc
CTTCGCCCGCTACCGCCTCGACTTAATGTAAGGGgccagcgtcctcCGGAGGCCCCGGCAATTGCCGGCATCGACCGGTTATTcag
gac
ctg
```

FIG. 7B.

LIBRARY CONSTRUCTION AFTER SfiI DIGESTION:

```
--------HEADPIECE---------------LINKER----------><LIBRARY>    ON-1679
                                  BspE I                         ↓
        Stu I                                                        Msc I
Xho I                                                *
E  A  A  M  A  E  L  N  Y  I  P  R  S  Q  E  A  S  G  G  G  G  X₁₂    taactaagtaaagc TGGCCAA
GAAGCGGGCGATGGCGGAGCTGAATTACATTCCCcggtcgcaggagGCCTCCG gaggtggt(NNK)₁₂
CTTCGCCCGCTACCGCCTCGACTTAATGTAAGGGgccagcgtcctcCGGA ggcctccacca           attgattcatt TCGACCGGTT
                                                      ↑                              ↑
Sal I                                              ON-829                         ON-830

TAAgtcgac
ATTcagctg
```

FIG. 7C.

| CLONE | PEPTIDE SEQUENCE |
|---|---|
| pCMG39 (HIGH AFFIN.) | R Q F K V V T |
| pCMG38 (LOW AFFIN.) | K Q F K V T K T |
| HpD-2 | F H V T G K A W C P L R |
| HpD-3 | T F K V V P Q M E G M T |
| HpD-4 | E V Q I R S F R V G K V |
| HpD-6 | Y L S T E R P R M F H L T K |
| HpD-7 | V R M H K V S E Q S R F |
| HpD-8 | H S R A F R A T K S V V |
| HpD-10 | R H H M F S V T R I W D |
| HpD-11 | A F A V T H K R N R G Y |
| HpD-12 | R S L A G R R F R I L G N |
| HpD-13 | I E H P Y R I D R M V M |
| HpD-14 | H R S L P S T R R F R L T K |
| HpD-15 | F S V V R G C R I F R I N |
| HpD-16 | Q F R V V T L T S P L A |
| HpD-17 | L A R P F R R A K L D G |
| HpD-18 | L L R R P F M V N R N T |
| HpD-19 | H R Y N R T V G I N E V |
| HpD-21 | R R R R N C Q I V G Y W |
| LacI-1 | R G L M R R S Y K T V |
| LacI-2 | M G G R R V R L A R I I N |
| LacI-3 | S G R P F R M E R Q R P |
| LacI-4 | K M V R ? I F R T I P G |
| LacI-5 | L R R M R V V I R |
| LacI-6 | K W S G L G G G R V L V N |
| LacI-7 | R R W A T S G P R Q L Y |
| LacI-8 | E P K F K N F R V V F G N |
| LacI-9 | R W F S P G R R A F M V N |
| LacI-10 | G R P F R Q N S P V V F |
| LacI-11 | W V P R M G R H L S T L |
| LacI-12 | R T R H V F K V I H G F |
| LacI-14 | N A R R M Y S V A G M D |
| LacI-15 | W R K F A L L G S G P T |
| LacI-16 | H R A Y R I A T M F S G |
| LacI-19 | R G L M R R S Y K T V |
| LacI-22 | A R H R M F Q W A M V G |
| LacI-23 | I M I G K E G A V S S S |

FIG. 8.

PEPTIDE LIBRARY AND SCREENING METHOD

CROSS-REFERENCE TO RELATED APPLICATIONS

The present application is a continuation-in-part of U.S. Ser. No. 08/290,641, (now U.S. Pat. No. 5,498,530) filed Aug. 15, 1994, which is a continuation of U.S. Ser. No. 07/963,321, now U.S. Pat. No. 5,338,665, filed Oct. 15, 1992, which is a continuation-in-part of U.S. Ser. No. 07/778,233, filed Oct. 16, 1991 now U.S. Pat. No. 5,270,170, and is related to copending U.S. Ser. No. 07/718,577, filed Jun. 20, 1991 (now U.S. Pat. No. 5,432,018), and to copending U.S. Ser. No. 07/541,108, filed Jun. 20, 1990, which is a continuation-in-part of copending U.S. Ser. No. 07/517,659, filed Jun. 20, 1990, each of which is incorporated by reference in its entirety for all purposes.

FIELD OF THE INVENTION

The present invention relates generally to methods for selecting peptide ligands to receptor molecules of interest and, more particularly, to methods for generating and screening large peptide libraries for peptides with desired binding characteristics.

BACKGROUND OF THE INVENTION

The isolation of ligands that bind biological receptors is fundamental to understanding signal transduction and to discovering new therapeutics. The ability to synthesize DNA chemically has made possible the construction of extremely large collections of nucleic acid and peptide sequences as potential ligands. Recently developed methods allow efficient screening of libraries for desired binding activities (see Pluckthun & Ge, *Angew. Chem. Int. Ed. Engl.* 30, 296–298 (1991). For example, RNA molecules with the ability to bind a particular protein (see Tuerk & Gold, *Science* 249, 505–510 (1990) or a dye (see Ellington & Szostak, *Nature* 346, 818–822 (1990) have been selected by alternate rounds of affinity selection and PCR amplification. A similar technique was used to determine the DNA sequences that bound a human transcription factor (see Thiesen & Bach, *Nucl. Acids Res.* 18, 3203–3209 (1990)).

Application of efficient screening techniques to peptides requires the establishment of a physical or logical connection between each peptide and the nucleic acid that encodes the peptide. After rounds of affinity enrichment, such a connection allows identification, usually by amplification and sequencing, of the genetic material encoding interesting peptides. Several phage based systems for screening proteins and polypeptides have been described. The fusion phage approach of Parmley and Smith, 1988, *Gene* 73, 305–318, can be used to screen proteins. Others have described phage based systems in which the peptide is fused to the pIII coat protein of filamentous phage (see Scott & Smith, *Science* 249, 386–390 (1990); Devlin et al., *Science* 249, 404–406 (1990); and Cwirla et al., *Proc. Natl. Acad. Sci. USA* 87, 6378–6382 (1990); each of which is incorporated herein by reference).

In these latter publications, the authors describe expression of a peptide at the amino terminus of or internal to the pIII protein. The connection between peptide and the genetic material that encodes the peptide is established, because the fusion protein is part of the capsid enclosing the phage genomic DNA. Phage encoding peptide ligands for receptors of interest can be isolated from libraries of greater than $10^8$ peptides after several rounds of affinity enrichment followed by phage growth. Other non-phage based systems that could be suggested for the construction of peptide libraries include direct screening of nascent peptides on polysomes (see Tuerk & Gold, supra) and display of peptides directly on the surface of *E. coli*. As in the filamentous phage system, all of these methods rely on a physical association of the peptide with the nucleic acid that encodes the peptide.

There remains a need for methods of constructing peptide libraries in addition to the methods described above. For instance, the above methods do not provide random peptides with a free carboxy terminus, yet such peptides would add diversity to the peptide structures now available for receptor binding. In addition, prior art methods for constructing random peptide libraries cannot tolerate stop codons in the degenerate region coding for the random peptide, yet stop codons occur with frequency in degenerate oligonucleotides. Prior art methods involving phage fusions require that the fusion peptide be exported to the periplasm and so are limited to fusion proteins that are compatible with the protein export apparatus and the formation of an intact phage coat.

The present invention provides random peptide libraries and methods for generating and screening those libraries with significant advantages over the prior art methods.

SUMMARY OF THE INVENTION

The present invention provides random peptide libraries and methods for generating and screening those libraries to identify peptides that bind to receptor molecules of interest. The peptides can be used for therapeutic, diagnostic, and related purposes, e.g., to bind the receptor or an analogue of the receptor and so inhibit or promote the activity of the receptor.

The peptide library of the invention is constructed so that the peptide is expressed as a fusion product; the peptide is fused to a DNA binding protein. The peptide library is constructed so that the DNA binding protein can bind to the recombinant DNA expression vector that encodes the fusion product that contains the peptide of interest. The method of generating the peptide library of the invention comprises the steps of (a) constructing a recombinant DNA vector that encodes a DNA binding protein and contains a binding site for the DNA binding protein; (b) inserting into the coding sequence of the DNA binding protein in the vector of step (a) a coding sequence for a peptide such that the resulting vector encodes a fusion protein composed of the DNA binding protein and the peptide; (c) transforming a host cell with the vector of step (b); and (d) culturing the host cell transformed in step (c) under conditions suitable for expression of the fusion protein.

The screening method of the invention comprises the steps of (a) lysing the cells transformed with the peptide library under conditions such that the fusion protein remains bound to the vector that encodes the fusion protein; (b) contacting the fusion proteins of the peptide library with a receptor under conditions conducive to specific peptide—receptor binding; and (c) isolating the vector that encodes a peptide that binds to said receptor. By repetition of the affinity selection process one or more times, the plasmids encoding the peptides of interest can be enriched. By increased stringency of the selection, peptides of increasingly higher affinity can be identified.

The present invention also relates to recombinant DNA vectors useful for constructing the random peptide library, the random peptide library, host cells transformed with the recombinant vectors of the library, and fusion proteins expressed by those host cells.

BRIEF DESCRIPTION OF THE DRAWINGS

FIGS. 3A and 3B (SEQ ID NOS.:7–64) show sequences isolated by panning with the D32.39 antibody. Each sequence is listed with a clone number, the panning round in which the clone was isolated, and the result of the ELISA with D32.39 antibody. The sequences are aligned to show the D32.39 epitope that they share (box).

FIG. 4 (SEQ ID NOS.88–91) shows the linker sequences from vectors pJS141 and pJS142.

FIG. 6 (SEQ ID NOS.87 AND 92–122) Sequences of headpiece dimer proteins. (a) Sequence of headpiece domains and adjoining linkers as constructed for the headpiece dimer linker library. (b) Protein sequence of linker library clones isolated after four rounds of panning selection, showing linker sequences and residue changes from the original headpiece protein sequence where indicated. Unchanged residues are marked with a dot "."; residue deletions are noted with a hyphen "-". (c) Protein sequences of clones isolated after mutagenesis and four rounds of panning selection. Unsequenced positions are noted with question marks.

FIGS. 7A, 7B, and 7C (SEQ ID NOS.123–126) Construction of headpiece dimer libraries in vector pCMG14. (7A) Restriction map and positions of genes. The library plasmid includes: the rrnB transcriptional terminator, the bla gene to permit selection on ampicillin, the M13 phage intragenic region (M13 IG) to permit rescue of single-stranded DNA, a plasmid replication origin (ori), one lacO$_s$ sequence, and the araC gene to permit positive and negative regulation of the araB promoter driving expression of the headpiece dimer fusion gene. (7B) Sequence of the cloning region at the 3' end of the headpiece dimer gene, including the SfiI and EagI sites used during library construction. (7C) Ligation of annealed ON-1679, ON-829, and ON-830 to SfiI sites of pCMG14 to produce a library. Single spaces in the sequence indicate sites of ligation.

FIG. 8 (SEQ ID NOS.127–162) Sequences of D32.39 MAb-specific peptides isolated from random libraries after four rounds of panning. Peptides derived from the headpiece dimer library are preceded by "HpD", sequences from the lacI peptides-on-plasmids library are preceded by "lacI". The isolate numbers correspond to those in FIG. 9. The boxed portion represents the alignment of peptide sequence with the known D32.39 monoclonal antibody epitope RQFKVVT (SEQ ID NO.66).

DESCRIPTION OF THE SPECIFIC EMBODIMENTS

Figure 1:
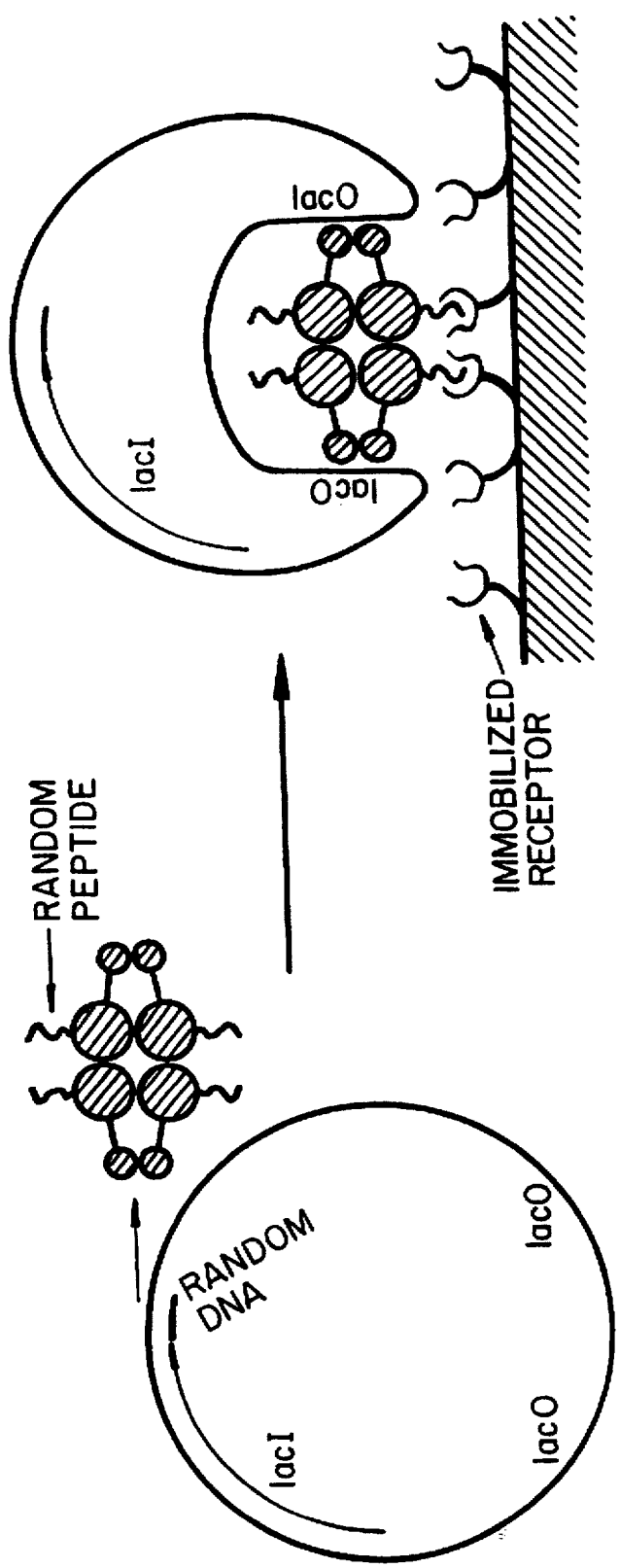
FIG. 1 shows a recombinant vector of a random peptide library of the invention. In this embodiment of the invention, the DNA binding protein is the lacI gene product, the fusion protein forms a tetramer, and the tetramer interacts with the vector and immobilized receptor, as shown in the Figure. The library plasmid carries the lacI gene with random coding sequence fused to the 3' end of the coding sequence of the gene, as well as two lacO sequences. The lac repressor-peptide fusions produced by the hybrid genes bind to the lacO sites on the same plasmid that encodes them. After lysis of cells containing the random library, those plasmid-repressor-peptide complexes that specifically bind a chosen receptor are enriched by avidity panning against the immobilized receptor. Transformation of E. coli with recovered plasmids allows additional rounds of panning or sequencing of isolated clones.

For purposes of clarity and a complete understanding of the invention, the following terms are defined.

"DNA Binding Protein" refers to a protein that specifically interacts with deoxyribonucleotide strands. A sequence-specific DNA binding protein binds to a specific sequence or family of specific sequences showing a high degree of sequence identity with each other (e.g., at least about 80% sequence identity) with at least 100-fold greater affinity than to unrelated sequences. The dissociation constant of a sequence-specific DNA binding protein to its specific sequence(s) is usually less than about 100 nM, and may be as low as 10 nM, 1 nM, 1 pM or 1 fM. A nonsequence-specific DNA binding protein binds to a plurality of unrelated DNA sequences with a dissociation constant that varies by less than 100-fold, usually less than tenfold, to the different sequences. The dissociation constant of a nonsequence-specific DNA binding protein to the plurality of sequences is usually less than about 1 µM. In embodiments of the invention in which RNA vectors are used, DNA binding protein can also refer to an RNA binding protein.

"Epitope" refers to that portion of an antigen that interacts with an antibody.

"Host Cell" refers to a eukaryotic or procaryotic cell or group of cells that can be or has been transformed by a recombinant DNA vector. For purposes of the present invention, a host cell is typically a bacterium, such as an E. coli K12 cell or an E. coli B cell.

"Ligand" refers to a molecule, such as a random peptide, that is recognized by a particular receptor.

"Ligand Fragment" refers to a portion of a gene encoding a ligand and to the portion of the ligand encoded by that gene fragment.

"Ligand Fragment Library" refers not only to a set of recombinant DNA vectors that encodes a set of ligand fragments, but also to the set of ligand fragments encoded by those vectors, as well as the fusion proteins containing those ligand fragments.

"Linker" or "spacer" refers to a molecule or group of molecules that connects two molecules, such as a DNA binding protein and a random peptide, and serves to place the two molecules in a preferred configuration, e.g., so that the random peptide can bind to a receptor with minimal steric hindrance from the DNA binding protein.

"Peptide" or "polypeptide" refers to a polymer in which the monomers are alpha amino acids joined together through amide bonds. Peptides are two or often more amino acid monomers long. Standard abbreviations for amino acids are used herein (see Stryer, 1988, *Biochemistry*, Third Ed., incorporated herein by reference.)

"Random Peptide" refers to an oligomer composed of two or more amino acid monomers and constructed by a stochastic or random process. A random peptide can include framework or scaffolding motifs, as described below.

"Random Peptide Library" refers not only to a set of recombinant DNA vectors that encodes a set of random peptides, but also to the set of random peptides encoded by those vectors, as well as the fusion proteins containing those random peptides.

"Receptor" refers to a molecule that has an affinity for a given ligand. Receptors can be naturally occurring or synthetic molecules. Receptors can be employed in an unaltered state or as aggregates with other species. Receptors can be attached, covalently or noncovalently, to a binding member, either directly or via a specific binding substance. Examples of receptors include, but are not limited to, antibodies, including monoclonal antibodies and antisera reactive with specific antigenic determinants (such as on viruses, cells, or other materials), cell membrane receptors, enzymes, and hormone receptors.

"Recombinant DNA Vector" refers to a DNA or RNA molecule that encodes a useful function and can be used to transform a host cell. For purposes of the present invention, a recombinant DNA vector typically is a phage or plasmid and can be extrachromosomally maintained in a host cell or controllably integrated into and excised from a host cell chromosome.

The present invention provides random peptide libraries and methods for generating and screening those libraries to identify either peptides that bind to receptor molecules of interest or gene products that modify peptides or RNA in a desired fashion. The peptides are produced from libraries of random peptide expression vectors that encode peptides attached to a DNA binding protein. A method of affinity enrichment allows a very large library of peptides to be screened and the vector carrying the desired peptide(s) to be selected. The nucleic acid can then be isolated from the vector and sequenced to deduce the amino acid sequence of the desired peptide. Using these methods, one can identify a peptide as having a desired binding affinity for a molecule. The peptide can then be synthesized in bulk by conventional means.

By identifying the peptide de novo, one need not know the sequence or structure of the receptor molecule or the sequence or structure of the natural binding partner of the receptor. Indeed, for many "receptor" molecules a binding partner has not yet been identified. A significant advantage of the present invention is that no prior information regarding an expected ligand structure is required to isolate peptide ligands of interest. The peptide identified will have biological activity, which is meant to include at least specific binding affinity for a selected receptor molecule and, in some instances, will further include the ability to block the binding of other compounds, to stimulate or inhibit metabolic pathways, to act as a signal or messenger, to stimulate or inhibit cellular activity, and the like.

The number of possible receptor molecules for which peptide ligands may be identified by means of the present invention is virtually unlimited. For example, the receptor molecule may be an antibody (or a binding portion thereof). The antigen to which the antibody binds may be known and perhaps even sequenced, in which case the invention may be used to map epitopes of the antigen. If the antigen is unknown, such as with certain autoimmune diseases, for example, sera, fluids, tissue, or cell from patients with the disease can be used in the present screening method to identify peptides, and consequently the antigen, that elicits the autoimmune response. One can also use the present screening method to tailor a peptide to a particular purpose. Once a peptide has been identified, that peptide can serve as, or provide the basis for, the development of a vaccine, a therapeutic agent, a diagnostic reagent, etc.

The present invention can be used to identify peptide ligands for a wide variety of receptors in addition to antibodies. These ligands include, by way of example and not limitation, growth factors, hormones, enzyme substrates, interferons, interleukins, intracellular and intercellular messengers, lectins, cellular adhesion molecules, and the like. Peptide ligands can also be identified by the present invention for molecules that are not peptides or proteins, e.g., carbohydrates, non-protein organic compounds, metals, etc. Thus, although antibodies are widely available and conveniently manipulated, antibodies are merely representative of receptor molecules for which peptide ligands can be identified by means of the present invention.

The peptide library is constructed so that the DNA binding protein-random peptide fusion product can bind to the recombinant DNA expression vector that encodes the fusion product that contains the peptide of interest. The method of generating the peptide library comprises the steps of (a) constructing a recombinant DNA vector that encodes a DNA binding protein and contains binding sites for the DNA binding protein; (b) inserting into the coding sequence of the DNA binding protein in a multiplicity of vectors of step (a) coding sequences for random peptides such that the resulting vectors encode different fusion proteins, each of which is composed of the DNA binding protein and a random peptide; (c) transforming host cells with the vectors of step (b); and (d) culturing the host cells transformed in step (c) under conditions suitable for expression of the fusion proteins. Typically, a random peptide library will contain at least $10^6$ to $10^8$ different members, although library sizes of $10^8$ to $10^{13}$ can be achieved.

The peptide library produced by this method is especially useful in screening for ligands that bind to a receptor of interest. This screening method comprises the steps of (a) lysing the cells transformed with the peptide library under conditions such that the fusion protein remains bound to the vector that encodes the fusion protein; (b) contacting the fusion proteins of the peptide library with a receptor under conditions conducive to specific peptide—receptor binding; and (c) isolating the vector that encodes a peptide that binds to said receptor. By repetition of the affinity selection process one or more times, the vectors that encode the peptides of interest may be enriched. By increased stringency of the selection, peptides of increasingly higher affinity can be identified. If the presence of cytoplasmic or periplasmic proteins interferes with binding of fusion protein to receptor, then partial purification of fusion protein-plasmid complexes by gel filtration, affinity, or other purification methods can be used to prevent such interference. For instance, purification of the cell lysate on a column (such as the Sephacryl S-400 HR column) that removes small proteins and other molecules may be useful.

The recombinant vectors of the random peptide library are constructed so that the random peptide is expressed as a fusion product; the peptide is fused to a DNA binding protein. A DNA binding protein of the invention must exhibit high avidity binding to DNA and have a region that can accept insertions of amino acids without interfering with the DNA binding activity. The half-life of a DNA binding protein-DNA complex produced by practice of the present method must be long enough to allow screening to occur. Typically, the half-life will be at least 15 min and often between one to four hours or longer.

Suitable DNA binding proteins for purposes of the present invention include proteins selected from a large group of known DNA binding proteins including transcriptional regulators and proteins that serve structural functions on DNA. Examples include: proteins that recognize DNA by virtue of a helix-turn-helix motif, such as the phage 434 repressor, the lambda phage cI and cro repressors, and the *E. coli* CAP protein from bacteria and proteins from eukaryotic cells that contain a homeobox helix-turn-helix motif; proteins containing the helix-loop-helix structure, such as myc and related proteins; proteins with leucine zippers and DNA binding basic domains such as fos and jun; proteins with 'POU' domains such as the Drosophila paired protein; proteins with domains whose structures depend on metal ion chelation such as $Cys_2His_2$ zinc fingers found in TFIIIA, $Zn_2(Cys)_6$ clusters such as those found in yeast Gal4, the $Cys_3His$ box found in retroviral nucleocapsid proteins, and the $Zn_2(Cys)_8$ clusters found in nuclear hormone receptor-type proteins; the phage P22 Arc and Mnt repressors (see Knight et al., *J. Biol. Chem.* 264, 3639–3642 (1989) and Bowie & Sauer, *J. Biol. Chem.* 264, 7596–7602 (1989) each of which is incorporated herein by reference); and others. Proteins that bind DNA in a non-sequence-specific manner are also used, for example, histones, protamines, and HMG type proteins. In addition, proteins could be used that bind to DNA indirectly, by virtue of binding another protein bound to DNA. Examples of these include yeast Gal80 and adenovirus E1A protein. Phage coat proteins, which associate with DNA by encapsidation of the DNA in a phage coat, and are used in the phage display methods of screening peptides discussed in the Background are typically not employed in the present invention.

Some DNA binding proteins can be selected from the above list by virtue of their possession of a dissociation half-life of at least fifteen min. Data on DNA half-lives are available for several DNA binding proteins. For example, the arc repressor of phage P22 has a dissociation half-life of 80 min (see, e.g., Knight et al., *J. Biol. Chem.* 264, 3639–3642 (1989), Vershon et al., *J. Mol. Biol.* 195, 323–331 (1987)). For other DNA binding proteins, dissociation half-life can be determined by standard biochemical procedures (see, e.g., Bourgeois, *Methods Enzymol.* 21D, 491–500 (1971) (filter binding assay), Knight & Sauer, *J. Biol. Chem.* 264, 13706–13710 (1989) (DNA modification protection assay)).

The lac repressor is one of the many DNA binding proteins that can be used in the construction of the libraries of the invention. The lac repressor, a 37 kDa protein, is the product of the *E. coli* lacI gene and negatively controls transcription of the lacZYA operon by binding to a specific DNA sequence called lacO. Structure-function relationships in the lac repressor have been studied extensively through the construction of thousands of amino acid substitution variants of the protein (see Gordon et al., *J. Mol. Biol.* 200, 239–251 (1988), and Kleina & Miller, *J. Mol. Biol.* 212, 295–318 (1990)). The repressor exists as a tetramer in its native form with two high affinity DNA binding domains formed by the amino termini of the subunits (see Beyreuther, *The Operon* (Miller and Reznikoff, eds., Cold Spring Harbor Laboratory, 1980), pp. 123–154). The two DNA binding sites exhibit strong cooperativity of binding to DNA molecules with two lacO sequences. A single tetramer can bind to suitably spaced sites on a plasmid, forming a loop of DNA between the two sites, and the resulting complex is stable for days (see Besse et al., *EMBO J.* 5, 1377–1381 (1986).; Flashner & Gralla, *Proc. Natl. Acad. Sci. USA* 85, 8968–8972 (1988); Hsieh et al., *J. Biol. Chem.* 262, 14583–14591 (1987); Kramer et al., *EMBO J.* 6, 1481–1491 (1987); Mossing & Record, *Science* 233, 889–892; and Whitson et al., *J. Biol. Chem.* 262, 14592–14599 (1987)).

The carboxy terminal domains of the lac repressor form the dimer and tetramer contacts, but significantly, fusions of proteins as large as β-galactosidase can be made to the carboxy terminus without eliminating the DNA binding activity of the repressor (see Muller-Hill and Kania, *Nature* 249, 561–563 (1974); and Brake et al., *Proc. Natl. Acad. Sci. USA* 75, 4824–4827 (1978)). The lac repressor fusion proteins of the present invention include not only carboxy terminus fusions but also amino terminus fusions and peptide insertions in the lac repressor. Substitutions of other sequences, including eukaryotic nuclear localization signals, transcriptional activation domains, and nuclease domains, have been made at both the amino and carboxy termini of the lac repressor without serious disruption of specific DNA binding (see Hu and Davidson, *Gene* 99, 141–150 (1991); Labow et al., *Mol. Cell. Biol.* 10, 3343–3356 (1990); and Panayotatos et al., *J. Biol. Chem.* 264, 15066–15069 (1989)).

The binding of the lac repressor to a single wild-type lacO is both tight and rapid, with a dissociation constant of $10^{-13}M$, an association rate constant of $7\times10^9M^{-1}s^{-1}$, and a half-life for the lac repressor-lacO complex of about 30 min. (see Barkley and Bourgeois, 1980, The Operon (Miller and Reznikoff, eds., Cold Spring Harbor Laboratory), pp. 177–220). The high stability of the lac repressor-DNA complex has permitted its use in methods for identifying DNA binding proteins (see Levens and Howley, *Mol. Cell. Biol.* 5, 2307–2315 (1985)), for quantifying PCR-amplified DNA (see Lundeberg et al., *BioTech.* 10, 68–75 (1991)), and for cleavage of the *E. coli* and yeast genomes at a single site (see Koob and Szybalski, *Science* 250, 271–273 (1990)). This stability is important for purposes of the present invention, because, for the affinity selection or "panning" step of the screening process to succeed, the connection between the fusion protein and the plasmid that encodes the fusion protein must remain intact for at least a portion of the complexes throughout the panning step.

In fact, for purposes of the present invention, a longer half-life is preferred. A variety of techniques can be used to increase the stability of the DNA binding protein-DNA complex. These techniques include altering the amino acid sequence of the DNA binding protein, altering the DNA sequence of the DNA binding site, increasing the number of DNA binding sites on the vector, adding compounds that increase the stability of the complex (such as lactose or ONPF for the lac system), and various combinations of each of these techniques.

An illustrative random peptide library cloning vector of the invention, plasmid pMC5, demonstrates some of these techniques. Plasmid pMC5 has two lacO sequences to take advantage of the strong cooperative interaction between a lac repressor tetramer and two lac repressor binding sites, and each of these sequences is the symmetric variant of the lacO sequence, called $lacO_s$ or $lacO_{id}$, which has about ten fold higher affinity for repressor than the wild-type sequence (see Sadler et al., *Proc. Natl. Acad. Sci. USA* 80, 6785–6789 (1983), and Simons et al., *Proc. Natl. Acad. Sci. USA* 81, 1624–1628 (1984)). Other "tight-binding" lac repressors and coding sequences for those repressors that can be used for purposes of the present invention are described in Maurizot and Grebert, *FEBS Lettrs.* 239(1), 105–108 (1988), incorporated herein by reference. See also Lehming et al., *EMBO J.* 6(10), 3145–3153 (1987).

Figure 2:
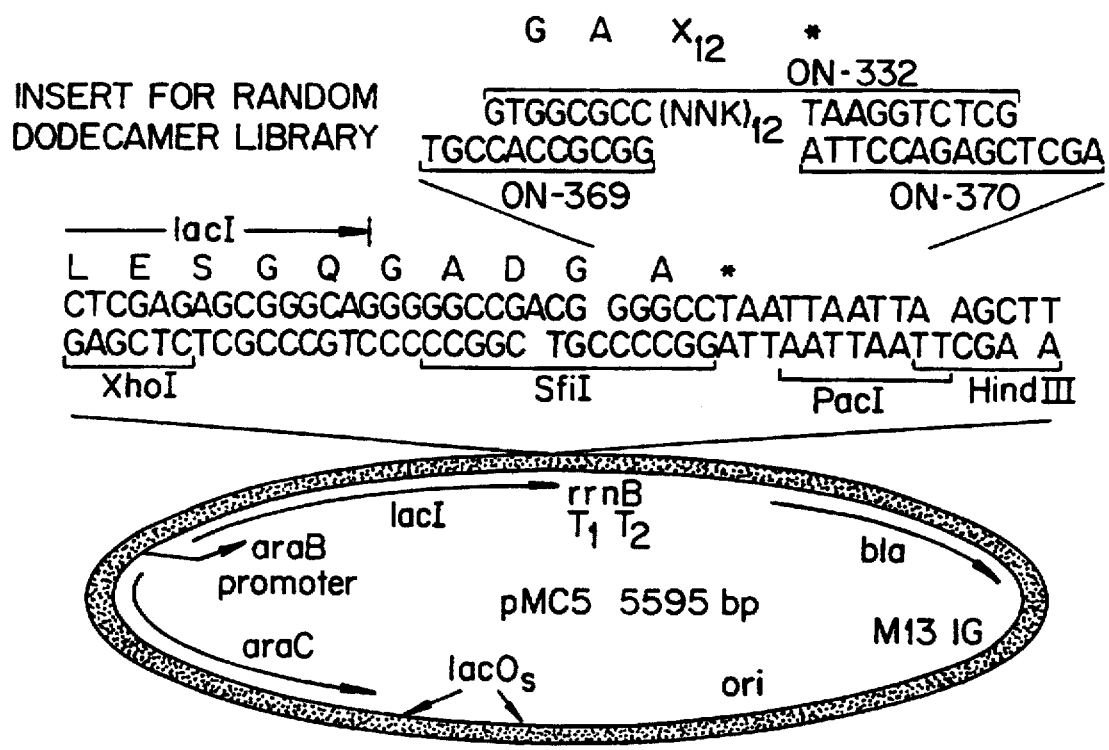
FIG. 2 (SEQ. ID NOS.:1–6) shows a partial restriction site, DNA sequence, and function map of plasmid pMC5. Hybridization of oligonucleotide ON-332 to oligonucleotides ON-369 and ON-370 produces a fragment with cohesive ends compatible with SfiI, HindIII digested plasmid pMC5. The ligation product adds sequence coding for twelve random amino acids to the end of lacI through a six codon linker. The library plasmid also contains: the rrnB transcriptional terminator, the bla gene to permit selection on ampicillin, the M13 phage intragenic region to permit rescue of single-stranded DNA, a plasmid replication origin (ori), two lacOs sequences, and the araC gene to permit positive and negative regulation of the araB promoter that drives expression of the lacI fusion gene.

Plasmid pMC5 is shown in FIGS. 1 and 2, and details of the construction of the plasmid are in Example 1, below. This library plasmid contains two major functional elements in a vector that permits replication and selection in *E. coli*. The lacI gene is expressed under the control of the araB promoter and has a series of restriction enzyme sites at the 3' end of the gene. Synthetic oligonucleotides cloned into these sites fuse the lac repressor protein coding sequence to additional random peptide coding sequence.

Once a vector such as pMC5 is constructed, one need only clone peptide coding sequences in frame with the DNA binding protein coding sequences to obtain a random peptide library of the invention. Thus, the random peptide library of the invention is constructed by cloning an oligonucleotide that contains the random peptide coding sequence (and any spacers, framework determinants, etc., as discussed below) into a selected cloning site of a vector that encodes a DNA binding protein and binding sites for that protein.

Using known recombinant DNA techniques (see generally, Sambrooke et al., *Molecular Cloning, A Laboratory Manual*, 2d ed., Cold Spring Harbor Laboratory Press, Cold Spring Harbor, N.Y., 1989, incorporated herein by reference), one can synthesize an oligonucleotide that, inter alia, removes unwanted restriction sites and adds desired ones, reconstructs the correct portions of any sequences that have been removed, inserts the spacer, conserved, or framework residues, if any, and corrects the translation frame (if necessary) to produce an active fusion protein comprised of a DNA binding protein and random peptide. The central portion of the oligonucleotide will generally contain one or more random peptide coding sequences (variable region domain) and spacer or framework residues. The sequences are ultimately expressed as peptides (with or without spacer or framework residues) fused to or in the DNA binding protein.

The variable region domain of the oligonucleotide encodes a key feature of the library: the random peptide. The size of the library will vary according to the number of variable codons, and hence the size of the peptides, that are desired. Generally, the library will be at least $10^6$ to $10^8$ or more members, although smaller libraries may be quite useful in some circumstances. To generate the collection of oligonucleotides that forms a series of codons encoding a random collection of amino acids and that is ultimately cloned into the vector, a codon motif is used, such as $(NNK)_x$, where N may be A, C, G, or T (nominally equimolar), K is G or T (nominally equimolar), and x is typically up to about 5, 6, 7, or 8 or more, thereby producing libraries of penta-, hexa-, hepta-, and octa-peptides or more. The third position may also be G or C, designated "S". Thus, NNK or NNS (i) code for all the amino acids, (ii) code for only one stop codon, and (iii) reduce the range of codon bias from 6:1 to 3:1. There are 32 possible codons resulting from the NNK motif: 1 for each of 12 amino acids, 2 for each of 5 amino acids, 3 for each of 3 amino acids, and only one of the three stop codons. With longer peptides, the size of the library that is generated can become a constraint in the cloning process, but the larger libraries can be sampled, as described below. The expression of peptides from randomly generated mixtures of oligonucleotides in recombinant vectors is discussed in oliphant et al., *Gene* 44, 77–183 (1986), incorporated herein by reference.

An exemplified codon motif $(NNK)_x$ produces 32 codons, one for each of 12 amino acids, two for each of five amino acids, three for each of three amino acids and one (amber) stop codon. Although this motif produces a codon distribution as equitable as available with standard methods of oligonucleotide synthesis, it results in a bias against peptides containing one-codon residues. For example, a complete collection of hexacodons contains one sequence encoding each peptide made up of only one-codon amino acids, but contains 729 ($3^6$) sequences encoding each peptide with three-codon amino acids.

An alternate approach that minimizes the bias against one-codon residues involves the synthesis of 20 activated trinucleotides, each representing the codon for one of the 20 genetically encoded amino acids. These trinucleotides are synthesized by conventional means, removed from the support with the base and 5-OH-protecting groups intact, and activated by the addition of 3'-O-phosphoramidite (and phosphate protection with beta-cyanoethyl groups) by the method used for the activation of mononucleosides, as generally described in McBride and Caruthers, *Tetr. Letters* 22, 245 (1983), which is incorporated herein by reference.

Degenerate "oligocodons" are prepared using these trimers as building blocks. The trimers are mixed at the desired molar ratios and installed in the synthesizer. The ratios will usually be approximately equimolar, but may be a controlled unequal ratio to obtain the over- to under-representation of certain amino acids coded for by the degenerate oligonucleotide collection. The condensation of the trimers to form the oligocodons is done essentially as described for conventional synthesis employing activated mononucleosides as building blocks. See generally, Atkinson and Smith, *Oligonucleotide Synthesis* (M. J. Gait, ed.), pp. 35–82 (1984). This procedure generates a population of oligonucleotides for cloning that is capable of encoding an equal distribution (or a controlled unequal distribution) of the possible peptide sequences. This approach may be especially useful in generating longer peptide sequences, because the range of bias produced by the $(NNK)_x$ motif increases by three-fold with each additional amino acid residue.

When the codon motif is $(NNK)_x$ as defined above, and when x equals 8, there are $2.6 \times 10^{10}$ possible octapeptides. A library containing most of the octapeptides may be produced, but a sampling of the octapeptides may be more conveniently constructed by making only a subset library using about 0.1%, and up to as much as 1%, 5%, or 10%, of the possible sequences, which subset of recombinant vectors is then screened. As the library size increases, smaller percentages are acceptable. If desired, to extend the diversity of a subset library the recovered vector subset may be subjected to mutagenesis and then subjected to subsequent rounds of screening. This mutagenesis step may be accomplished in two general ways: the variable region of the recovered phage may be mutagenized or additional variable amino acids may be added to the regions adjoining the initial variable sequences.

The process of constructing a random peptide encoding oligonucleotide is described in Example 2, below. In brief, a library can be constructed in pMC5 using the half-site cloning strategy of Cwirla et al., supra. A random dodecamer peptide sequence, connected to the C-terminus of the lac repressor through a linker peptide GADGGA (GADGA [SEQ. ID NO.:65]) would also be an acceptable linker), can be specified by a degenerate oligonucleotide population containing twelve codons of the form NNK, where N is any base, and K is G or T. Transformation of *E. coli* strain MC1061 using 4 µg of pMC5 ligated to a four fold molar excess of annealed oligonucleotides yielded a test library of $5.5 \times 10^8$ independent clones.

Once the library is constructed, host cells are transformed with the library vectors. The successful transformants are typically selected by growth in a selective medium or under selective conditions, e.g., an appropriate antibiotic, which, in the case of plasmid pMC5 derivatives, is preferably ampicillin. This selection may be done on solid or in liquid growth medium. For growth on solid medium, the cells are grown at a high density ($^{-}10^8$ to $10^9$ transformants per $m^2$) on a large surface of, for example, L-agar containing the selective antibiotic to form essentially a confluent lawn. For growth in liquid culture, cells may be grown in L-broth (with antibiotic selection) through about 10 or more doublings. Growth in liquid culture may be more convenient because of the size of the libraries, while growth on solid media likely provides less chance of bias during the amplification process.

For best results with the present method, one should control the ratio of fusion proteins to vectors so that vectors are saturated with fusion proteins, without a vast excess of fusion protein. Too little fusion protein could result in vectors with free binding sites that might be filled by fusion protein from other cells in the population during cell lysis, thus breaking the connection between the genetic information and the peptide ligand. Too much fusion protein could lead to titration of available receptor sites during panning by fusion protein molecules not bound to plasmid. To control this ratio, one can use any of a variety of origin of replication sequences to control vector number and/or an inducible promoter, such as any of the promoters selected from the group consisting of the araB, lambda pL, (which can be either nalidixic acid or heat inducible or both), trp, lac, T7, T3, and tac or trc (these latter two are trp/lac hybrids) promoters to control fusion protein number. A regulated promoter is also useful to limit the amount of time that the peptide ligands are exposed to cellular proteases. By inducing the promoter a short time before lysing the cells containing a library, one can minimize the time during which proteases act.

The araB promoter normally drives expression of the enzymes of the *E. coli* araBAD operon, which are involved in the catabolism of L-arabinose. The araB promoter is regulated both positively and negatively, depending on the presence of L-arabinose in the growth medium, by the araC protein. This promoter can be catabolite repressed by adding glucose to the growth medium and induced by adding L-arabinose to the medium. Plasmid pMC5 encodes and can drive expression of the araC protein (see Lee, *The Operon* (Miller and Reznikoff, eds., Cold Spring Harbor Laboratory), pp. 389–409 (1980)). The araB promoter is also regulated by the CAP protein, an activator involved in the *E. coli* system of catabolite repression.

The expression level of the lacI fusion gene under the control of the araB promoter in plasmid pMC5 can be controlled over a very wide range through changes in the growth medium. One can construct a vector to measure expression of a fusion protein encoding gene to determine the growth conditions needed to maintain an acceptable ratio of repressors to vectors. Plasmid pMC3 is such a vector and can be constructed by attaching an oligonucleotide that encodes a short peptide linker (GADGA [SEQ. ID NO.:65]) followed by dynorphin B (YGGFLRRQFKVVT [SEQ. ID NO.7]) to the lacI gene in plasmid pMC5. Monoclonal antibody D32.39 binds to dynorphin B, a 13 amino acid opioid peptide (see Barrett and Goldstein, *Neuropeptides* 6, 113–120 (1895), incorporated herein by reference). These same reagents, plasmids pMC3 and pMC5 and receptor D32.39, provide a test receptor and positive and negative controls for use in panning experiments, described below. Growth of *E. coli* transformants harboring plasmid pMC3 in LB broth (10 g of tryptone, 5 g of NaCl, and 5 g of yeast extract per liter) allowed detection in a Western blot of a faint band of the expected molecular weight, while addition of 0.2% glucose rendered this band undetectable. Growth in LB plus 0.2% L-arabinose led to the production of a very heavy band on a stained gel, representing greater than 25% of the total cell protein.

To prevent overproduction of the fusion protein encoded by a plasmid pMC5 derivative (or any other vector of the present invention that has an inducible promoter), one can grow the transformants first under non-inducing conditions (to minimize exposure of the fusion protein to cellular proteases and to minimize exposure of the cell to the possibly deleterious effects of the fusion protein) and then under "partial induction" conditions. For the araB promoter, partial induction can be achieved with as little as $3.3 \times 10^{-5}\%$ of L-arabinose (as demonstrated by increased repression in the assay described below). A preferred way to achieve partial induction consists of growing the cells in 0.1% glucose until about 30 min. before the cells are harvested; then, 0.2 to 0.5% L-arabinose is added to the culture to induce expression of the fusion protein. Other methods to express the protein controllably are available.

One can estimate the lacI expression level necessary to fill the available binding sites in a typical plasmid pMC5 derivative by observing the behavior of strain ARI 20 (lacI$^-$ lacZYA$^+$) transformed with pMC3 or pMC5 (encoding only the linker peptide GADGA [SEQ. ID NO.:65]). Because the lacO sites in plasmids pMC3 and pMC5 have higher affinity than those in the lacZYA operon, the available repressor should fill the plasmid sites first. Substantial repression of lacZYA should be observed only if there is an excess of repressor beyond the amount needed to fill the plasmid sites. As shown by color level on X-gal indicator plates and direct assays of β-galactosidase (see Miller, *Experiments in Molecular Genetics* (Cold Spring Harbor Laboratory, Cold Spring Harbor, N.Y. (1972)), incorporated herein by reference), the amount of repressor produced by pMC5 is sufficient to fill the lacO sites and repress greater than 200 fold lacZYA in ARI 20 host cells during growth in normal LB medium (2.4 units compared to 500 units from ARI 20 transformed with vector pBAD18, which has no lacI). The repressor encoded by pMC3 was partially inactivated by the addition of the dynorphin B tail, allowing about 10 fold higher expression of lacZYA (37 units). Because of the apparent excess production of repressor under these conditions, LB is a preferred medium for expressing similar fusion proteins of the invention.

At some point during the growth of the transformants, the fusion protein will be expressed. Because the random peptide vector also contains DNA binding sites for the DNA binding protein, fusion proteins will bind to the vectors that encode them. After these complexes form, the cells containing a library are lysed, and the complexes are partially purified away from cell debris. Following cell lysis, one should avoid cross reaction between unbound fusion proteins of one cell with heterologous DNA molecules of another cell. The presence of high concentrations of the DNA binding site for the DNA binding protein will minimize this type of cross reaction. Thus, for the lac system, one can synthesize a DNA duplex encoding the lacO or a mutated lacO sequence for addition to the cell lysis solution. The compound ONPF, as well as lactose, is known to strengthen the binding of the lac repressor to lacO, so one can also, or alternatively, add ONPF or lactose to the cell lysis solution to minimize this type of cross reaction.

After cell lysis, in a process called panning, plasmid-peptide complexes that bind specifically to immobilized receptors are separated from nonbinding complexes, which are washed away. Bulk DNA can be induced during the lysis and panning steps to compete for non-specific binding sites and to lower the background of non-receptor-specific binding to the immobilized receptor. A variety of washing procedures can be used to enrich for retention of molecules with desired affinity ranges. For affinity enrichment of desired clones, from about $10^2$ to $10^6$ library equivalents (a library equivalent is one of each recombinant; $10^4$ equivalents of a library of $10^9$ members is $10^{13}$ vectors), but typically $10^3$ to $10^4$ library equivalents, are incubated with a receptor (or portion thereof) for which a desired peptide ligand is desired. The receptor is in one of several forms appropriate for affinity enrichment schemes. In one example the receptor is immobilized on a surface or particle, and the library is then panned on the immobilized receptor generally according to the procedure described below.

A second example of receptor presentation is receptor attached to a recognizable ligand (which may be attached via a spacer). A specific example of such a ligand is biotin. The receptor, so modified, is incubated with the library, and binding occurs with both reactants in solution. The resulting complexes are then bound to streptavidin (or avidin) through the biotin moiety. See PCT patent publication No. 91/07087. The streptavidin may be immobilized on a surface such as a plastic plate or on particles, in which case the complexes (vector/DNA binding protein/peptide/receptor/biotin/streptavidin) are physically retained; or the streptavidin may be labelled, with a fluorophore, for example, to tag the active fusion protein for detection and/or isolation by sorting procedures, e.g., on a fluorescence-activated cell sorter.

Vectors that express peptides without the desired specificity are removed by washing. The degree and stringency of washing required will be determined for each receptor/peptide of interest. A certain degree of control can be exerted over the binding characteristics of the peptides recovered by adjusting the conditions of the binding incubation and the subsequent washing. The temperature, pH, ionic strength, divalent cation concentration, and the volume and duration of the washing will select for peptides within particular ranges of affinity for the receptor. Selection based on slow dissociation rate, which is usually predictive of high affinity, is the most practical route. This may be done either by continued incubation in the presence of a saturating amount of free ligand, or by increasing the volume, number, and length of the washes. In each case, the rebinding of dissociated peptide-vector is prevented, and with increasing time, peptide-vectors of higher and higher affinity are recovered. Additional modifications of the binding and washing procedures may be applied to find peptides that bind receptors under special conditions.

Although the screening method is highly specific, the procedure generally does not discriminate between peptides of modest affinity (micromolar dissociation constants) and those of high affinity (nanomolar dissociation constants or greater). The ability to select peptides with relatively low affinity may be the result of multivalent interaction between a vector/fusion protein complex and a receptor. For instance, when the receptor is an IgG antibody, each complex may bind to more than one antibody binding site, either by a single complex binding through the multiple peptides displayed to both sites of a single IgG molecule or by forming a network of complex-IgG. Multivalent interaction produces a high avidity and tenacious adherence of the vector during washing. Multivalent interactions can be mimicked by using a high density of immobilized monovalent receptor.

To enrich for the highest affinity peptide ligands, a substantially monovalent interaction between vector and the receptor (typically immobilized on a solid phase) may be appropriate. The screening (selection) with substantially monovalent interaction can be repeated as part of additional rounds of amplification and selection of vectors. Monovalent interactions may be achieved by employing low concentrations of receptor, such as the Fab binding fragment of an antibody molecule.

A strategy employing a combination of conditions favoring multivalent or monovalent interactions can be used to advantage in producing new peptide ligands for receptor molecules. By conducting the first rounds of screening under conditions to promote multivalent interactions, one can then use high stringency washing to reduce greatly the background of non-specifically bound vectors. This high avidity step may select a large pool of peptides with a wide range of affinities, including those with relatively low affinity. Subsequent screening under conditions favoring increasingly monovalent interactions and isolation of plasmid complexes based on a slow dissociation rate may then allow the identification of the highest affinity peptides.

After washing the receptor-fusion protein-vector complexes to select for peptides of the desired affinity, the vector DNA is then released from bound complexes by, for example, treatment with high salt or extraction with phenol, or both. For the lac system, one can use IPTG, a compound known to decrease the stability of the lac repressor-lacO complex, to dissociate the plasmid from the fusion protein. In a preferred embodiment, the elution buffer is composed of 1 mM IPTG, 10 µg/ml of a double-stranded oligonucleotide that contains lacOs, and 0.2M KCl. Once released from bound complexes, the plasmids are reintroduced into $E.\ coli$ by transformation. Because of the high efficiency, the preferred method of transformation is electroporation. Using this new population of transformants, one can repeat additional cycles of panning to increase the proportion of peptides in the population that are specific for the receptor. The structure of the binding peptides can then be determined by sequencing the 3' region of the lacI fusion gene.

As noted above, antibody D32.39 and the pMC3 complex serves as a receptor-ligand positive control in panning experiments to determine ability to recover plasmids based on the sequence of the fusion peptide. Useful negative controls are pMC5, which encodes only the linker fusion peptide (GADGA [SEQ. ID NO.:65]), and pMC1, which encodes the dynorphin B peptide, but lacks the lacO sequences carried by pMC3 and pMC5. Lysates of $E.\ coli$ strains carrying each plasmid were panned on D32.39 immobilized on polystyrene petri dishes. After washing, plasmids were recovered from complexes bound to the plates by phenol extraction, followed by transformation of $E.\ coli$.

The results with pure lysates demonstrated about 100 fold more transformants recovered from pMC3 lysates as compared to the negative controls. The results with mixed lysates revealed enrichment of pMC3 versus controls among the population of recovered plasmids. The results with cells that were mixed before lysis yielded similar results. These results show that the plasmid-lacI-peptide complexes were sufficiently stable to allow enrichment of plasmids on the basis of the peptide the plasmids encode.

The random dodecapeptide library in pMC5 described above was used in the screening method of the invention to identify vectors that encode a fusion protein that comprised a peptide that would bind to D32.39 antibody coupled to sheep antimouse antibody coated magnetic beads. The number of complexes added to the beads at each round of panning yielded the equivalent of $10^{10}$ to $10^{11}$ transformants (see Example 3). After panning, the recovered plasmids yielded transformants ranging in number from about $10^8$ in early rounds to almost $10^{11}$ in the fourth and final round. Compared to the number of transformants from antibody panned complexes, panning against unmodified polystyrene beads produced orders of magnitude fewer transformants.

The above results demonstrate that the DNA binding activity of lac repressor can act as a link between random peptides and the genetic material encoding them and so serve as the base on which to construct large peptide ligand libraries that can be efficiently screened. In the screening process, plasmid-repressor-peptide complexes are isolated by panning on immobilized receptor, the plasmids are amplified after transformation of E. coli, and the procedure is repeated to enrich for plasmids encoding peptides specific for the receptor. The repressor binds to the library plasmid with sufficient avidity to allow panning of the library on immobilized receptor without problematic levels of dissociation. This system can be used to identify a series of related peptides that bind to a monoclonal antibody whose epitope has not been characterized and to identify peptide ligands for other receptors.

Once a peptide ligand of interest has been identified, a variety of techniques can be used to diversify a peptide library to construct ligands with improved properties. In one approach, the positive vectors (those identified in an early round of panning) are sequenced to determine the identity of the active peptides. Oligonucleotides are then synthesized based on these peptide sequences, employing all bases at each step at concentrations designed to produce slight variations of the primary oligonucleotide sequences. This mixture of (slightly) degenerate oligonucleotides is then cloned into the random peptide library expression vector as described herein. This method produces systematic, controlled variations of the starting peptide sequences but requires, however, that individual positive vectors be sequenced before mutagenesis. This method is useful for expanding the diversity of small numbers of recovered vectors.

Another technique for diversifying a selected peptide involves the subtle misincorporation of nucleotide changes in the coding sequence for the peptide through the use of the polymerase chain reaction (PCR) under low fidelity conditions. A protocol described in Leung et al., Technique 1, 11-15 (1989), utilizes altered ratios of nucleotides and the addition of manganese ions to produce a 2% mutation frequency.

Yet another approach for diversifying a selected random peptide vector involves the mutagenesis of a pool, or subset, of recovered vectors. Recombinant host cells transformed with vectors recovered from panning are pooled and isolated. The vector DNA is mutagenized by treating the cells with, e.g., nitrous acid, formic acid, hydrazine, or by use of a mutator strain as described below. These treatments produce a variety of mutations in the vector DNA. The segment containing the sequence encoding the variable peptide can optionally be isolated by cutting with restriction nuclease(s) specific for sites flanking the variable region and then recloned into undamaged vector DNA. Alternatively, the mutagenized vectors can be used without recloning of the mutagenized random peptide coding sequence.

In the second general approach for diversifying a set of peptide ligands, that of adding additional amino acids to a peptide or peptides found to be active, a variety of methods are available. In one, the sequences of peptides selected in early panning are determined individually and new oligonucleotides, incorporating all or part of the determined sequence and an adjoining degenerate sequence, are synthesized. These are then cloned to produce a secondary library.

In another approach that adds a second variable region to a pool of random peptide expression vectors, a restriction site is installed next to the primary variable region. Preferably, the enzyme should cut outside of its recognition sequence, such as BspMI, which cuts leaving a four base 5' overhang, four bases to the 3' side of the recognition site. Thus, the recognition site may be placed four bases from the primary degenerate region. To insert a second variable region, a degenerately synthesized oligonucleotide is then ligated into this site to produce a second variable region juxtaposed to the primary variable region. This secondary library is then amplified and screened as before.

While in some instances it may be appropriate to synthesize peptides having contiguous variable regions to bind certain receptors, in other cases it may be desirable to provide peptides having two or more regions of diversity separated by spacer residues. For example, the variable regions may be separated by spacers that allow the diversity domains of the peptides to be presented to the receptor in different ways. The distance between variable regions may be as little as one residue or as many as five to ten to up to about 100 residues. For probing a large binding site, one may construct variable regions separated by a spacer containing 20 to 30 amino acids. The number of spacer residues, when present, will preferably be at least two to three or more but usually will be less than eight to ten. An oligonucleotide library having variable domains separated by spacers can be represented by the formula: $(NNK)_y$-$(abc)_n$-$(NNK)_z$, where N and K are as defined previously (note that S as defined previously may be substituted for K); y+z is equal to about 5, 6, 7, 8, or more; a, b and c represent the same or different nucleotides comprising a codon encoding spacer amino acids; and n is up to about 20 to 30 codons or more.

The spacer residues may be somewhat flexible, comprising oligoglycine, for example, to provide the diversity domains of the library with the ability to interact with sites in a large binding site relatively unconstrained by attachment to the DNA binding protein. Rigid spacers, such as, e.g., oligoproline, may also be inserted separately or in combination with other spacers, including glycine residues. The variable domains can be close to one another with a spacer serving to orient the one variable domain with respect to the other, such as by employing a turn between the two sequences, as might be provided by a spacer of the sequence Gly-Pro-Gly, for example. To add stability to such a turn, it may be desirable or necessary to add Cys residues at either or both ends of each variable region. The Cys residues would then form disulfide bridges to hold the variable regions together in a loop, and in this fashion may also serve to mimic a cyclic peptide. Of course, those skilled in the art will appreciate that various other types of covalent linkages for cyclization may also be accomplished.

The spacer residues described above can also be encoded on either or both ends of the variable nucleotide region. For instance, a cyclic peptide coding sequence can be made without an intervening spacer by having a Cys codon on both ends of the random peptide coding sequence. As above, flexible spacers, e.g., oligoglycine, may facilitate interaction of the random peptide with the selected receptors. Alternatively, rigid spacers may allow the peptide to be presented as if on the end of a rigid arm, where the number of residues, e.g., Pro, determines not only the length of the arm but also the direction for the arm in which the peptide is oriented. Hydrophilic spacers, made up of charged and/or uncharged hydrophilic amino acids, (e.g., Thr, His, Asn, Gln, Arg, Glu, Asp, Met, Lys, etc.), or hydrophobic spacers made up of hydrophobic amino acids (e.g., Phe, Leu, Ile, Gly, Val, Ala, etc.) may be used to present the peptides to binding sites with a variety of local environments.

The present invention can be used to construct improved spacer molecules. For example, one can construct a random peptide library that encodes a DNA binding protein, such as the lac repressor or a cysteine depleted lac repressor (described below), a random peptide of formula $NNK_5$ (sequences up to and including $NNK_{10}$ or $NNK_{15}$ could also be used), and a peptide ligand of known specificity. One would then screen the library for improved binding of the peptide ligand to the receptor specific for the ligand using the method of the present invention; fusion proteins that exhibit improved specificity would be isolated together with the vector that encodes them, and the vector would be sequenced to determine the structure of the spacer responsible for the improved binding.

Unless modified during or after synthesis by the translation machinery, recombinant peptide libraries consist of sequences of the 20 normal L-amino acids. While the available structural diversity for such a library is large, additional diversity can be introduced by a variety of means, such as chemical modifications of the amino acids. For example, as one source of added diversity a peptide library of the invention can be subjected to carboxy terminal amidation. Carboxy terminal amidation is necessary to the activity of many naturally occurring bioactive peptides. This modification occurs in vivo through cleavage of the N-C bond of a carboxy terminal Gly residue in a two-step reaction catalyzed by the enzymes peptidylglycine alpha-amidation monooxygenase (PAM) and hydroxyglycine aminotransferase (HGAT). See Eipper et al., *J. Biol. Chem.* 266, 7827–7833 (1991); Mizuno et al., *Biochem. Biophys. Res. Comm.* 137(3), 984–991 (1986); Murthy et al., *J. Biol. Chem.* 261(4), 1815–1822 (1986); Katopodis et al., *Biochemistry* 29, 6115–6120 (1990); and Young and Tamburini, *J. Am. Chem. Soc.* 111, 1933–1934 (1989), each of which are incorporated herein by reference.

Amidation can be performed by treatment with enzymes, such as PAM and HGAT, in vivo or in vitro, and under conditions conducive to maintaining the structural integrity of the fusion protein/vector complex. In a random peptide library of the present invention, amidation will occur on a library subset, i.e., those peptides having a carboxy terminal Gly. A library of peptides designed for amidation can be constructed by introducing a Gly codon at the end of the variable region domain of the library. After amidation, an enriched library serves as a particularly efficient source of ligands for receptors that preferentially bind amidated peptides. Many of the C-terminus amidated bioactive peptides are processed from larger pro-hormones, where the amidated peptide is flanked at its C-terminus by the sequence -Gly-Lys-Arg-X . . . (SEQ. ID NO. 67) (where X is any amino acid). Oligonucleotides encoding the sequence -Gly-Lys-Arg-X-Stop (SEQ. ID NO. 67) can be placed at the 3' end of the variable oligonucleotide region. When expressed, the Gly-Lys-Arg-X (SEQ. ID NO. 67) is removed by in vivo or in vitro enzymatic treatment, and the peptide library is carboxy terminal amidated as described above.

Conditions for C-terminal amidation of the libraries of the invention were developed using a model system that employed an antibody specific for the amidated C-terminus of the peptide cholecystokinin (CCK). The reaction conditions to make the peptide a-amidating monooxygenase (PAM) enzyme active when used to amidate the libraries were developed using an $^{125}I$ labeled small peptide substrate and an ELISA with a positive control glycine extended CCK octamer peptide fused to the lac repressor. The *E. coli* strain used in the experiment carried plasmid pJS129, which encodes the cysteine free lac repressor (described below) fused to the CCK substrate peptide (DYMGWMDFG). A panning lysate was made from this strain using the standard panning protocol (see Example 6). After concentrating the column fractions in a Centriprep 100, four samples were prepared, each containing 0.25 ml of lysate and 0.25 ml of 2×PAM buffer (prepared by mixing 0.2 ml of 1M HEPES, pH 7.4, 0.9 ml of 20% lactose, 3.65 ml of $H_2O$, 0.1 ml of a solution composed of 20 mg/ml catalase, 16.6 µl of 6M NaI, and 150 µl of 0.1M ascorbic acid). PAM enzyme was added to the tubes and incubated at 37° C. for 30 minutes. Then, 120 µl of 5% BSA in HEKL buffer and 6 µl of herring DNA were added to each tube; the contents of each tube were then added to 6 microtiter wells that had been coated with 2 µg/well anti-CCK antibody and blocked with BSA. The microtiter plate was agitated at 4° C. for 150 minutes, washed 5× with cold HEKL, washed for 10 minutes with a solution composed of HEKL, 1% BSA, and 0.1 mg/ml herring DNA, and washed again 5× with cold HEKL. The plasmids were eluted using the standard protocol and used to transform *E. coli* host cells. The results showed a dramatic increase in the recovery of plasmid transformants with increasing amounts of PAM enzyme, demonstrating that the amidation reaction worked.

Other modifications found in naturally occurring peptides and proteins can be introduced into the libraries to provide additional diversity and to contribute to a desired biological activity. For example, the variable region library can be provided with codons that code for amino acid residues involved in phosphorylation, glycosylation, sulfation, isoprenylation (or the addition of other lipids), etc. Modifications not catalyzed by naturally occurring enzymes can be introduced by chemical means (under relatively mild conditions) or through the action of, e.g., catalytic antibodies and the like. In most cases, an efficient strategy for library construction involves specifying the enzyme (or chemical) substrate recognition site within or adjacent to the variable nucleotide region of the library so that most members of the library are modified. The substrate recognition site added can be simply a single residue (e.g., serine for phosphorylation) or a complex consensus sequence, as desired.

Conformational constraints, or scaffolding, can also be introduced into the structure of the peptide libraries. A number of motifs from known protein and peptide structures can be adapted for this purpose. The method involves introducing nucleotide sequences that code for conserved structural residues into or adjacent to the variable nucleotide region so as to contribute to the desired peptide structure. Positions nonessential to the structure are allowed to vary.

A degenerate peptide library as described herein can incorporate the conserved frameworks to produce and/or identify members of families of bioactive peptides or their binding receptor elements. Several families of bioactive peptides are related by a secondary structure that results in a conserved "framework," which in some cases is a pair of cysteines that flank a string of variable residues. This results in the display of the variable residues in a loop closed by a disulfide bond, as discussed above.

In some cases, a more complex framework that contributes to the bioactivity of the peptides is shared among members of a peptide family. An example of this class is the conotoxins: peptide toxins of 10 to 30 amino acids produced by venomous molluscs known as predatory cone snails. The conotoxin peptides generally possess a high density of disulfide crosslinking. Of those that are highly crosslinked, most belong to two groups, mu and omega, that have conserved primary frameworks as follows (C is Cys):

| mu | CC....C....C....CC; and |
|---|---|
| omega | C....C....CC....C....C |

The number of residues flanked by each pair of Cys residues varies from 2 to 6 in the peptides reported to date. The side chains of the residues that flank the Cys residues are apparently not conserved in peptides with different specificity, as in peptides from different species with similar or identical specificities. Thus, the conotoxins have exploited a conserved, densely crosslinked motif as a framework for hypervariable regions to produce a huge array of peptides with many different pharmacological effects.

The mu and omega classes (with 6 Cys residues) have 15 possible combinations of disulfide bonds. Usually only one of these conformations is the active ("correct") form. The correct folding of the peptides may be directed by a conserved 40 residue peptide that is cleaved from the N-terminus of the conopeptide to produce the small, mature bioactive peptides that appear in the venom.

With 2 to 6 variable residues between each pair of Cys residues, there are 125 ($5^3$) possible framework arrangements for the mu class (2,2,2, to 6,6,6), and 625 ($5^4$) possible for the omega class (2,2,2,2 to 6,6,6,6). Randomizing the identity of the residues within each framework produces $10^{10}$ to $>10^{30}$ peptides. "Cono-like" peptide libraries are constructed having a conserved disulfide framework, varied numbers of residues in each hypervariable region, and varied identity of those residues. Thus, a sequence for the structural framework for use in the present invention comprises Cys-Cys-Y-Cys-Y-Cys-Cys, or Cys-Y-Cys-Y-Cys-Cys-Y-Cys-Y-Cys, where Y is $(NNK)_x$ or $(NNS)_x$; N is A, C, G or T; K is G or T; S is G or C; and x is from 2 to 6.

Framework structures that require the formation of one or more disulfide bonds under oxidizing conditions may create problems with respect to the natural lac repressor, which has 3 cysteine residues. All 3 of these residues, however, can be changed to other amino acids without a serious effect on the function of the molecule (see Kleina and Miller, supra). Plasmid pJS123 is derived from plasmid pMC5 by site specific mutagenesis and encodes a lac repressor identical to the lac repressor encoded on plasmid pMC5, except the cysteine codon at position 107 has been changed to an serine codon; the cysteine codon at position 140 has been changed to an alanine codon (alanine works better than serine at this position); and the cysteine codon at position 281 has been changed to a serine codon. Plasmid pJS123 (available in strain ARI 161 from the American Type Culture Collection under the accession number ATCC No. 68819) is therefore preferred for constructing random peptide libraries involving cysteine-linked framework structures.

The lac repressor coding sequence in plasmid pJS123 can be subjected to mutagenesis to improve the binding of the mutant coding sequence with lacO type sequences. A preferred method for performing this mutagenesis involves the construction of a coding sequence in plasmid pJS123 that encodes a fusion protein comprised of the cysteine depleted lac repressor, a spacer peptide, and a peptide ligand of known specificity. The resulting vector is subjected to mutagenesis by any of a variety of methods; a preferred method involves transformation of an E. coli mutator strain such as mutD5 (see Schaaper, Proc. Natl. Acad. Sci. USA 85, 8126–8130 (1988), incorporated herein by reference) and culture of the transformants to produce the fusion protein encoded by the vector. The fusion proteins are screened by the present method to find vectors that have been mutated to increase the binding affinity of the cysteine depleted lac repressor to the lacO sequence. One could combine this method with the method of constructing improved spacers, described above, to select for an improved cysteine depleted lac repressor-peptide spacer molecule.

In such a fashion, plasmid pJS123 was modified to create plasmid pJS128, which was then introduced into a mutD mutator strain. Oligonucleotides were then cloned into the mutagenized vector to encode a D32.39 epitope joined to repressor via a random region of 5, 10, or 15 amino acids. This library was panned on D32.39 antibody for 5 rounds under increasingly stringent conditions. Individual clones were selected from the population of plasmids surviving after the fifth round and tested by a variety of assays. These assays included: (1) tests for ability to repress the chromosomal lac operon (a test of DNA binding affinity); (2) tests for plasmid copy number; (3) ELISA with D32.39 antibody to test for display of the peptide epitope; and (4) tests of plasmid recovery during panning. Several of these plasmids were sequenced in the random tail region to determine the structure of the linker peptide. A series of subcloning experiments were also conducted to determine regions of the plasmids that determined the observable properties of the plasmids. Finally, plasmids carrying a higher copy number replication origin and encoding one of the linker regions were constructed and sequenced to ascertain that no base changes in the cysteine free repressor gene, as compared to the starting plasmid, were introduced. The linker tail of this plasmid and the cloning strategy for random libraries is shown in FIG. 4. Two versions of the vector were constructed, one with the cysteine-free lac repressor gene (ARI246/pJS141; ATCC No. 69088) and one with the wild-type lac repressor gene (ARI280/pJS142; ATCC No. 69087). (These cell lines will be maintained at an authorized depository and replaced in the event of mutation, nonviability or destruction for a period of at least five years after the most recent request for release of a sample was received by the depository, for a period of at least thirty years after the date of the deposit, or during the enforceable life of the related patent, whichever period is longest. All restrictions on the availability to the public of these cell lines will be irrevocably removed upon the issuance of a patent from the above-captioned application.)

ARI246 has the genotype E. coli B lon-11 sulA1 hsdR17 Δ(ompT-fepC) ΔclpA319::kan lacI42::Tn10 lacZU118. The lon-11, Δ(ompT-fepC), and ΔclpA319::kan mutations destroy three genes involved in proteolysis, so this strain should allow greater diversity of peptides to be expressed on the library particles. The sulA1 mutation suppresses the filamentation phenotype caused by the lon-11 allele. The hsdR17 mutation destroys the restriction system to allow more efficient transformation of unmodified DNA. The lacI42::Tn10 mutation eliminates expression of the chromosomal lac repressor gene to prevent competition of wild-type repressor for binding sites on the library plasmids. The lacZU118 allele stops expression of β-galactosidase, which would otherwise be constitutive in the lacI42::Tn10 background, leading to unnecessary use of cell resources and reducing growth rates. *E. coli* B cells grow more quickly than K12 cells and yields excellent electrocompetent cells for transformation. Transformation frequencies of around $5 \times 10^{10}$ tf/µg of Bluescript plasmid DNA can be frequently observed with ARI246 cells. ARI280 has the same genotype as ARI246, except that the lacI mutation has been converted to a deletion by selecting for loss of the Tn10 insertion, and a recA::cat mutation has been introduced. The recA::cat mutation is useful to prevent homologous recombination between plasmids. As a consequence, the library plasmids exist more frequently as monomers, rather than multimeric forms that can be observed in ARI246. The monomers are better for two reasons: monomers reduce the valency of peptides per library particle, allowing more stringent selection for higher affinity peptide ligands; and growth as monomers increases the number of plasmids per amount of DNA, increasing the number of library equivalents that can be panned against receptors. The recA::cat mutation makes the strain less healthy, so growth rates are slower, and the transformation frequency is reduced to about $2 \times 10^{10}$ tf/µg.

Other changes can be introduced to provide residues that contribute to the peptide structure, around which the variable amino acids are encoded by the library members. For example, these residues can provide for alpha helices, a helix-turn-helix structure, four helix bundles, a beta-sheet, or other secondary or tertiary structural (framework or scaffolding) motifs. See U.S. Ser. No. 07/718,577, filed Jun. 20, 1991, incorporated herein by reference. DNA binding peptides, such as those that correspond to the transcriptional transactivators referred to as leucine zippers, can also be used as a framework, provided the DNA binding peptide is distinct from the DNA binding protein component of the fusion protein and the library vector does not contain the binding site for the DNA binding peptide. In these peptides, leucine residues are repeated every seven residues in the motifs, and the region is adjacent to an alpha helical region rich in lysines and arginines and characterized by a conserved helical face and a variable helical face.

Other specialized forms of structural constraints can also be used in the present invention. For example, certain serine proteases are inhibited by small proteins of conserved structure (e.g., pancreatic trypsin inhibitor). This conserved framework can incorporate degenerate regions as described herein to generate libraries for screening for novel protease inhibitors.

In another aspect related to frameworks for a peptide library, information from the structure of known ligands can be used to find new peptide ligands having features modified from those of the known ligand. In this embodiment, fragments of a gene encoding a known ligand, prepared by, e.g., limited DNAse digestion into pieces of 20 to 100 base pairs, are subcloned into a variable nucleotide region system as described herein either singly or in random combinations of several fragments. The fragment library is then screened in accordance with the procedures herein for binding to the receptor to identify small peptides capable of binding to the receptor and having characteristics which differ as desired from the parental peptide ligand. This method is useful for screening for any receptor-ligand interaction where one or both members are encoded by a gene, e.g., growth factors, hormones, cytokines and the like, such as insulin, interleukins, insulin-like growth factor, etc. In this embodiment of the invention, the peptide library can contain as few as 10 to 100 different members, although libraries of 1000 or more members will generally be used.

Thus, the present invention can be used to construct peptide ligands of great diversity. The novel features of the preferred embodiment of the invention, called "peptides on plasmids", in which the lac repressor is the DNA binding protein and a plasmid vector encodes the fusion protein, are distinct from those of the previously described phage libraries. The random peptides of the present libraries can be displayed with a free carboxy terminus instead of being displayed at the amino terminus or internal to the carrier protein and so add diversity to the peptide structures available for receptor binding. The presentation of peptide ligands at the carboxy terminus also facilitates amidation, as discussed above. This mode of display also ensures that stop codons in the degenerate region, which occur more often in longer degenerate oligonucleotides, shorten rather than destroy individual clones. The presence of stop codons in the random peptide coding sequence actually serves to create additional diversity, by creating peptides of differing lengths. The lac repressor fusions of the invention also allow the display of potential ligands with a wide range of sizes.

In addition, these lac repressor fusions are cytoplasmic proteins, unlike the phage fusions, which are exported to the periplasm. The use of both fusion methods increases total available peptide diversity, because the two types of libraries are exposed to different cellular compartments and so are exposed to different sets of *E. coli* proteases and to different reduction/oxidation environments. There is no need, however, for peptides fused to the lac repressor to be compatible with the protein export apparatus and the formation of an intact phage coat. The peptides need simply be compatible with the formation of at least a repressor dimer, which is the smallest form of the protein that can bind DNA (see Daly and Matthews, *Biochem.* 25, 5474–5478 (1986); and Kania and Brown, *Proc. Natl. Acad. Sci. USA* 73, 3529–3533 (1976)).

As in the phage system, the lac repressor fusion library displays multiple copies of the peptide on each library particle. Each repressor tetramer, in principle, displays four peptides that are available for binding to receptors. In addition, each plasmid monomer can bind up to two tetramers (if no loop is formed), and multimers of the plasmid can display higher multiples of two tetramers. This multivalent display allows the isolation of ligands with moderate affinity (micromolar $K_d$, see Cwirla et al., supra). For receptors with known, high affinity peptide ligands, these moderate affinity ligands can obscure the high affinity ones simply because of their greater numbers. This problem can be overcome by immobilizing monovalent receptors at low density, which allows high affinity (nanomolar $K_d$) ligands to be identified, as discussed above. For receptors whose normal ligands are not small peptides, however, this multivalency of display will be an advantage for identifying initial families of moderate affinity ligands, which can then be optimized by additional rounds of screening under monovalent conditions. The multivalency of ligand display therefore allows the isolation of peptides with a wide range of affinities, depending on the density of the receptor during the panning procedure.

Libraries of peptides produced and screened according to the present invention are particularly useful for mapping antibody epitopes. The ability to sample a large number of potential epitopes as described herein has clear advantages over the methods based on chemical synthesis now in use and described in, among others, Geysen et al., *J. Immunol. Meth.* 102, 259–274 (1987). In addition, these libraries are useful in providing new ligands for important binding molecules, such as hormone receptors, adhesion molecules, enzymes, and the like.

The present libraries can be generalized to allow the screening of a wide variety of peptide and protein ligands. In addition, the vectors are constructed so that screening of other ligands encoded by the plasmid is possible. For example, the system can be simply modified to allow screening of RNA ligands. A known RNA binding protein (e.g., a ribosomal protein) is fused to the DNA binding protein. A promoter elsewhere on the vector drives expression of an RNA molecule composed of the known binding site for the RNA binding protein followed by random sequence. The DNA-RNA binding fusion protein would link the genetic information of the vector with each member of a library of RNA ligands. These RNA ligands could then be screened by panning techniques.

Another large class of possible extensions to this technique is to use a modified version of the vector to isolate genes whose products modify peptides, proteins, or RNA in a desired fashion. This requires the availability of a receptor that binds specifically to the modified product. For the general case, a connection is made between the plasmid and the substrate peptide, protein, or RNA, as described above. The plasmid is then used as a cloning vector to make libraries of DNA or cDNA from a source with the potential to contain the desired modification gene (specific organisms, PCR amplified antibody genes, etc.) under the control of a promoter that functions in *E. coli*. Plasmids carrying the gene in question could then be isolated by panning lysates of the library with the receptor specific for the modified product.

For example, a gene encoding an enzyme that cleaves a particular amino acid sequence could be isolated from libraries of DNA from organisms that might have such a protease or from amplified antibody cDNA. An antibody for use as the receptor would first be made to the peptide that would remain after the desired cleavage reaction had taken place. Many such antibodies will not bind to that peptide unless it is exposed at the N- or C-terminus of the protein. The coding sequence for the uncleaved substrate sequence would be attached to the DNA binding protein coding sequence in a vector. This vector would be used to make an expression library from an appropriate source. Members of this library containing a gene that encoded an enzyme able to cleave the peptide would cleave only the peptide attached to the plasmid with that gene. Panning of lysates of the library would preferentially isolate those plasmids with active genes.

Selection of DNA Binding Proteins by Forced Evolution

Although some DNA binding proteins for use in the invention are obtained directly from the repertoire of natural DNA binding proteins, other DNA binding proteins are selected by a process termed forced evolution. Forced evolution selects a DNA binding protein optimal for use in the peptides on plasmid screening methods described elsewhere in the specification. The functional properties that allow a DNA binding protein to survive the forced evolution process are the very same properties that confer optimum capacity to screen peptides in the peptides on plasmids method. Thus, the forced evolution process does not require prior knowledge of the binding mechanism of a DNA binding protein or prior definition of criteria (e.g., dissociation half-life, conformation) on which the efficacy of a DNA binding protein in the peptides on plasmids method is founded.

The method for performing forced evolution of a DNA binding protein is closely analogous to the methods of screening peptides on plasmids. The main difference between screening peptides on plasmids and forced evolution lies in whether the peptide component or the DNA binding component of a fusion protein is varied in different members of a library. In the peptides on plasmid method, the DNA binding protein is constant and the peptide moiety varies in different members of the library. The methods select a peptide with specific affinity for a receptor.

In the forced evolution method, the peptide is constant between different members of a library, and the DNA binding protein varies between members. As in the peptides on plasmids method, cells are transformed with libraries of vectors encoding fusion proteins. The fusion proteins comprise a potential DNA binding protein fused to the constant peptide. The cells are cultured under conditions in which the fusion proteins are expressed. If a fusion protein comprises a potential DNA binding protein that in fact has an affinity for the vector encoding it, the fusion protein binds to the vector to form a complex. The cell are lysed releasing complexes.

Complexes are screened by affinity purification on a receptor known to bind the peptide present in all of the complexes. Vectors are purified from complexes binding to the receptor via the peptide, amplified (e.g., by retransformation or PCR) and sequenced to reveal the identity of DNA binding proteins that have survived the selection process. To have survived the selection process, a DNA binding protein must have two properties: (1) capacity to remain complexed with the vector encoding it throughout the screening process; and (2) capacity to display the peptide with a conformation suitable for interaction with its receptor. These are the same properties that make a DNA binding protein useful for displaying a peptide in the peptides on plasmids method.

(1) Sources of Potential DNA Binding Proteins

The oligonucleotides encoding the potential DNA binding proteins can derive from a number of sources. Often, one starts with a natural DNA binding protein, in which case, the different potential DNA binding proteins represent variants of the natural DNA binding protein. Variants of a natural DNA binding protein can be produced by PCR mutagenesis of a DNA sequence encoding the protein. PCR mutagenesis can result in a low rate of mutagenesis at any position of the coding sequence. Thus, typically, each potential DNA binding protein shows a high degree of sequence identity (e.g., at least 95 or 98% sequence identity) with the natural protein, but the collective library include variants at all or nearly all of the positions in the protein. PCR mutagenesis is particularly suitable for natural DNA binding proteins which have not been extensively characterized, and for which there is little information about which amino acid residues are critical for binding. For other DNA binding proteins, such as lacI, for which prior studies have already identified certain positions as being important for binding, mutagenesis can be focussed on these positions. For example, the coding sequence of the natural protein can be synthesized on a DNA synthesizer, but with the introduction of randomized codons at the critical loci for binding.

The methods can screen multiple natural DNA binding proteins, or variants thereof, simultaneously. The methods can also screen potential binding proteins containing repeated copies of a natural binding domain or binding domains obtained from more than one natural protein. The potential DNA binding proteins can also be variants of a consensus DNA binding protein sequence or any theoretical DNA sequence thought to have DNA binding properties.

The potential DNA binding proteins can also constitute random sequences from an epitope library encoding all or a substantial number of all possible peptide epitopes of a given length.

(2) DNA Binding Sequences

Surprisingly, it has been found that the forced evolutionary method is sufficiently powerful that it can select variants of a natural binding protein that bind with a different specificity than the natural protein and yet show improved characteristics for use in the peptides on plasmid selection method. Thus, in general there is no need to include a specific DNA binding sequence known to show a specific affinity for a natural DNA binding protein in the recombinant DNA vector. Likewise, the DNA binding protein need not show a strong preference for a specific sequence. Thus, nonsequence-specific DNA binding proteins such as histones are suitable.

In some applications, however, it is desirable to evolve a DNA binding protein having specificity for a predetermined sequence. In such applications, one includes this sequence in the recombinant vector and screens potential DNA binding proteins that are variants of the natural protein having affinity for that sequence. As discussed below, the conditions of selection can be tailored to drive evolution in favor of variants retaining affinity for the specific sequence and showing improved characteristics relative to the natural DNA binding protein. If variants of multiple natural DNA binding proteins are being screened simultaneously, a separate vector is constructed for each DNA binding protein, containing the recognition sequence for that binding protein. Families of oligonucleotide variants are then produced separately for each DNA binding protein and cloned into the vector encoding that binding protein and the corresponding recognition sequence. At this point, all the vectors can be mixed and transformation and selection can proceed as for screening variants to a single natural binding protein.

There are a number of strategies to drive evolution toward selection of DNA binding proteins having specificity for a given sequence. For example, the affinity purification step can be performed in the presence of a large excess of DNA lacking the specific binding site present in the vector. Ideally, this DNA constitutes a derivative of the vector from which the specific binding site for the DNA binding protein has been deleted. However, bulk DNA from commercial sources, such as herring or salmon sperm DNA, is generally adequate. The presence of DNA lacking the specific binding site in the screening buffer accelerates dissociation of DNA binding proteins bound other than at the specific site, resulting in a enrichment for complexes containing DNA binding proteins with affinity for the specific site.

In certain instances, retention of sequence-specific binding can be ensured by in vivo selection. For example, variants of a lacI DNA binding protein can be propagated in an *E. coli* strain having a defective chromosomal lacI gene on media containing the chromogenic substrate X-gal. Variant DNA binding proteins retaining affinity for the lacO operator repress expression of β-glactosidase and thus, do not metabolize the X-gal to a blue-colored product. Variant DNA binding proteins having lost affinity for the lacO operator express β-glactosidase, and give rise to blue colonies.

(3) Optimization of Linkers

In the fusion proteins used in the above methods, the DNA binding can be separated from the peptide by a peptide linker. Similarly, if the DNA binding protein has more than one domain, the domains can be separated by additional linker(s). Optimal peptide linkers for use in these methods can be selected by an the same forced evolutionary process as DNA binding proteins are selected. Linker(s) can be mutated and screened contemporaneously with the DNA binding protein. For example, a segment of DNA encoding both linkers and a DNA binding protein can be subjected to PCR mutagenesis. Alternatively, linkers can be mutagenized and screened before or after optimizing the DNA binding protein with which they are to be used.

(4) Selection of Fusion Sites

Generally, peptides are fused either at or near the N- or C-terminus of a DNA binding protein, because these sites offer the least constrained display of peptide with the least likelihood of disrupting the DNA binding protein. However, other viable sites of insertion are readily selected using the forced evolution method. For example, a library of vectors is constructed in which a common peptide is inserted at different sites in a DNA binding protein under test. The library of vectors is transformed and propagated in host cells, and the vectors isolated and panned for binding to the peptide receptor via the displayed peptide. The vectors binding to the receptor are those in which the site of insertion resulted in display of the peptide without disrupting the binding characteristics of the DNA binding protein.

(5) Successive Rounds of Enrichment

A single round of propagation and affinity purification of a library of potential DNA binding proteins selects a pool of vectors encoding DNA binding proteins that are at least somewhat useful for screening peptides in the peptides on plasmids method. Further optimized DNA binding proteins are obtained by performing successive rounds of enrichment. That is, vectors present in complexes bound to the receptor in the screening process are isolated, retransformed into host cells, and the selection process is repeated. Each round of selection results in greater enrichment for DNA binding proteins having optimal characteristics for use in screening peptides, because the vectors encoding these proteins are statistically most likely to survive the selection. The stringency of binding and wash buffers can be increased in successive rounds of screening as is the case when screening peptide libraries. Typically, vectors surviving four rounds of affinity selection encode DNA binding protein having highly suitable characteristics for peptide display.

In general, a DNA binding protein surviving the evolutionary process is optimized for use in the peptides on plasmids method under the same conditions as those employed in the evolutionary process. Thus, the same or similar conditions should be employed in subsequent use of a DNA binding protein in the peptides on plasmids method as were used in selecting the DNA binding protein. The conditions employed during evolution of DNA binding proteins can be changed to customize DNA binding proteins for different purposes. For example, elution of complexes bound to the screening receptor by competition with free peptide biases the selection toward survival of DNA binding proteins monovalently bound to the receptor.

Suitability can be quantified by the enrichment ratio conferred by a DNA binding protein. A vector encoding the DNA binding protein fused to a peptide is transferred into host cells and propagated as described previously to form complexes between the vector and fusion protein. Cells are lysed and the complexes are screened for binding to a receptor having affinity for the peptide, and (separately) to a receptor lacking affinity for the peptide. Vectors are recovered from bound complexes in the two situations and transformed into host cells. The enrichment ratio is that ratio of transformants resulting from screening with the receptor having affinity for the peptide divided by transformants from screening with the receptor lacking affinity for the peptide.

(f) Other Uses of DNA Binding Proteins

As well as being ideal for use in the peptides on plasmids screening method, DNA binding proteins resulting from forced evolution have a number of other uses. For example, DNA binding proteins can be used as carriers for transfer of DNA into cells. See WO 94/25608. DNA binding proteins customized to bind a specific sequence unique to a pathogenic microorganism, such as HIV, as also useful for therapeutic intervention and/or diagnosis of such an organism. See, e.g., Ladner et al., U.S. Pat. No. 5,198,346.

As can be appreciated from the disclosure above, the present invention has a wide variety of applications. Accordingly, the following examples are offered by way of illustration, not by way of limitation.

EXAMPLE 1

Construction of Plasmids pMC3 and pMC5

The bacterial strains used were *E. coli* K12 strains MC1061 (araD139 Δ(araABC-leu)7696 thr ΔlacX74 galU galK hsdR mcrB rpsL(strA) thi), ARI 20 (F⁻ lac⁺ pro⁺ lacIqL8 lacIam74 // Δ(lac-pro) thi rpsL(strA) recA::cat), and XL1-Blue (F′ proAB lacIq lacZDM15 Tn10 // recA1 endA1 gyrA96 thi hsdR17 supE44 relA1 lac), and *E. coli* B strain ARI 161 (lon-11, sulA1, hsdR17, Δ(ompT-fepC), ΔclpA319::kan). ARI 161 is a protease deficient strain and serves to minimize proteolysis of the peptides in the library, which would reduce the available diversity for panning. Mutations known to reduce proteolysis include degP, lon, htpR, ompT, and clpA,P.

The library plasmid pMC5 was constructed in several steps using plasmid pBAD18 as the starting plasmid. Plasmid pBAD18 contains the araB promoter followed by a polylinker and a terminator under the control of the positive/negative regulator araC, also specified by the plasmid. Plasmid pBAD18 also contains a modified plasmid pBR322 origin and the bla gene to permit replication and selection in *E. coli*, as well as the phage M13 intragenic region to permit rescue of single-stranded DNA for sequencing.

The lacI gene was modified for cloning into plasmid pBAD18 using the GeneAmp® PCR amplification kit (Perkin-Elmer Cetus Instruments) with oligonucleotides ON-286 and ON-287, shown below:

ON-286 5'-GCG GGC TAG CTA ACT AAT GGA GGA TAC ATA AAT GAA ACC AGT AAC GTT ATA CG-3' (SEQ. ID NO. 68)
ON-287 5'-CGT TCC GAG CTC ACT GCC CGC TCT CGA GTC GGG AAA CCT GTC GTG C-3' (SEQ. ID NO. 69).

The amplification reaction was carried out according to the manufacturer's instructions, except for the use of Vent™ DNA polymerase (New England Biolabs). ON-286 contains a nonhomologous 5' region that adds an NheI site, a consensus ribosome binding site (see Gold and Stormo, *Methods in Enzymology* (Goeddel, ed., Boston: Academic Press), pp. 89–103 (1990), incorporated herein by reference), and changes the initiation codon of lacI from GTG to ATG. ON-287 changes codons 356 and 357 of lacI to an XhoI site through two silent mutations, and adds a SacI site after the lacI stop codon.

Cloning of the NheI, SacI digested amplification product into plasmid pBAD18 produced vector pJS100. Two lacO$_s$ sequences were added to this vector, with their centers spaced 326 bp apart, by amplifying an unrelated sequence (the human D$_2$ dopamine receptor gene (see England et al., *FEBS Lett.* 279, 87–90 (1991), and U.S. Ser. No. 07/645, 029, filed Jan. 22, 1991, both of which are incorporated herein by reference), with oligonucleotides ON-295 and ON-296, shown below:

ON-295 5'-CCT CCA TAT GAA TTG TGA GCG CTC ACA ATT CGG TAC AGC CCC ATC CCA CCC-3' (SEQ. ID NO. 70)
ON-296 5'-CGC CAT CGA TCA ATT GTG AGC GCT CAC AAT TCA GGA TGT GTG TGA TGA AGA-3' (SEQ. ID NO. 71)

ON-295 adds an NdeI site and a lacO$_s$ sequence at one end of the amplified fragment, and ON-296 adds a ClaI site and lacO$_s$ at the other end. Cloning of the NdeI to ClaI fragment into pJS100 produced plasmid pJS102.

Plasmid pMC3, encoding the dynorphin B-tailed lac repressor, was constructed by cloning complementary oligonucleotides ON-312 and ON-313 to replace the XhoI to XbaI fragment at the 3' end of lacI in pJS102. These oligonucleotides add sequence encoding a five amino acid spacer (GADGA [SEQ. ID NO.:65]) and dynorphin B (YGGFLRRQFKVVT [SEQ. ID NO.:7]) to the end of the wild-type lacI sequence, introduce an SfiI site in the sequence encoding the spacer, and are shown below:

ON-312 5'-TCG AGA GCG GGC AGG GGG CCG ACG GGG CCT ACG GTG GTT TCC TGC GTC GTC AGT TCA AAG TTG TAA CCT AAT-3' (SEQ. ID NO. 72)
ON-313 5'-CTA GAT TAG GTT ACA ACT TTG AAC TGA CGA CGC AGG AAA CCA CCG TAG GCC CCG TCG GCC CCC TGC CCG CTC-3' (SEQ. ID NO. 73)

The library plasmid pMC5 was constructed by cloning complementary oligonucleotides ON-335 and ON-336 to replace the SfiI to HindIII dynorphin B segment of pMC3, as shown in FIG. 2. Oligonucleotides ON-335 and ON-336 are shown below:

ON-335 5'-GGG CCT AAT TAA TTA-3' (SEQ. ID NO. 74)
ON-336 5'-AGC TTA ATT AAT TAG GCC CCG T-3' (SEQ. ID NO. 75)

Plasmid pMC3 is available in strain ARI161 from the American Type Culture Collection under the accession number ATCC No. 68818.

EXAMPLE 2

Construction of a Random Dodecamer Peptide Library

Oligonucleotide ON-332 was synthesized with the sequence:

5'-GT GGC GCC (NNK)$_{12}$ TAA GGT CTC G-3', (SEQ. ID NO. 76)

where N is A,C, G, or T (equimolar) and K is G or T (see Cwirla et al., supra). The oligonucleotide was purified by HPLC and phosphorylated with T4 kinase (New England Biolabs). The two half-site oligonucleotides ON-369 and ON-370 were phosphorylated during synthesis and are shown below:

ON-369 5'-GGC GCC ACC GT-3' (SEQ. ID NO. 77)
ON-370 5'-AGC TCG AGA CCT TA-3' (SEQ. ID NO. 78)

ON-369 and ON-370 annealed to ON-332 produce SfiI and HindIII-compatible ends, respectively, but the ligated product does not have either recognition sequence (see FIG. 2).

Four hundred pmoles of each oligonucleotide were annealed in a 25 μl reaction buffer (10 mM Tris, pH 7.4, 1 mM EDTA, 100 mM NaCl), by heating to 65° C. for 10 min. and cooling for 30 min. to room temperature. Vector pMC5 was digested to completion with SfiI and HindIII, the vector backbone was isolated by 4 rounds of washing with TE buffer (10 mM Tris, pH 8.0, 1 mM EDTA) in a Centricon 100 microconcentrator (Amicon) by the manufacturer's instructions, followed by phenol extraction and ethanol precipitation. The annealed oligonucleotides were added to 64 micrograms of digested pMC5 at a 4:1 molar ratio in a 3.2 ml ligation reaction containing 5% PEG, 3200 units of HindIII, 194 Weiss units of T4 ligase (New England Biolabs), 1 mM ATP, 20 mM Tris, pH 7.5, 10 mM MgCl2, 0.1 mM EDTA, 50 μg/ml BSA, and 2 mM DTT. The reaction was split equally into 8 tubes and incubated overnight at 15° C.

After ethanol precipitation, 1/16 of the ligated DNA (4 μg) was introduced into MC1061 (80 μl) by electropotation (Dower et al., *Nucl. Acids Res.* 16, 6127–6145 (1988), incorporated herein by reference), to yield $5.5 \times 10^8$ independent transformants. The library was amplified approximately 1000-fold in 1 liter of LB/100 μg/ml ampicillin by growth of the transformants at 37° C. to an $A_{600}$ of 1. The cells containing the library were concentrated by centrifugation at 5500×g for 6 min., washed once in ice-cold 50 mM Tris (pH 7.6), 10 mM EDTA, 100 mM KCl, followed by a wash in ice-cold 10 mM Tris, 0.1 mM EDTA, 100 mM KCl. The final pellet was resuspended in 16 ml of HEG buffer (35 mM HEPES/KOH pH 7.5, 0.1 mM EDTA, 100 mM Na Glutamate), distributed into 19 tubes of 1.0 ml each, frozen on dry ice, and stored at −70° C.

EXAMPLE 3

Panning the Library

One aliquot (1.0 ml) of the library prepared in Example 2 was thawed on ice and added to 9 ml of lysis buffer (35 mM HEPES {pH 7.5 with KOH}, 0.1 mM EDTA, 100 mM Na glutamate, 5% glycerol, 0.3 mg/ml BSA, 1 mM DTT, and 0.1 mM pMSF). Lysozyme was added (0.3 ml at 10 mg/ml in HEG), and the mixture was incubated on ice for 1 hr.

The cellular debris was removed by centrifugation of the lysate at 20,000×g for 15 min., and the supernatant was concentrated by centrifugation in a Centriprep®100 concentrator (Amicon) at 500×g for 40 min. The concentrated supernatant (about 0.5 ml) was washed with 10 ml of HEG buffer and centrifuged as before. A sample (5%) of the total lysate was removed to determine the pre-panned input of plasmid complexes.

An alternate method for partially purifying and concentrating the lysate is as follows. About 2.0 ml of the frozen cells in HEG are thawed on ice, and then 8 ml of lysis buffer without Na glutamate (high ionic strength inhibits lysozyme; DTT is optional) are added to the cells, and the mixture is incubated on ice for 1 hr. The cellular debris is removed from the lysate by centrifugation at 20,000×g for 15 min., and the supernatant is loaded onto a Sephacryl® S-400 High Resolution (Pharmacia) gel-filtration column (22 mm×250 mm). The plasmid-fusion protein complexes elute in the void volume. The void volume (30 ml) is concentrated with two Centriprep® 100 concentrators, as described above. After adjusting the Na glutamate concentration of the concentrate, one carries out the remainder of the procedure in the same manner as with the first method.

Half of the remaining concentrated lysate was added to D32.39-antibody-coated sheep-anti-mouse (Fc)-coupled magnetic beads (10 μg of D32.39 added to 5 mg Dynal beads for 1 hr. at 25° C. followed by 6 washes with HEG), and half was added to uncoated beads. After incubating the lysates with the beads at 0° C. for 1 hr. with shaking, the beads were washed three times with 5 ml of cold HEG/0.1% BSA and then three times with HEG using a MACS 0.6 tesla magnet (Miltenyi Biotec GmBH) to immobilize the beads. The plasmids were dissociated from the beads by phenol extraction, and after adding 20 μg of glycogen (Boehringer Mannheim), the DNA was precipitated with an equal volume of isopropanol. The pellet was washed with 75% ethanol, and the DNA was resuspended in either 4 μl (panned DNA) or 400 μl (pre-panned DNA) of $H_2O$. Strain MC1061 was transformed using 2 μl each of the DNA solutions to permit counts of recovered plasmids and amplification of the selected plasmids. The results of the panning are shown below in Table 1.

TABLE 1

| Panning Round | Number of Transformants | | |
|---|---|---|---|
| | Input | Ab D32.39 Beads | Uncoated Beads |
| 1 | $1.6 \times 10^{10}$ | $9 \times 10^7$ | $1.7 \times 10^5$ |
| 2 | $1.4 \times 10^{11}$ | $6.1 \times 10^7$ | $1.2 \times 10^4$ |
| 3 | $1.7 \times 10^{11}$ | $2.0 \times 10^9$ | 40 |
| 4 | — | $1.6 \times 10^{11}$ | $4 \times 10^4$ |

EXAMPLE 4

ELISA Analysis of the Library

An ELISA was used to test MC1061 transformants from the second, third, and fourth rounds for D32.39-specific ligands (see Example 3). The ELISA was performed in a 96-well plate (Beckman). Single colonies of transformants obtained from panning were grown overnight in LB/100 μg/ml ampicillin at 37° C. The overnight cultures were diluted 1/10 in 3 ml LB/100 μg/ml ampicillin and grown 1 hr. The expression of the lac repressor-peptide fusions was induced by the addition of arabinose to a final concentration of 0.2%.

The cells were lysed as described above in 1 ml of lysis buffer plus lysozyme and stored at −70° C. Thawed crude lysate was added to each of 2 wells (100 μl/well), and the plate was incubated at 37° C. After 45 min, 100 μl of 1% BSA in PBS (10 mM NaPO4, pH 7.4, 120 mM NaCl, and 2.7 mM KCl) were added for an additional 15 min. at 37° C. followed by 3 washes with PBS/0.05% Tween 20. Each well then was blocked with 1% BSA in PBS (200 μl/well) for 30 min at 37° C., and the wells were washed as before.

The primary antibody, D32.39 (100 μl of antibody at 1 μg/ml in PBS/0.1% BSA) was added to each well, the plate was incubated at room temperature for 1 hr., and then each well was washed as before. The secondary antibody, alkaline phosphatase-conjugated Goat-anti-rabbit antibody (Gibco-BRL), was diluted 1/3000 in PBS/0.1% BSA and added to each well (100 μl/well); the plate was then incubated for 1 hr at room temperature. After three washes with PBS/0.05% Tween 20 and two with TBS (10 mM Tris pH 7.5, 150 mM NaCl), the ELISA was developed with 4 mg/ml p-nitrophenyl phosphate in 1M diethanolamine/HCl pH 9.8, 0.24 mM $MgCl_2$ (200 μl/well).

The reaction was stopped after 6 min. by the addition of 2M NaOH (50 μl/well), and the absorbance at 405 nm was measured on a plate reader (a Biomek, from Beckman). The positive control for the ELISA was MC1061 transformed with pMC3, encoding the lac repressor-dynorphin B fusion. The negative controls were wells not coated with lysate. Background variability was calculated from the wells containing lysates from 16 colonies selected at random from the library, none of which scored significantly above the negative controls. Wells were scored as positive if the measured absorbance was at least two standard deviations above background.

Of randomly picked colonies, 35 of 58 (60%) tested positive by ELISA: 11 of 20 from round two, 12 of 16 from round three, and 12 of 22 from round four. None of 16 random colonies from the unpanned library scored significantly above background. These data demonstrate the rapid enrichment of specific ligands achieved by the present invention: after only two rounds of panning, the majority of plasmids encoded peptides with affinity for the D32.39 antibody.

To determine the structure of the peptide ligands obtained by the present method, plasmids from both ELISA positive and ELISA negative colonies obtained after panning were sequenced. Double stranded plasmid DNA, isolated from strain XL1-Blue, was sequenced using Sequenase® (US Biochemicals) according to the instructions supplied by the manufacturer.

The translated peptide sequence for all ELISA positive colonies examined shared the consensus sequence shown in FIG. 3. The preferred recognition sequence for the D32.39 antibody apparently covers a six amino acid region of the dynorphin B peptide (RQFKVV). In the first position, arginine is invariant for all of the ELISA positive clones. No strong bias was evident for residues in the second position. In the third position, however, five amino acids (phenylalanine, histidine, asparagine, tyrosine, and tryptophan, in order of frequency) account for 98% of the residues. Of these, the aromatic amino acids comprise 74% of this total. The fourth position shows a strong bias for the positively charged residues lysine (69%) and arginine (21%). The fifth position is occupied almost exclusively by hydrophobic residues, most of which are valine (81%). Valine and threonine predominate in the sixth position (76%), with serine and isoleucine accounting for most of the remaining amino acids.

Of the ELISA negative clones obtained after panning, greater than half showed peptide sequence similarity to the consensus motif (FIG. 3). None of 19 isolates sequenced from the unpanned library showed any such similarity. Some of these ELISA negative sequences differ enough from the consensus that their affinity for the antibody may be insufficient to permit detection in the ELISA. There are, however, ELISA negative sequences identical in the five conserved amino acids of the consensus region to clones that scored positive (e.g., #28 and #57). There may be amino acids outside the consensus region that affect binding of the peptide to antibody or its susceptibility to E. coli proteases, or its availability in the ELISA. That even the ELISA negative clones frequently have an obvious consensus sequence demonstrates the utility of the present invention for isolating ligands for biological receptors.

EXAMPLE 5

1. Optimization of linkers for headpiece dimer display

Figure 5:
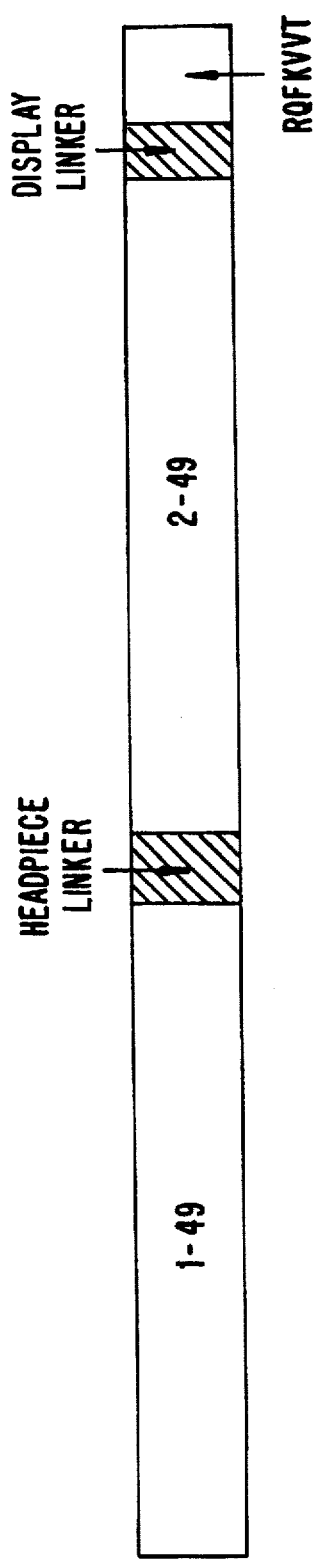
FIG. 5 (SEQ ID NO.66) Arrangement of lac headpieces, linkers and displayed peptide in headpiece dimer.
Figure 7A:
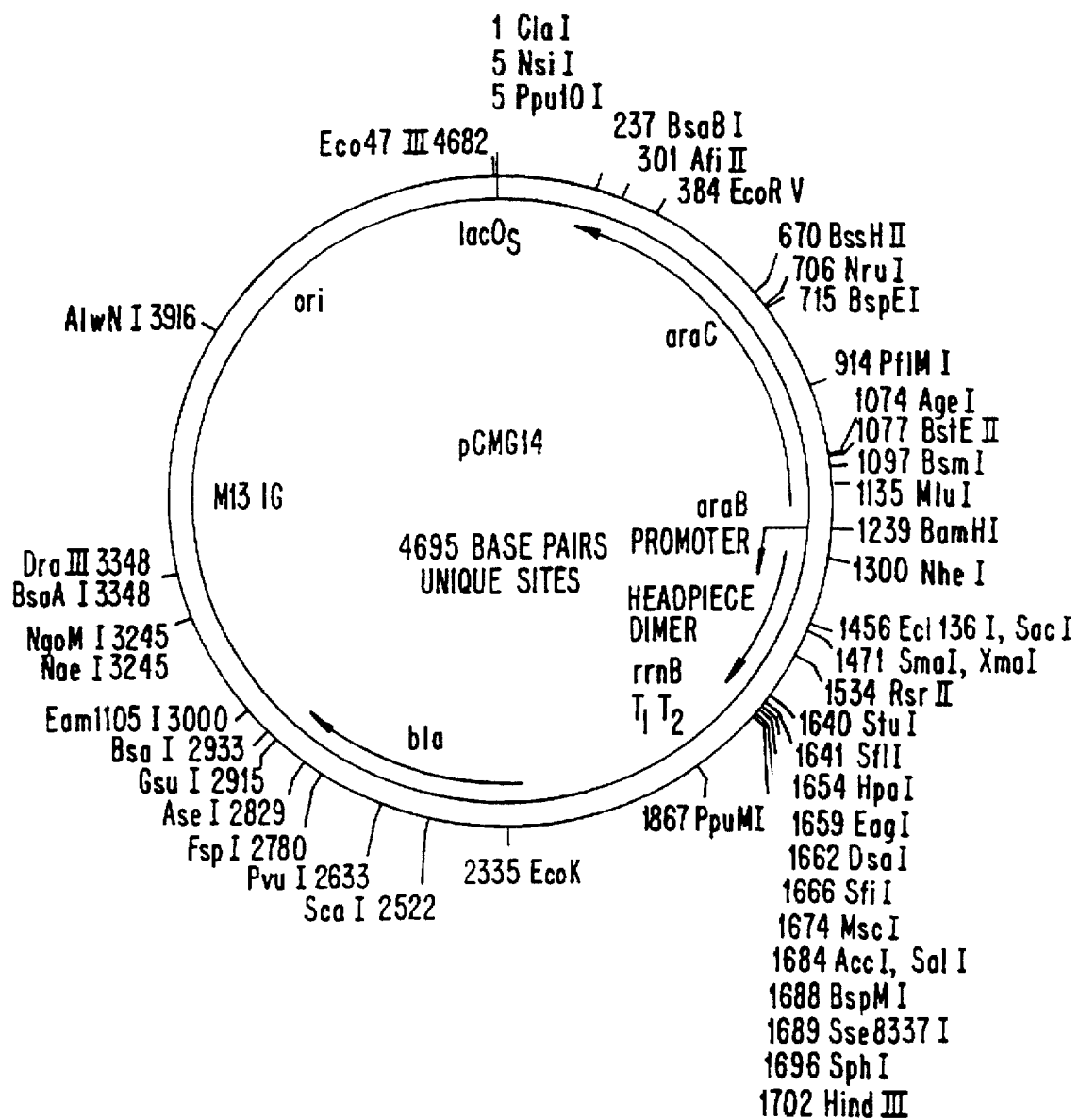

To obtain headpiece dimer polypeptides that bind to their encoding plasmids with sufficient stability to facilitate affinity purification, two headpiece domains were inserted in a construct adjoined by random linkers (FIGS. 5 & 6a). The vector (pDimer1) contained two repeated segments of the lac repressor gene, respectively encoding residues 1–49 and 2–49 of the headpiece DNA binding domain. These two segments were linked by a sequence encoding a 4–5 random residue "headpiece linker" which, based on molecular modeling, might allow positioning of the headpiece DNA binding domains for stable binding to lacO$_s$ sites present on the parent plasmid. Fused to the second headpiece domain was a sequence encoding a 4 random residue "display linker" designed to facilitate the C-terminal display of peptide ligands. To screen the initial "linker library", a 7 residue epitope (RQFKVVT) for the D32.39 monoclonal antibody (Barrett & Goldstein, Neuropeptides 6, 113–120 (1985)) was fused to the C-terminal display linker. To increase the chance of finding active headpiece dimers, the vector was designed to have two lacO$_s$ sites.

Headpiece dimer "linker" library plasmid pDIMER1 was constructed as follows. 10 ng pMC5 (encoding lacI headpiece domain) as a template, primers ON-929 (TATTTGCACGGCGTCACACTT [SEQ ID NO.79]) and ON-930 (CCGCGCCTGGGCCCAGGGAATGTAATTGA GCTCCGCCATCGCCGCTT [SEQ ID NO.80]) were used in a (25 cycle) PCR reaction to modify the ends of the region encoding the first 49 residues of lacI to form headpiece #1. About 1 μg of the modified fragment encoding headpiece #1 was digested with BamHI and ApaL gel purified, and inserted between the BamHI and ApaI sites of pMC5, replacing the lacI coding region, to form intermediate plasmid pMC5dlacL To construct "headpiece #2", PCR primers ON-938 (CGATGGCGGAGCTCAATTACATTCCC-(NNK)$_5$-AAACCAGTAACGTTATACGAT [SEQ ID NO.81]), ON-939 (CGATGGCGGAGCTCAATTACATTC CC-(NNK)$_4$-AAACCAGTAACGTTATACGAT [SEQ ID NO.82]), and ON-940 (CGCCCGCCAAGCTTAGGTTAC AACTTTGAACTGACG-(MNN)$_4$-GGGAATGTAATTCA GCTCCGCCAT [SEQ ID NO.83]), were used to attach sequences encoding a 4 or 5 random residue "headpiece" linker, a 4 random residue "display" linker, and the D32.39 monoclonal antibody epitope (RQFKVVT [SEQ ID NO.66]) (Barrett & Goldstein, Neuropeptides 6, 113–120 (1985); Cull et al., Proc. Natl. Acad. Sci. USA 89, 1865–1869 (1992)) to codons 2 through 49 of the lacI headpiece. Approximately 1 μg of the end-modified DNA fragment encoding headpiece #2 was digested with SstI and HindIII, gel purified and ligated into the SstI and HindIII sites of pMC5dlacL Plasmids encoding four-random-residue headpiece linkers were combined with those encoding five-random-residue linkers at a ratio of approximately 10:1 to make the pDIMER1 linker library. The pDIMER1 library was introduced into bacterial strain ARI 280 by electroporation to produce a library of $3 \times 10^8$ individual transformants.

The headpiece dimer gene was expressed under the control of the araB promoter using three separate induction levels. The linker library was amplified in three 325 ml LB/Amp$_{100}$ medium (100 μg/ml ampicillin) pools containing, LB with no additives for basal "A" promoter induction, LB with 0.1% glucose followed by promoter induction with 0.2% L-arabinose for 30 min prior to harvest to give partial "B" induction levels, and LB with 0.2% L-arabinose for 15 min prior to harvest for full "C" promoter induction.

Upon cell lysis, the subset of these plasmids that displayed the D32.39 epitope was enriched relative to other plasmids in the population. Stable complexes were captured by panning the lysate in microtiter wells coated with immobilized D32.39 antibody. Panning was carried out in Immulon 4 microtiter wells (Dynatech Laboratories) coated with 2 µg per well D32.39 antibody as described in Example 6, except that HEK/1% BSA (35 mM HEPES (Research Organics Inc.), pH 7.5 with KOH, 0.1 mM EDTA, 50 mM KCl, 1% Bovine Serum Albumin, Fraction V) replaced HEKL/BSA as the primary incubation and wash buffer. In all rounds, 0.1 to 0.2 mg/ml sonicated herring DNA was included in the incubation buffer as a nonspecific DNA competitor. In rounds three and four of panning, 5 to 10 µg/ml of self-annealed ON-413, a lacO$_s$ containing oligonucleotide (GAA TTC AAT TGT GAG CGC TCA CAA TTG AAT TC [SEQ ID NO.84]) was included in the incubation buffer as a competitor. Following a one hour incubation at 4° C., unbound headpiece dimer complexes were washed from the wells four times with HEK/BSA followed by two washes with HEK. Bound plasmids were extracted from the wells using 50 µl/well TE/NaCl buffer (10 mM Tris-HCl, (pH 7.5)/1 mM EDTA/0.5M NaCl) mixed with 50 µl/well phenol. After addition of 1 µl glycogen carrier (20 mg/ml, Boehringer Mannheim), the recovered plasmids were precipitated with an equal volume of isopropanol, followed by a 10 minute spin at 14,000 rpm in a microfuge. Plasmids were resuspended in 4 µl water and used to transform bacterial strain ARI 280 for recovery counts and further rounds of panning. After two rounds of panning, enrichment numbers indicated that the pools grown under conditions of "B" (partial), and "C" (full) promoter induction, gave the best enrichment. Based on this finding, only the B and C pools were used in rounds 3 and 4.

Sequencing of individual clones selected after four rounds of panning revealed the primary structure of their linkers. Of 22 clones that yielded readable sequence, 5 contained frameshifts or stop codons which would prevent translation of the D32.39 epitope. Two B pool clones, isolates B7 and B10, were present as duplicates, indicating selective enrichment by the panning procedure from less than one in 10$^8$ to more than one in six. Surprisingly, one of the enriched clones, isolate B10, and one C pool clone, C5, had frameshifts early in the second headpiece domain with a second frameshift late in the headpiece coding sequence that restored the reading frame of the D32.39 epitope (FIG. 6b).

To assess which clones encoded the most stable DNA binding proteins while displaying the epitope in the most favorable way, the clones were individually evaluated in a panning experiment. Each clone having the D32.39 epitope in the correct frame was examined together with one clone having a frameshifted epitope as a negative control. An intact lacI construct (see Example 3) served as a positive control. Each clone was panned against D32.39 Ab and also against MAb344 as a negative control. Specific enrichment was evaluated by transformation of E. coli with recovered plasmids.

After four rounds of panning, individual clones were grown in LB/Amp100/0.1% glucose for two hours at 37° C. Following addition of L-arabinose to 0.2% (B induction), cultures were grown for an additional 30 min, then chilled on ice for harvest. 1 ml of each culture was microfuged for 2 min at 14,000 rpm. The cells were washed with 0.5 ml ice cold WTEK buffer (50 mM Tris, (pH 7.5), 10 mM EDTA, 100 mM KCl), centrifuged for 2 min, washed with 0.25 ml cold TEK buffer(10 mM Tris, (pH 7.5)/0.1 mM EDTA/100 mM KCl), centrifuged, then resuspended in 100 µl cold HEK buffer. To each resuspended cell culture, 0.9 ml lysis buffer (35 mM HEPES, (pH 7.5 with KOH), 0.1 mM EDTA, 5% Glycerol, 1 mM DTT, 0.1 mM pMSF (phenylmethylsulfonyl fluoride), 0.1 mg/ml BSA) was added. Cell were lysed by adding 20 µl of 10 mg/ml lysozyzme (Boehringer Mannheim) to each tube followed by incubation on ice for 1 hr. The lysed cell cultures were then microfuged at 14,000 rpm for 10 min at 4° C., and the supernatant transferred to a new tube.

To evaluate each clone, 10 µl of clear lysate was added to methacrylate beads (Affi-prep 10 support, Bio Rad) coated with the D32.34 monoclonal antibody, or negative control MAb344, suspended in 0.5 ml HEK/BSA/0.01 mg/ml herring DNA. After incubation at 4° C. on a tube rotator for one hour, beads were washed twice with cold HEK/BSA and twice with HEK over a 50 min period. The remaining antibody-bound plasmid complexes were recovered from the beads by phenol extraction and isopropanol precipitation. Enrichment was defined as the number of transforming units of plasmid recovered panning against the D32.39 antibody beads divided by the number recovered panning against the MAb344 control antibody.

The individual evaluations revealed relatively few clones that yielded greater recovery with D32.39 Ab compared to the negative control. Only four isolates (B7, B10, C4, C5 in FIG. 6) showed enrichment greater than two fold. The best clones were B7 and B10, the same isolates that represented a large fraction of the round four population. These isolates yielded enrichment of 8 and 28 fold respectively. Of the four clones showing specific enrichment, three contained cysteine residues in their headpiece spanning linkers and all four had a proline residue in their display linkers suggesting that some degree of activity might be conferred by these residues. Surprisingly good enrichment was achieved by isolates B10 and C5, which contain reading frame shifts in the region encoding the second headpiece resulting in an entirely different amino acid sequence from that encoded in the first headpiece domain (FIG. 6). Overall, the headpiece dimer clones performed less well than the lacI system described in Example 3.

2. Isolation of Mutant Headpiece Dimers

To increase headpiece dimer/DNA complex stability and thereby increase the panning performance of individual clones, random mutations were introduced in the regions encoding the headpiece dimer and adjoining linkers. Some mutations in lacI resulting in tighter-binding mutants have been reported (Betz & Sadler, J. Mol. Biol. 105, 293–319 (1976); Kleina & Miller, J. Mol. Biol. 212,295–318 (1990); Kolkhof, Nucl. Acids. Res. 20, 5035–5039 (1992); Maurizot & Grebert, FEBS Lett. 239.(1), 105–108 (1988); Miller, The Operon (Miller & Reznikoff, eds.), pp. 31–88 (1980), Cold Spring Harbor Laboratory, Cold Spring Harbor, N.Y.).

The starting population for mutagenesis was the headpiece dimer B pool, obtained after four rounds of random linker library panning. Starting with pDIMER1 B pool plasmids, isolated after four rounds of affinity purification as a template, flanking primers were used in an adaptation of mutagenic PCR (Gram et al., Proc. Natl. Acad. Sci. USA 89, 3576–3580 (1992); Leung et al., Technique 1, 11–15 (1989)) to generate mutations within the headpiece dimer and linker coding sequence. Approximately 2 µg of mutated DNA fragments generated by PCR was digested using NheI and HindIII and cloned into plasmid pJS145 (a single lacO$_s$-containing vector). The ligation was amplified in ARI 280 using A and B induction conditions, to lower the total amount of headpiece dimer protein in the cells, as described above to produce a library of 1.6×10$^8$ individual transformants. Stable headpiece dimer/plasmid complexes were selected from this population by panning for four rounds on methacrylate beads (Affi-prep 10 support, Bio Rad) coated with the D32.39 monoclonal antibody. Elution from beads was carried out for one hour at 4° C. using 100 µl/well HEK buffer containing 2.8 μM synthetic peptide RBO-11 (RQFKVVT [SEQ ID NO.66]). Complexes were eluted with peptide containing the RQFKVVT [SEQ ID NO. 66] epitope in all four rounds.

To determine whether any specific mutations had been selected through four rounds of panning and amplification, the regions encoding the headpiece DNA binding domain and adjoining linkers were sequenced from individual clones. Six of eight A pool clones and one B pool clone had a specific Q to R mutation at position 18 within one or both headpiece domains (FIG. 6). Significantly this Q18 to R mutation falls in a portion of the headpiece DNA binding helix that is critical for the recognition of operator DNA by lacI (Boelens et al., *J. Mol. Biol.* 193, 213–216 (1987); Chuprina et al., 1993; Ebright, *Proc. Natl. Acad. Sci. USA* 83, 303–307 (1986); Lamerichs et al., *Biochemistry* 28, 2985–2991 (1989); Lehming et al., *EMBO J.*, 9, 615–621 (1990); Lehming et al., *EMBO J.* 6, 3145–3153 (1987); Lehming et al., *Proc. Natl. Acad. Sci. USA* 85, 7947–7951 (1988); Sartorius et al., *EMBO J.* 8, 1265–1270 (1989)). Many other mutations were present throughout the headpiece dimer and linker coding regions.

To evaluate individual mutant headpiece dimer clones, single clones were analyzed for enrichment under the conditions described above. Non-mutant headpiece dimer B7, a lacI clone, and an out-of-frame headpiece dimer clone were used as controls. The headpiece linkers chosen to display the mutant headpiece clone had each been identified in more than clonal isolate in the linker optimization screening. The promoter induction conditions for these tests were A and B reflecting the conditions used for the initial selection of the mutants.

TABLE 2

| Isolate | Description | Enrichment | | |
|---|---|---|---|---|
| | | Exp. #1 | Exp. #2 | Exp. #3 |
| ARI 192 | wt. lacI (+CT) | — | — | 155 |
| B2.2 | Framshift (N.C.) | 0.44 | 0.77 | 0.44 |
| B7 | wt. HpD. | 0.64 | 1.24 | 10.0 |
| A4.2 | mutant HpD. | 6.2 | 3.3 | 61.0 |
| A4.5 | mutant HpD. | 360 | 377 | 1017 |
| A4.7 | mutant HpD. | 11.6 | — | — |
| A4.8 | mutant HpD. | 95.0 | 11.6 | 70.0 |
| B4.5 | mutant HpD. | 365 | 116 | 850 |
| B4.7 | mutant HpD. | 383 | 3.5 | 18.0 |
| B4.8 | mutant HpD. | — | 14.6 | 57.0 |

Experiments #1 and #2 were carried out using basal (A) promoter induction conditions, experiment #3 was carried out using partial (B) promoter induction.

Table 2 shows greater enrichment was obtained from all of the selected mutants than the wild-type headpiece dimer B7. Of the nine mutants tested, two isolates from separate pools, numbered A4.5 and B4.5, showed the greatest enrichment under both basal and partial promoter induction conditions. These two clones share the same Q18 to R mutation in their second headpiece DNA recognition helices suggesting that this mutation might be important for DNA binding. These clones also contain the GRCR headpiece linker found in the B7 isolate, although mutant A4.5 contains a display linker that is different than the one shared by B7 and mutant B4.5 (FIG. 6).

Expression levels of several mutant headpiece dimer proteins were analyzed in whole cell lysates on SDS/PAGE to determine whether increased enrichment was due to increased expression levels. Staining of proteins from cells grown under conditions of A or B induction showed little difference in 14.5 kD headpiece dimer polypeptide expression between mutants A4.5 and B4.5 as compared to the non-mutant B7. Western blot analysis of these clones using the D32.39 antibody showed similar levels of expression, indicating that levels of enrichment for individual mutants were probably due to structure and not expression levels.

3. Screening a Random Library Using Optimized Headpieces and Linkers

The library was constructed in plasmid pCMG14 which contains headpiece dimer mutant A4.5 under the control of the araB promoter. A series of restriction sites at the 3' end of the gene facilitate cloning of synthetic oligonucleotides, allowing fusion of the headpiece dimer display linker to a random peptide. Each member of the random library consists of a peptide-displaying headpiece dimer bound to its encoding plasmid.

A random dodecamer library comprising $10^9$ oligonucleotide members was inserted into pCMG14. As a control, a lacI-based peptides-on-plasmids library of similar size using the same random library oligonucleotides was constructed in parallel. Identical bacterial strains, panning conditions, and basal promoter induction was used for both libraries. Libraries were panned in microtiter wells coated with D32.39 antibody or the same amount of MAb344, as a negative control. Recovery of plasmids during panning yielded enrichment for both libraries. By round 4, the headpiece dimer library showed 1855 fold enrichment over the negative control while the lacI library yielded 1150 fold enrichment. FIG. 8 shows that isolates picked from both libraries encoded peptide structures similar to the D32.39 antibody epitope (RQFKVVT [SEQ ID NO:66]). The enrichment and sequencing results show that the headpiece dimer system selects peptide sequences that bind specifically to a receptor.

To verify receptor specificity and to determine the relative affinity of the headpiece dimer versus the lacI-library derived peptide sequences obtained through panning, the peptide-encoding sequences from each fourth round library pool were transferred into a vector such that the peptides would be fused in frame with the maltose binding protein (MBP) (Bedouelle & Duplay, *Eur. J. Biochem.* 171, 541–549 (1988); Duplay et al., *J. Biol. Chem.* 259, 10606–10613 (1984); Guan et al., *Gene* 67, 21–30 (1988); Maina et al., *Gene* 74, 365–373 (1988)). This transfer permitted comparison of the headpiece dimer and lacI derived peptides fused in an identical fashion to the same carrier protein.

Figure 9:
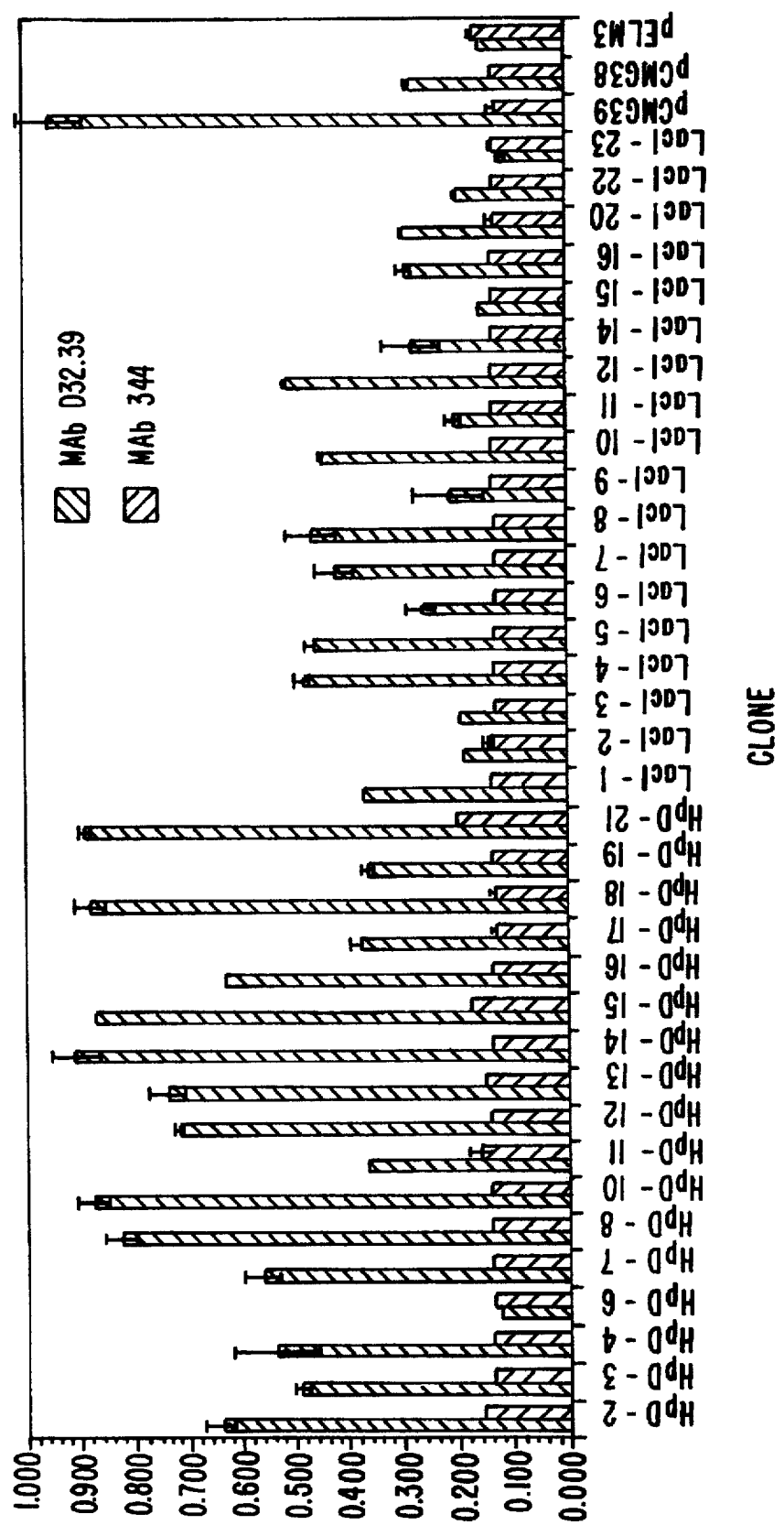
FIG. 9: MBP ELISA using peptides isolated from headpiece dimer and lacI peptides-on-plasmids random libraries. High and low affinity control peptides are expressed by plasmids pCMG39 and pCMG38, respectively. pELM3 negative control encodes MBP with an irrelevant fusion peptide. Random library clones are numbered as in FIG. 8.

Under the conditions employed, MBP exists primarily as a monomer (Blondel & Bedouelle, *Prot. Engineer* 4, 457–461 (1991); Kellerman & Ferenci, *Meth. Enzymol.* 90, 459–463 (1982); Richarme, Biochem. *Biophys. Res. Comm.* 105, 476–481 (1982); Richarme, Biochem. *Biophys. Acta.* 748, 99–108 (1983)) and thus the MBP-peptide fusions would be expected to bind to receptor monovalently. This non-cooperative interaction should allow a good correlation between affinity of the peptide for the receptor and the level of receptor occupancy during binding and washing steps. The intensity of the ELISA signal is expected to correlate approximately with peptide affinity. Evidence supporting this hypothesis was obtained by comparing the ELISA signal strength produced by MBP fused to different epitopes of known affinity. FIG. 9 demonstrates that MBP fused to epitopes with affinities of 340 nM (pCMG38) and 0.51 nM (pCMG39) produced dramatically different ELISA signals. Using other peptide ligand families, the intensity of the signal in the MBP ELISA correlates approximately with the affinity of the ligand for a receptor.

Lysates of 23 randomly picked isolates from each library pool were tested in ELISAs with the D32.39 antibody test receptor, or MAb344 and BSA as controls. Clones without the correct insert DNA structure determined by sequencing were excluded from subsequent analysis. FIG. 9 shows that of 19 clones from the headpiece dimer library pool included in the analysis, 13 showed MBP ELISA signals greater than 0.5. Of 21 isolates from the lacI library, however, only 2 yielded signals of 0.5 or greater. A comparison of the two data sets using an unpaired t test showed the difference was significant (P<0.0001). This comparison indicates that the headpiece dimer system can selectively enrich ligands with higher affinity than those obtained by the multivalent lacI-based peptides-on-plasmids system.

4. Headpiece Dimer DNA Binding Studies

The selection system by which headpiece dimers were selected demanded two things. First, that the protein bind to the plasmid that encoded it with acceptably high stability. Second, that the plasmid-protein complex display a peptide in such a way that it was available for binding to an immobilized receptor. Many mutations were present in the pool of selected headpiece dimers including the Q18 to R mutation, at a position known to be critical for lacO$_s$ sequence recognition in lacI (Lehming et al., EMBO J. 9, 615–621 (1990)). This experiment investigates whether some of the headpiece dimer mutants might-employ DNA binding sites other than lacO$_s$.

To compare the mechanism of DNA binding between the mutant headpiece dimer A4.5 and lacI, two pairs of plasmids were constructed, one pair with, and the other pair without, lacO$_s$ binding sites. Removal of lacO$_s$ sites from the plasmids was carried out by replacing the NheI to AlwNI fragment with a similar fragment that lacked lacO$_s$. One member of each pair displayed the D32.39 epitope linked to chloramphenicol resistance, and the other carried ampicillin resistance but lacked the epitope. Starting with cells mixed in the ratio of ~1 Cam® cell to 1000 Amp® cells, lysates were panned against the D32.39 antibody and the control MAb344. Plasmids recovered from the antibody coated wells were transformed into E. coli and plated on Amp (100 μg/ml) and Cam (20 μg/ml) plates for the determination of Amp/Cam plasmid ratios as a measure of enrichment. Enrichment was defined as the starting Amp/Cam plasmid ratio divided by the final (panning derived) Amp/Cam ratio.

As expected, in three separate experiments, deletion of lacO$_s$ sites resulted in an average 446 fold enrichment drop to near background level for the lacI peptides-on-plasmids construct. For headpiece dimer mutant A4.5 constructs, however, deletion of the plasmid lacO$_s$ site had no significant effect on enrichment. An average 43 fold enrichment was obtained by the headpiece dimer mutant A4.5 constructs with lacO$_s$ and an average 44 fold was achieved without lacO$_s$. This finding suggests that the headpiece dimer mutant A4.5 does not require binding to lacO$_s$ as a mechanism of linkage to its parent plasmid. This is consistent with observations made on mutants of full length lacI which, upon substitution at position 18, lose lacO site binding specificity (Kleina & Miller, J. Mol. Biol. 212.295–318 (1990); Lehming et al., EMBO J. 9, 615–621 (1990); Lehming et al., EMBO J. 6, 3145–3153 (1987)).

To determine the plasmid binding site(s) of headpiece dimer mutant A4.5 and the non-mutant B7, several protein-DNA binding experiments were performed. Preliminary gel shift experiments with plasmid pCMG14 digested into small fragments combined with headpiece dimer A4.5 polypeptide, resulted in no visible shift for any of the plasmid fragments. Other experiments using $^{32}$P-labeled plasmid fragments complexed with over-expressed headpiece dimer A4.5, B7, and full-length lacI polypeptides, showed specific binding of lacI to lacO$_s$-containing fragments, but failed to show any specific binding by the mutant (A4.5) and non-mutant (B7) headpiece dimers. Another experiment, in the absence of unlabelled herring DNA competitor, showed nonspecific binding to all of the plasmid fragments by lacI and both headpiece dimer isolates indicating that some degree of nonspecific DNA binding occurs for headpiece dimers and lacI alike.

These result indicate that the mutant headpiece dimer, while offering improved performance over the lacI plasmid, surprisingly does not require a lacO binding site for use in the panning procedure. The in vitro binding data suggest that the mutant headpiece dimer may not show a strong preference for a specific sequence in the vector encoding the headpiece dimer.

Although the mechanism and degree of sequence specificity, if any, by which the mutant headpiece binds to DNA are unclear, the power of the above methodology to self-select optimal DNA binding proteins for use in screening peptides is evident. The method has self-selected a derivative DNA binding protein that has substantially different binding characteristics than the natural lacI protein, but which offers improved enrichment compared with the lacI parent protein in selection of peptides having high affinity for a receptor.

EXAMPLE 6

Standard Protocol

This Example provides a standard protocol for the method of the present invention with any receptor that can be immobilized on a microtiter dish with an immobilizing antibody.

(1) Reagents

To practice the method, the following reagents will be helpful.

| Items | Vendor | Catalog # |
|---|---|---|
| BSA, fraction V, RIA grade | USB | 10868 |
| BSA, protease free | USB | 10867 |
| Bulk DNA, sonicated, phenol extracted | Amicon | 4308 |
| Centriprep 100 concentrator, 5–15 ml | | |
| Chromatography column, G22X250 | Amicon | 95220 |
| Coomassie Plus protein assay reagent | Pierce | 23236 |
| DTT | | |
| EDTA, disodium, dihydrate | Sigma | E-5134 |
| Ethyl alcohol, 200 proof | Gold Shield Chem. | |
| Glycerol | Sigma | G-5516 |
| Glycogen, molecular biology grade | Boehringer | 901 393 |
| HEPES free acid | Research Organics | 6003H |
| Isopropanol, HPLC grade | Aldrich | 27,049-0 |
| IPTG | Bachem | SISO10 |
| a-Lactose, monohydrate | Sigma | L-3625 |
| Lysozyme, from hen egg white | Boehringer | 837 059 |
| Microtiter plate, Immulon 4, flat bottom | Dynatech | 011-010-3850 |
| PBS | Sigma | 1000-3 |
| PMSF | | |
| Phenol, equilibrated | USB | 20072 |
| Phenol:chloroform:Isoamyl alcohol | USB | 20081 |
| Potassium hydroxide solution, 8.0 N | Sigma | 17-8 |
| Potassium chloride | Sigma | P-9541 |
| Sodium chloride | Sigma | S-3014 |
| Sephacryl S-400, high resolution | Pharmacia | 17-0609-01 |
| Tubes w/ screw cap, 13 ml | Sarstedt | 60.540 |

The various buffers and other preparations referred to in the protocol are shown below.

HE buffer is prepared at pH=7.5 by adding 8.34 g of HEPES, free acid (use a better grade than Sigma's standard; the final concentration is 35 mM), to 200 µl of 0.5M EDTA, pH 8.0 (final concentration is 0.1 mM) and adding water to a final volume of 1 L. The pH is adjusted with KOH.

HEK buffer is identical to HE buffer but also contains KCl at a final concentration of 50 mM.

HEKL buffer is identical to HEK buffer but also contains alpha-lactose, which may require warming to go into solution, at a final concentration of 0.2M.

Lysis buffer (6 ml) is prepared by mixing 4.2 ml of HE buffer with 1 ml of 50% glycerol, 750 µl of protease free BSA at 10 mg/ml in PBS, 10 µl of 0.5M DTT, and 12.5 µl of 0.1M pMSF in isopropanol.

HEK/BSA buffer is prepared by dissolving 5 g of 1% BSA, fraction V, in 500 ml of HEK buffer.

WTEK buffer is prepared at pH=7.5 by adding 7.53 g of Tris, pH=7.5 (final concentration of 50 mM), to 20 ml of 0.5M EDTA (final concentration of 10 mM) and 7.45 g of KCl (final concentration of 100 mM) and adding water to a final volume of 1 L.

TEK buffer is prepared at pH=7.5 by adding 1.51 g of Tris, pH=7.5 (final concentration of 10 mM), to 200 µl of 0.5M EDTA (final concentration of 0.1 mM) and 7.45 g of KCl (final concentration of 100 mM) and adding water to a final volume of 1 L.

(2) Bacterial Strains

*E. coli* ARI 439 (lon-11 sulA1 hsdR17 Δ(ompT-fepC) ΔclpA319::kan ΔlacI lacZU118 Δ(srl-recA)306::Tn10) was used for random dodecamer panning. *E. coli* ARI 814 Δ(srl-recA) endA1 nupG lon-11 sulA1 hsdR17 Δ(ompT-fepC) ΔclpA319::kan ΔlacI lacZU118) was used for panning lacO$_s$ deletion variants and to isolate DNA for sequencing.

The various mutations in strain ARI 814 are designed to enhance various aspects of panning as described below. It was constructed in 11 steps starting with an *E. coli* B strain from the *E. coli* Genetic Stock Center at Yale University (*E. coli* B/r, stock center designation CGSC6573) with genotype lon-11 sulA1. This strain was chosen as a starting point because of its robust growth properties and because it yields excellent electrocompetent cells, which are essential for construction of large libraries and for the maintenance of clone diversity during panning. In spite of considerable genetic manipulation, the strain maintained these favorable growth and transformation properties through the construction process.

The strain contains the hsdR17 allele from strain MC1061 which prevents restriction of unmodified DNA introduced by transformation or transduction. This mutation helps maintain library diversity and simplified further construction steps. The ompT-fepC deletion from strain UT5600 removes the gene encoding the ompT protease, which digests peptides between paired basic residues. This protease is extremely active in cell lysates and would potentially have been a major limitation on the diversity of peptides in a random library. The lon-11 and clpA mutations also limit proteolysis because they prevent expression of ATP-dependent, cytoplasmic proteases. The sulA1 allele suppresses a deleterious filamentation phenotype often caused by lon mutations.

ARI 814 also contains a deletion of the lacI gene to prevent expression of wild-type lac repressor, which would compete with the fusion constructs for binding to the lacO sites on the plasmid. The lacZ mutation prevents waste of the cell's metabolic resources making β-galactosidase due to absence of the repressor. The endA1 mutation knocks out expression of a nuclease that has two deleterious effects on panning. First, it could digest plasmids in the crude cell lysate used for panning, reducing the number of recoverable complexes. Second, it lowers the quality of DNA preparations used for cloning or sequencing. Finally, the ARI 814 strain contains a recA deletion to prevent multimerization of plasmids through recA-catalyzed homologous recombination.

ARI 814 is prepared for use in electroporation essentially as described by Dower, supra, except that 10% glycerol is used for all wash steps. The cells are tested for efficiency using 1 pg of a pBluescript plasmid (Stratagene). Cells routinely yield transformation frequencies of $2 \times 10^{10}$ colonies per µg of DNA. These cells are used for growth of the original library and for amplification of the enriched population after each round of panning.

(3) Library construction

The interrupted palindrome SfiI sites in pJS142 allow efficient cloning of library oligos because they greatly minimize undesired legation events. Only the correct orientation of the annealed library oligos can ligate efficiently into the vector. In addition, once the SfiI digested vector is purified away from the small internal "stuffer" fragment, the vector ends cannot legate to each other because of incompatible sticky ends. Libraries routinely have greater than $10^8$ independent clones per µg of vector used in the ligation.

Vector fragment for library construction can be purified from the stuffer fragment by either of two methods. For small scale (5–10 µg) library construction, pJS142 is digested with SfiI and then with EagI (to reduce background) and electrophoresed on an agarose gel. The vector fragment can be eluted from the gel using the Geneclean kit (Bio 101). For larger scale preparations, potassium acetate gradients are used to purify vector fragment.

a. Procedure for Purification of Vector for Library Construction

1. Digest 200 µg of pJS142 DNA to completion in 1 ml final volume with SfiI followed by EagI.

2. In a ½"×2" ultraclear centrifuge tube, carefully layer 5%, 10%, 15%, and 20% potassium acetate solutions containing 1 mM EDTA and 2 µg/ml ethidium bromide, using 1 ml of each.

3. Layer 1 ml of the digest on top of the gradient. Centrifuge at 48,000 rpm for 3 hrs in a Beckman SW50.1 rotor. The large vector fragment will migrate to a position ~⅔ of the distance from the top of the gradient as visualized with a long wave UV source. The small stuffer fragment remains at the top of the gradient while undigested supercoiled DNA forms a pellet on the bottom of the tube.

4. Puncture the tube with an 18 g syringe needle attached to a 3 ml syringe and extract the fragment (~0.5 to 1.0 ml).

5. Remove the ethidium by extracting five times with an equal volume of water saturated 1-butanol.

6. Transfer to a microfuge tube, add ¹/₁₀ volume 5M NaCl, and then an equal volume of isopropanol. Centrifuge at top speed for 10 min, pour off the liquid, and wash once with 80% ethanol.

7. Resuspend the pellet in water or TE and determine the concentration by reading $A_{260}$. The yield from the gradient is usually about 40% of the input amount.

b. Procedure for Library Construction

Three oligos are needed for library construction, ON-829 (5' ACC ACC TCC GG), ON-830 (5' TTA CTT AGT TA), and a library specific oligo of sequence (5' GA GGT GGT {NNK}$_n$ TAA CTA AGT AAA GC [SEQ ID NOS.85 and 86]), where {NNK}$_n$ denotes a random region of the desired length and sequence. The oligos can be 5'-phosphorylated chemically during synthesis or after purification with polynucleotide kinase. They are then annealed at a 1:1:1 molar ratio and ligated to the vector. Note that the melting temperature of the annealed oligo complex is quite low, so the final annealed mixture should never be warmed above the 14° C. ligation temperature.

1. Mix phosphorylated ON-829, ON-830, and the library oligo (50 pm each), 1 µl 5M NaCl, 2.5 µl 1M Tris, pH 7.4, and dH$_2$O to bring the total volume to 50 µl.

2. Heat to 70° C. for 5 min in a temp block and then turn off the block and allow the mixture to cool slowly to around 30° C. Move the whole temp block into a 4° room or refrigerator and allow it to cool to below 10°, then move the samples onto ice.

3. Mix on ice: 5 µg (1.3 picomole) pJS142 fragment, 2.6 µl (2.6 picomole) annealing mix, 25 µl 10× ligase buffer, dH$_2$O to 250 µl, mix, then add 2 µl (800 NEB cohesive end units) T4 ligase. In parallel, set up a 1/10 scale no oligo control to check for background. Incubate at 14° C. for 12–24 hours.

4. Heat to 65° C., 10 min to inactivate the ligase. Add 2 µl 25 mM DNTP mixture (Pharmacia), 1 µl (13 units) Sequenase 2.0 (US Biochemicals). Add 1/10 amounts to the control legation determine ligation efficiency compared to the control.

5. Add 250 µl H$_2$O, 55 µl 5M NaCl to the library. Extract with 300 µl phenol/CHCl3, spin 3 min, and move 500 µl of the aqueous phase to a new microfuge tube.

6. Add 1 µl 20 mg/ml glycogen (Boehringer Mannheim molecular biology grade) and 500 µl isopropanol. Mix well and spin in microfuge at top speed for 10 min.

7. Pour off the liquid, close the tube, and spin briefly. Use a fine bore pipet tip to remove the last traces of liquid without disturbing the pellet. Wash the pellet with 500 µl of 4° 80% ethanol, spin 2 min. Pour off the liquid, close the tube, and spin briefly. Use a fine bore pipet tip to remove the last traces of liquid. This careful washing procedure is important to remove all traces of salt to prevent problems during the electroporation step.

8. Resuspend the pellet in 4 µl dH$_2$O. Store at –20° until ready for amplification.

(4) Screening

The library can be screened over a two-day period as follows.

Day 1

1. Coat two sets of 12 microtiter wells with the appropriate amount of immobilizing antibody in 100 µl of PBS, for panning and negative control; let the coated plate incubate at 37° C. for 1 hr. Consider using all 24 wells as "plus receptor" wells in the first round, i.e., no negative control in the first round.

2. Wash the plate four times (4×) with HEK/BSA.

3. Block wells by adding 200 µl of HEK/BSA to each well; let the plate incubate at 37° C. for 1 hr.

4. Wash the plate 4× with HEK/BSA.

5. Dilute the receptor preparation in cold HEK/BSA (or appropriate binding buffer) as necessary.

6. Add the diluted receptor preparation to the wells at 100 µl per well; let the plate incubate at 4° C. for 1 hr. with agitation.

7. Wash the plate 2× with cold HEK/BSA.

8. Add 100 µl of 0.1 mg/ml bulk DNA in HEK/BSA to each well; incubate the plate at 4° C. for at least 10 minutes.

On day 1, steps A-O can also be carried out. Note that the column separation (steps A and H-O is optional). If the column separation is omitted, the lysates from step G are added directly to the wells.

A. Begin equilibrating column 22 mm diameter×22 cm height of Sephacryl S-400) with cold HEKL (~1 hr, flow rate is set to collect 5 ml fractions every 2 to 3 minutes).

B. Prepare 1 ml of lysozyme at 10 mg/ml in cold HE.

C. Thaw and combine sub-libraries (2 ml total volume) in a 13 ml Sarstedt screw cap tube.

D. Add 6 ml of lysis buffer and 150 µl lysozyme solution (Boehringer lysozyme is preferred over Sigma lysozyme); mix by inverting gently; and incubate on ice for 5 minutes, although less time is often satisfactory.

E. Add 2 ml of 20% lactose (lacI libraries only) and 250 µl of 2M KCl (200 µl, for headpiece dimer libraries), and mix by inverting gently.

F. Spin at 14.5K for 15 minutes.

G. Transfer supernatant by pipetting into a new tube.

H. Load raw lysate onto the equilibrated column.

I. After lysate is loaded, collect ten 5 ml fractions.

J. Perform the coomassie protein assay as follows: (1) to 10 microtiter wells, add 100 µl of coomassie reagent and 20 µl from each fraction, and mix; (2) select 4 consecutive fractions which correspond to 1 brown and 3 blue wells from the assay (light blue counts as blue).

K. Combine selected fractions in a Centriprep100. Two centripreps may be used to speed up the process. The maximum capacity of each centriprep is about 15 ml.

L. Spin in J-6B centrifuge at 1500 rpm.

M. Rinse the column with cold HEK for 1 hr.

N. Empty liquid from the inner chamber every 15 minutes until final volume <2 ml (~1 hr.).

O. Determine lysate volume, and remove 1% as "Pre" sample; keep Pre sample on ice.

Returning to the numbered steps, one proceeds as follows.

9. Wash plate 2× with cold HEK/BSA.

10. Bring the volume of the concentrated lysate up to 2400 µl by adding HEKL/BSA; add bulk DNA to a final concentration of 0.1 mg/ml. The activity of the receptor in this buffer should be verified.

11. Add lysate at 100 µl per well; incubate the plate at 4° C. for 1 hr. with agitation.

12. Wash plate 4× with cold HEKL/BSA.

13. Add 100 µl of 0.1 mg/ml bulk DNA in HEKL/BSA to each well; incubate at 4° C. for 30 minutes with agitation.

14. Wash plate 4× with cold HEKL.

15. Quickly wash plate 1× with cold HEK.

16. Elute by adding to each well 50 µl 10 mM Tris pH 8, 1 mM EDTA, 0.5M NaCl, then add 50 µl equilbrated phenol, and agitate for 5 min.

17. Remove all eluants; centrifuge to separate phases, remove acqueous phase to a new tube.

18. Add one-tenth volume of 5M NaCl and 1 µl of 20 mg/ml glycogen as carrier.

19. Precipitate plasmids in equal volume of isopropanol at room temperature.

20. Spin 10 minutes; carefully remove supernatant, spin again, and remove remaining supernatant.

21. Wash with 200 μl of cold 70% EtOH.

22. Spin and remove traces of supernatant as above.

23. Resuspend plasmids in water (suggested volumes: 100 μl for Pre; and 4 μl each for the panning and negative control wells; use more than 4 μl for panning and negative control samples in later rounds to retain as backups).

Day 2

24. Chill 4 sterile 0.2 cm electrode gap cuvettes on ice. The panning sample is divided equally into 2 cuvettes to prevent complete loss of sample during electroporation.

25. To three 16 ml sterile culture tubes, add 1 ml SOC medium (2% Bacto-Tryptone, 0.5% Bacto-yeast extract, 10 mM NaCl, 2.5 mM KCl, 10 mM $MgCl_2$, 10 mM $MgSO_4$, and 20 mM Glucose) to two tubes and 2 ml to one tube. Label the two 1 ml tubes as "Pre" and "NC" (for "negative control"), and label the 2 ml tube as "Pan" (for "panning").

26. Thaw 200 μl of high efficiency electro-competent cells.

27. Transfer 40 μl aliquots of cells to 4 chilled sterile eppendorf tubes; incubate the tubes on ice.

28. Add 2 μl of each plasmid to each tube and mix gently.

29. Transfer cells/plasmids mixtures into their corresponding cuvettes; keep the cuvettes on ice.

30. Set the Gene Pulser apparatus to 2.5 kV, 25 μF capacity, and set the Pulser Controller unit to 200 ohms.

31. Apply one pulse (time constant=4–5 msec).

32. Immediately add the room temperature SOC medium to resuspend cells in the cuvette.

33. Transfer cell suspension back to the culture tube.

34. Incubate the culture tube at 37° C. for 1 hr. with agitation.

35. To 200 ml of LB broth prewarmed to 37° C., add 0.4 ml of 50 mg/ml ampicillin.

36. Remove 10 to 100 μl of the "Pan" library culture for plating, and transfer the rest (2 ml) to the prewarmed LB broth. Plate out several dilutions of each sample on LB plates containing ampicillin. Suggested plate dilutions are as follows: Pre—$10^{-5}$, $10^{-6}$ and $10^{-7}$; and Pan/NC—$10^{-3}$, $10^{-4}$, $10^{-5}$ and $10^{-6}$.

37. Grow "Pan" library at 37° C. for about 4–5 hr. until the $OD_{600}$=0.5–1.0.

38. Chill the flask rapidly in ice water for at least 10 minutes.

39. Centrifuge cells in 250 ml sterile bottle at 6K for 6 minutes, Backman JA-14 rotor.

40. Wash by vortexing cells in 100 ml of cold WTEK.

41. Centrifuge at 6K for 6 minutes.

42. Wash by vortexing cells in 50ml cold TEK.

43. Centrifuge at 6K for 6 minutes.

44. Resuspend cells in 4 ml of HEK and store in two 2 ml vials at −70° C. Use one tube for the next round; keep the other as a backup.

(5) Examination of Individual Clones by ELISA

The binding properties of the peptides encoded by individual clones are typically examined after 3, 4, or 5 rounds of panning, depending on the enrichment numbers observed. The most sensitive assay is an ELISA that detects receptor specific binding by lacI-peptide fusion proteins. The lacI ELISA can detect binding of peptides that have monovalent affinities for the receptor as low as ~100 μM. This sensitivity of the assay is an advantage in that initial hits of low affinity can be easily identified, but is a disadvantage in that the signal in the ELISA is not correlated with the intrinsic affinity of the peptides. Fusion of the peptides to the maltose binding protein (MBP) as described below permits testing in a ELISA where signal strength is better correlated with affinity.

a. Reagents for Lysates

Lysis Buffer (make fresh just before use)
  42 ml HE
  5 ml 50% glycerol
  3 ml 10 Mg/ml BSA, protease free, in HE 125 μl 0.1M pMSF (may include other protease inhibitors)
  750 μl 10 mg/ml lysozyme in HE 20% L-arabinose in $dH_2O$, sterile (Important: do not use D-arabinose)

b. Procedure for the Preparation of lacI ELISA Lysates

1. Inoculate each individual clone in 1 ml LB-Amp, shake at 37° C., overnight.

2. Dilute 300 μl of the culture into 3 ml LB-Amp, shake at 37° C. for 1 hr.

3. Induce with 33 μl of 20% L-arabinose (0.2% final), shake at 37° C. for 2–3 hrs.

4. Spin at 4,000 rpm, 5 min, Beckman JS 4.2 rotor.

5. Decant supernatant, keep cells on ice or at 4° C. for the rest of the procedure.

6. Vortex to resuspend cells in 3 ml 4° C. WTEK buffer.

7. Spin 4,000 rpm, 5 min, pour off supernatant.

8. Vortex to resuspend cells in 1 ml 4° C. TEK buffer; transfer to 1.5 ml microfuge tubes.

9. Spin 14,000 rpm, 2 min, aspirate supernatant.

10. Resuspend cells in 1 ml lysis buffer, incubate on ice, 1 hr.

11. Add 110 μl 2M KCl (final concentration of 0.2M) to solubilize fusion proteins, invert to mix. Note that most of the lacI protein will be present as insoluble inclusion bodies that will be part of the pellet discarded in step 13. Enough lacI protein is soluble to allow a strong signal in the ELISA. The KCl helps increase the amount of soluble lacI.

12. Spin 14,000 rpm, 15 min, 4° C. in a microfuge.

13. Transfer ~900 μl of the clear crude lysate to a new tube. (Store at −70° C. if assay is to be done on another day.)

c. Reagents for ELISA

PBT: PBS, 1% BSA, 0.05% Tween-20

PBS/Tween: PBS, 0.05% Tween-20

Anti-lacI antibody: Rabbit anti-lacI polyclonal can be purchased from Stratagene (#217449).

Goat anti-Rabbit IgG and light chains, alkaline phosphatase conjugate is from Tago (#6500).

Alkaline phosphatase substrate is p-nitrophenyl phosphate.

Development buffer: 9.6% diethanolamine, 0.24 mM $MgCl_2$, pH 9.8 with HCl.

d. Procedure for lacI ELISA

1. Coat microtiter wells with the receptor of interest. Make equivalent set of minus receptor control wells in parallel. Block wells for at least 1 hr with 1% BSA. The control wells should be as similar as possible to the receptor coated wells to control for various sorts of nonspecific binding by the peptides. The assay is usually performed in duplicate or triplicate wells.

2. Wash plate 4× with 4° C. PBS/Tween.

3. Add 100 μl/well crude lysate diluted 1/20 in PBT; 4° C., 30 min, shake gently.

4. Wash plate 4× with 4° C. PBS/Tween.

5. Add 100 l/well anti-lacI Antibody diluted 1/15,000 in PBT; 4° C., 30 min, shake gently. The dilution of anti-lacI given here is based on our titration of our own serum. It may be necessary to use a different dilution of the commercially available serum.

6. Wash plate 4× with 4° C. PBS/Tween.

7. Add 100 µl/well goat anti-rabbit alkaline phosphatase conjugated Ab diluted 1/3,000 in PBT; 4° C., 30 min, shake gently.

8. Wash plate 4× with 4° C. PBS/Tween.

9. Wash plate 2× with 4° C. TBS (10 mM Tris pH 7.5, 150 mM NaCl).

10. Develop assay, @200 µl/well of 1 mg/ml alkaline phosphatase substrate in development buffer.

11. Read plate at $A_{405}$ in microtiter plate reader. (Take time point measurements to determine termination time. Reaction is no longer linear above $A_{405}$~1.0.)

12. Stop reaction with 50 µl/well 2M NaOH and read final result.

e. Transfer of selected sequences to maltose binding protein (MBP)

Coding sequences of interesting single clones or populations of clones are often transferred to vectors that fuse those sequences in frame with the gene encoding MBP. This is done for several reasons. First, MBP generally exists in solution as a monomer and the native protein has no cysteine residues. The monovalency of peptide display allowed by MBP fusions causes the MBP ELISA described below to be much more affinity sensitive than the lacI ELISA. Dimers forms have been reported for MBP purified under certain conditions. These dimers can be dissociated by the addition of maltose to the solution. No substantial difference in the MBP ELISA signal is seen in the presence and absence of 1 mM maltose using the protocols listed here, so dimer formation under our conditions appears unlikely.

The second reason for using MBP is that it can be expressed in very large amounts as a soluble protein which is easily purified, allowing initial examination of the properties of peptides without the need for chemical synthesis. Third, the MBP fusion proteins can be directed to either the cytoplasm (a reducing environment) or the periplasm (an oxidizing environment) of E. coli using vectors that differ only by the presence or absence of an N-terminal signal sequence in the gene encoding MBP. Some peptides are expressed more efficiently in one or the other of these two environments. Fourth, peptide populations linked to MBP can be easily screened using colony lifts with a selected receptor.

The cloning of a library into pJS142 creates a BspEI restriction site near the beginning of the random coding region of the library. Digestion with BspEI and ScaI allows the purification of a ~900 bp DNA fragment that can be subcloned into one of two vectors, pELM3 (cytoplasmic) or pELM15 (periplasmic), which are simple modifications of the pMALc2 and pMALp2 vectors, respectively, available commercially from New England Biolabs. Digestion of pELM3 and pELM15 with AgeI and ScaI allows efficient cloning of the BspEI-ScaI fragment from the pJS142 library. The BspEI and AgeI ends are compatible for ligation. In addition, correct ligation of the ScaI sites is essential to recreate a functional bla (Amp resistance) gene, thus lowering the level of background clones from undesired ligation events. Expression of the tac promoter-driven MBP-peptide fusions can then be induced with IPTG.

f. Procedure for Subcloning into MBP Vectors

1. Digest pELM3 or pELM15 with AgeI and ScaI. Purify the 5.6 kb fragment away from the 1.0 kb fragment. The digest is generally run in a 0.7% agarose gel, and the appropriate region of the ethidium bromide stained gel excised under low-intensity long wave UV illumination, and run on a new gel. Electrophoresis in the second gel yields an additional purification of the desired fragment and leads to lower background in the ligation. Elute the DNA from the gel fragment using a Geneclean kit (Bio 101).

2. Remove a 5–50 ml portion from the 200 ml PAN amplification culture before harvesting the cells. Allow the removed portion to grow to saturation overnight. Prepare DNA from the cells and digest with BspEI and ScaI. Purify the 0.9 kb BspEI-ScaI fragment from the 3.1 and 1.7 kb vector fragments as described above.

3. Ligate an equimolar mix of the two fragments at a final DNA concentration of ~50 µg/ml with T4 DNA ligase in standard ligase buffer containing 0.4 mM ATP (the higher levels of ATP found in most ligase buffers inhibit efficient ligation of the ScaI blunt ends). Incubate at 14° C. overnight.

4. Inactivate ligase at 65° C. for 10 min. To lower background from religation of the parental vector, digest the ligation mix with XbaI. Isopropanol-precipitate the ligation mix using 1 µl of glycogen as carrier, wash carefully with 80% ethanol, and resuspend the dry pellet in 20 µl dH$_2$O. Transform ARI 814 with 1 µl, and plate on LB-Amp plates.

g. Procedure for MBP ELISA

The cell lysates for the MBP ELISA are prepared by the same procedure as the lacI ELISA lysates, except that the induction is done with a final concentration of 0.3 mM TG instead of L-arabinose. The ELISA is performed as described for lacI above with the following exceptions:

1. Lysates are diluted 1/50 for addition to the wells.

2. Primary antibody is 1/10,000 diluted polyclonal rabbit anti-MBP (available from New England Biolabs). Incubation is for 15 instead of 30 min.

3. The secondary antibody incubation is also for 15 instead of 30 min.

4. Development of the assay generally takes longer than the lacI ELISA, generally 30–60 min.

Although the foregoing invention has been described in some detail by way of illustration and example for purposes of clarity of understanding, it will be apparent that certain changes and modifications may be practiced within the scope of the appended claims.

The cell lines described in the application as having been deposited at the ATCC will be maintained at an authorized depository and replaced in the event of mutation, nonviability or destruction for a period of at least five years after the most recent request for release of a sample was received by the depository, for a period of at least thirty years after the date of the deposit, or during the enforceable life of the related patent, whichever period is longest. All restrictions on the availability to the public of the cell lines will be irrevocably removed upon the issuance of a patent from the above-captioned application.

What is claimed is:

1. A method of isolating a DNA binding protein comprising:
   (a) providing a recombinant DNA vector comprising a coding sequence for a peptide having a specific affinity for a receptor;
   (b) inserting a library of oligonucleotides encoding different potential DNA binding proteins into multiple copies of the recombinant DNA vector in-frame with the peptide coding sequence to form a library of different vectors encoding different fusion proteins, the fusion proteins differing in the potential DNA binding proteins;
   (c) transforming host cells with the library of different vectors to form transformed host cells;
   (d) culturing the transformed host cells under conditions suitable for expression of the fusion proteins, whereby, if a fusion protein comprises a potential DNA binding protein with affinity for a vector encoding the fusion protein, the fusion protein binds to the vector to form a complex;
   (e) lysing the transformed host cells under conditions such that complexes formed in (d) remain associated;
   (f) contacting the complexes with a receptor under conditions conducive to specific binding of the peptide to the receptor;
   (g) isolating complexes bound to the receptor, the complexes containing vectors encoding DNA binding proteins.

2. The method of claim 1, further comprising isolating the vectors from the complexes in (g), and repeating (c)–(g).

3. The method of claim 2, further comprising determining the sequence of a DNA binding protein encoded by a vector in (g).

4. The method of claim 3, further comprising:
   transforming the vectors in (g) into host cells under conditions suitable for expression of the fusion protein encoded by the vector, whereby the fusion protein binds to the vector to form a complex;
   lysing the transformed host cells under conditions such that the complex remains associated;
   contacting separate samples of the complex to the receptor and to a receptor lacking affinity for the peptide under conditions conducive to specific binding of the peptide to the receptor;

isolating vector from: (1) complex bound to the receptor and (2) complex bound to the receptor lacking affinity for the peptide;

separately transforming vector obtained from (1) and (2) and calculating an enrichment ratio equal to number of transformants from (1) divided by number of transformants from (2), the enrichment ratio being a measure of the suitability of the DNA binding protein for displaying the peptide for specific binding to the receptor.

5. The method of claim 1, wherein the potential DNA binding proteins in step (b) have at least 80% sequence identity to a natural DNA binding protein.

6. The method of claim 5, wherein the natural DNA binding protein is a lac repressor protein.

7. The method of claim 6, wherein the vector lacks a lacO site.

8. The method of claim 7, wherein the potential DNA binding proteins have at least 80% sequence identity to a headpiece dimer comprising two lac headpieces joined by a linker.

9. The method of claim 1, further comprising contacting the complexes formed in step (d) with bulk DNA to compete with the binding of the fusion protein to the vector encoding the fusion protein.

10. A method of constructing a random peptide library comprising:

(a) providing a recombinant DNA vector that encodes a DNA binding protein other than a phage coat protein;

(b) inserting into the coding sequence of the DNA binding protein a coding sequence for a random peptide such that the resulting vectors encode fusion proteins, each of which comprises the DNA binding protein and a random peptide;

(c) transforming host cells with the vectors; and (d) culturing the transformed host cells under conditions suitable for expression of the fusion proteins, wherein the fusion proteins bind via the DNA binding protein to the vector with sufficient stability that complexes having a random peptide with a specific affinity for a receptor can be enriched by affinity purification on the receptor from complexes lacking a random peptide with a specific affinity for the receptor.

11. The method of claim 10, wherein the DNA binding protein is a non-sequence-specific DNA binding protein.

12. A method for screening a random peptide library for a peptide with specific affinity for a receptor, comprising:

(a) providing a peptide library wherein each member is a host cell transformed with a recombinant DNA vector that encodes a fusion protein comprising a DNA binding protein and a coding sequence for a random peptide, wherein members differ from other members with respect to the sequence of the random peptide, wherein the fusion proteins can bind via the DNA binding protein to the vector to form complexes having sufficient stability that complexes having a random peptide with a specific affinity for a receptor can be enriched by affinity purification to the receptor from complexes lacking a random peptide with a specific affinity for the receptor;

(b) lysing the cells transformed with the random peptide library under conditions such that the fusion protein remains bound to the vector that encodes the fusion protein;

(c) contacting the fusion proteins of the random peptide library with a receptor under conditions conducive to specific peptide-receptor binding; and (d) isolating the vector that encodes a random peptide that binds to said receptor.

13. The method of claim 12, wherein the DNA binding protein has been isolated by the method of claim 1.

14. The method of claim 13, wherein the DNA binding protein is a non-sequence-specific DNA binding protein.

15. The method of claim 13, wherein the vector lacks a lacO site.

16. The method of claim 13, wherein the recombinant vector further comprises a DNA sequence with a specific affinity for the DNA binding protein.

17. The method of claim 12, wherein the host cells are bacteria.

18. The method of claim 17, wherein the bacteria are *E. coli*, and the vector is a plasmid.

19. The method of claim 18, wherein the DNA binding protein is a lac repressor protein comprising two lac headpieces joined by a first linker and the DNA binding protein is joined to the random peptide by a second linker.

20. The method of claim 19, wherein the first linker is GRCR (SEQ ID No: 109), the two lac headpieces are designated A4.5 in FIG. 6 (SEQ ID Nos: 99 and 100) and the second linker is RSQE (amino acids 1–4 of SEQ ID No: 119).

21. The method of claim 19, wherein the first linker is GRCR (SEQ ID No: 109), the two lac headpieces are designated B4.5 in FIG. 6 (SEQ ID Nos: 103 and 104), and the second linker is GPNQ (amino acids 1–4 of SEQ ID No: 110).

22. The method of claim 12, wherein the random peptide is located at the carboxy terminus of said fusion protein.

23. The method of claim 12, wherein the library has at least $10^6$ different members.

24. The method of claim 12 further comprising:

(e) transforming a host cell with the vectors obtained in (d); and repeating (b), (c), and (d) with the host cells transformed in (e).

25. A recombinant DNA vector for constructing the random peptide library of claim 10, said vector comprising:

(a) a DNA sequence encoding the DNA binding protein;

(b) a promoter positioned so as to drive transcription of the DNA binding protein coding sequence;

(c) a coding sequence for a peptide inserted in the DNA binding protein coding sequence so that the coding sequences can be transcribed to produce an RNA transcript that can be translated to produce a fusion protein capable of binding to at least one DNA sequence in the vector.

26. A host cell transformed with the vector of claim 25.

27. A random peptide library comprising at least $10^6$ different members, wherein each member is a host cell transformed with a recombinant DNA vector that encodes a fusion protein comprising a DNA binding protein other than a phage coat protein and a random peptide; and wherein members differ from other members with respect to the sequence of the random peptide, wherein the fusion proteins can bind via the DNA binding protein to the vector to form complexes having sufficient stability that complexes having a random peptide with a specific affinity for a receptor can be enriched by affinity purification to the receptor from complexes lacking a random peptide with a specific affinity for the receptor.

* * * * *

SEQUENCE LISTING ( 1 ) GENERAL INFORMATION:

( i i i ) NUMBER OF SEQUENCES: 162

( 2 ) INFORMATION FOR SEQ ID NO:1:

( i ) SEQUENCE CHARACTERISTICS:
      ( A ) LENGTH: 14 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:1:

```
Gly Ala Xaa Xaa Xaa Xaa Xaa Xaa Xaa Xaa Xaa Xaa Xaa Xaa
 1           5                           10
```

( 2 ) INFORMATION FOR SEQ ID NO:2:

( i ) SEQUENCE CHARACTERISTICS:
      ( A ) LENGTH: 54 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:2:

GTGGCGCCNN KNNKNNKNNK NNKNNKNNKN NKNNKNNKNN KNNKTAAGGT CTCG          54

( 2 ) INFORMATION FOR SEQ ID NO:3:

( i ) SEQUENCE CHARACTERISTICS:
      ( A ) LENGTH: 11 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:3:

TGCCACCGCG G          11

( 2 ) INFORMATION FOR SEQ ID NO:4:

( i ) SEQUENCE CHARACTERISTICS:
      ( A ) LENGTH: 14 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:4:

ATTCCAGAGC TCGA          14

( 2 ) INFORMATION FOR SEQ ID NO:5:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( i i ) MOLECULE TYPE: Peptide ( x i ) SEQUENCE DESCRIPTION: SEQ ID NO:5:

```
        Leu Glu Ser Gly Gln Gly Ala Asp Gly Ala
        1               5                   10
```

( 2 ) INFORMATION FOR SEQ ID NO:6:

( i ) SEQUENCE CHARACTERISTICS:
        ( A ) LENGTH: 45 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:6:

```
CTCGAGAGCG GGCAGGGGGC CGACGGGGCC TAATTAATTA AGCTT          45
```

( 2 ) INFORMATION FOR SEQ ID NO:7:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: dynB 1.0

( x i ) SEQUENCE DESCRIPTION: SEQ ID NO:7:

```
    Tyr Gly Gly Phe Leu Arg Arg Gln Phe Lys Val Val Thr
    1               5                   10
```

( 2 ) INFORMATION FOR SEQ ID NO:8:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: 21 4 1.2

( x i ) SEQUENCE DESCRIPTION: SEQ ID NO:8:

```
    Thr Gly Lys Arg Gly Phe Lys Val Val Cys Asn Ser
    1               5                   10
```

( 2 ) INFORMATION FOR SEQ ID NO:9:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: 22 4 1.2

( x i ) SEQUENCE DESCRIPTION: SEQ ID NO:9:

```
    Lys Arg Asn Phe Lys Val Val Gly Ser Pro Cys Gly
    1               5                   10
```

( 2 ) INFORMATION FOR SEQ ID NO:10:

( i ) SEQUENCE CHARACTERISTICS:

(A) LENGTH: 28 amino acids
(B) TYPE: amino acid
(C) STRANDEDNESS: single
(D) TOPOLOGY: linear (ii) MOLECULE TYPE: peptide (vii) IMMEDIATE SOURCE:
(B) CLONE: 10 4 0.3

(xi) SEQUENCE DESCRIPTION: SEQ ID NO:10:

Ser Asp Ser Gly Asn Gly Leu Gly Ile Arg Arg Phe Lys Val Ser Ser
1               5                   10                  15

Leu Ala Val Leu Ala Asp Glu Arg Arg Phe Ser Ala
            20                  25

(2) INFORMATION FOR SEQ ID NO:11:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (vii) IMMEDIATE SOURCE:
(B) CLONE: 30 4 0.9

(xi) SEQUENCE DESCRIPTION: SEQ ID NO:11:

Gly Thr Arg Pro Phe Lys Val Ser Glu Tyr Ile Leu
1               5                   10

(2) INFORMATION FOR SEQ ID NO:12:

(i) SEQUENCE CHARACTERISTICS:
(A) LENGTH: 28 amino acids
(B) TYPE: amino acid
(C) STRANDEDNESS: single
(D) TOPOLOGY: linear (ii) MOLECULE TYPE: peptide (vii) IMMEDIATE SOURCE:
(B) CLONE: 35 4 0.2

(xi) SEQUENCE DESCRIPTION: SEQ ID NO:12:

Ser Leu Lys Asp Glu Asn Asn Lys Arg Arg Ile Phe Lys Val Ser Ser
1               5                   10                  15

Leu Ala Val Leu Ala Asp Glu Arg Arg Phe Ser Ala
            20                  25

(2) INFORMATION FOR SEQ ID NO:13:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (vii) IMMEDIATE SOURCE:
(B) CLONE: 57 3 0.9

(xi) SEQUENCE DESCRIPTION: SEQ ID NO:13:

Ser Tyr Leu Arg Arg Glu Phe Lys Val Ser Gly Val
1               5                   10

(2) INFORMATION FOR SEQ ID NO:14:

(  i  ) SEQUENCE CHARACTERISTICS:
   ( A ) LENGTH: 12 amino acids
   ( B ) TYPE: amino acid
   ( C ) STRANDEDNESS: single
   ( D ) TOPOLOGY: linear ( i i ) MOLECULE TYPE: peptide ( v i i ) IMMEDIATE SOURCE:
   ( B ) CLONE: 24 4 0.9

( x i ) SEQUENCE DESCRIPTION: SEQ ID NO:14:

Gly Trp Arg Ser Cys Pro Arg Gln Phe Lys Val Thr
1               5                   10

( 2 ) INFORMATION FOR SEQ ID NO:15:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( v i i ) IMMEDIATE SOURCE:
      ( B ) CLONE: 45 3 0.9

( x i ) SEQUENCE DESCRIPTION: SEQ ID NO:15:

Ile Lys Arg Gly Phe Lys Ile Thr Ser Ala Met Ser
1               5                   10

( 2 ) INFORMATION FOR SEQ ID NO:16:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( v i i ) IMMEDIATE SOURCE:
      ( B ) CLONE: 47 3 0.8

( x i ) SEQUENCE DESCRIPTION: SEQ ID NO:16:

Val Arg Phe Ile Ala Arg Pro Phe Arg Ile Thr Gly
1               5                   10

( 2 ) INFORMATION FOR SEQ ID NO:17:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( v i i ) IMMEDIATE SOURCE:
      ( B ) CLONE: 71 2 1.1

( x i ) SEQUENCE DESCRIPTION: SEQ ID NO:17:

Ala Arg Ala Phe Arg Val Thr Arg Ile Ala Gly Val
1               5                   10

( 2 ) INFORMATION FOR SEQ ID NO:18:

( i ) SEQUENCE CHARACTERISTICS:
      ( A ) LENGTH: 12 amino acids
      ( B ) TYPE: amino acid (C) STRANDEDNESS: single
(D) TOPOLOGY: linear (ii) MOLECULE TYPE: peptide (vii) IMMEDIATE SOURCE:
(B) CLONE: 74 2 0.2

(xi) SEQUENCE DESCRIPTION: SEQ ID NO:18:

```
Lys Asn Glu Thr Arg Arg Pro Phe Arg Gln Thr Ala
1               5                   10
```

(2) INFORMATION FOR SEQ ID NO:19:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (vii) IMMEDIATE SOURCE:
(B) CLONE: 68 2 0.6

(xi) SEQUENCE DESCRIPTION: SEQ ID NO:19:

```
Val Asn His Arg Arg Phe Ser Val Val His Ser Tyr
1               5                   10
```

(2) INFORMATION FOR SEQ ID NO:20:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (vii) IMMEDIATE SOURCE:
(B) CLONE: 48 3 0.4

(xi) SEQUENCE DESCRIPTION: SEQ ID NO:20:

```
Val Ser Ser Ser Arg Thr Phe Asn Val Thr Arg Arg
1               5                   10
```

(2) INFORMATION FOR SEQ ID NO:21:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (vii) IMMEDIATE SOURCE:
(B) CLONE: 46 3 0.3

(xi) SEQUENCE DESCRIPTION: SEQ ID NO:21:

```
Gly Arg Ser Phe His Val Thr Ser Phe Gly Ser Val
1               5                   10
```

(2) INFORMATION FOR SEQ ID NO:22:

(i) SEQUENCE CHARACTERISTICS:
(A) LENGTH: 12 amino acids
(B) TYPE: amino acid
(C) STRANDEDNESS: single
(D) TOPOLOGY: linear (ii) MOLECULE TYPE: peptide (vii) IMMEDIATE SOURCE:
      (B) CLONE: 4 4 1.1

(xi) SEQUENCE DESCRIPTION: SEQ ID NO:22:

Arg Ser Thr Thr Val Arg Gln His Lys Val Val Gly
1               5                       10

(2) INFORMATION FOR SEQ ID NO:23:

(i) SEQUENCE CHARACTERISTICS:
       (A) LENGTH: 12 amino acids
       (B) TYPE: amino acid
       (C) STRANDEDNESS: single
       (D) TOPOLOGY: linear (ii) MOLECULE TYPE: peptide (vii) IMMEDIATE SOURCE:
         (B) CLONE: 15 4 1.2

(xi) SEQUENCE DESCRIPTION: SEQ ID NO:23:

Glu Arg Pro Asn Arg Leu His Lys Val Val His Ala
1               5                       10

(2) INFORMATION FOR SEQ ID NO:24:

(i) SEQUENCE CHARACTERISTICS:
       (A) LENGTH: 12 amino acids
       (B) TYPE: amino acid
       (C) STRANDEDNESS: single
       (D) TOPOLOGY: linear (ii) MOLECULE TYPE: peptide (vii) IMMEDIATE SOURCE:
         (B) CLONE: 73 2 0.5

(xi) SEQUENCE DESCRIPTION: SEQ ID NO:24:

Trp Gln Asn Arg Thr His Lys Val Val Ser Gly Arg
1               5                       10

(2) INFORMATION FOR SEQ ID NO:25:

(i) SEQUENCE CHARACTERISTICS:
       (A) LENGTH: 7 amino acids
       (B) TYPE: amino acid
       (C) STRANDEDNESS: single
       (D) TOPOLOGY: linear (ii) MOLECULE TYPE: peptide (vii) IMMEDIATE SOURCE:
         (B) CLONE: 78 2 1.1

(xi) SEQUENCE DESCRIPTION: SEQ ID NO:25:

Ala Arg Lys His Lys Val Thr
1               5

(2) INFORMATION FOR SEQ ID NO:26:

(i) SEQUENCE CHARACTERISTICS:
       (A) LENGTH: 11 amino acids
       (B) TYPE: amino acid
       (C) STRANDEDNESS: single
       (D) TOPOLOGY: linear (ii) MOLECULE TYPE: peptide (vii) IMMEDIATE SOURCE:
         (B) CLONE: 40 3 1.1

( x i ) SEQUENCE DESCRIPTION: SEQ ID NO:26:

Arg Gln Val Thr Arg Leu His Lys Val Ile His
1               5                   10

( 2 ) INFORMATION FOR SEQ ID NO:27:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: 11 4 1.0

( x i ) SEQUENCE DESCRIPTION: SEQ ID NO:27:

Cys Pro Gly Glu Arg Met His Lys Ala Val Arg Ala
1               5                   10

( 2 ) INFORMATION FOR SEQ ID NO:28:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: 2 4 1.0

( x i ) SEQUENCE DESCRIPTION: SEQ ID NO:28:

Ser Arg Cys Arg Asn His Arg Val Val Thr Ser Gln
1               5                   10

( 2 ) INFORMATION FOR SEQ ID NO:29:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: 26 4 0.8

( x i ) SEQUENCE DESCRIPTION: SEQ ID NO:29:

Asn Asp Gly Arg Pro His Arg Val Val Arg Cys Gly
1               5                   10

( 2 ) INFORMATION FOR SEQ ID NO:30:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: 9 4 0.8

( x i ) SEQUENCE DESCRIPTION: SEQ ID NO:30:

Glu Ile Arg Arg His Arg Val Thr Glu Arg Val Asp
1               5                   10

( 2 ) INFORMATION FOR SEQ ID NO:31:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: 56 3 1.1

( x i ) SEQUENCE DESCRIPTION: SEQ ID NO:31:

```
Leu Arg Arg Leu His Arg Val Thr Asn Thr Met Thr
 1               5                  10
```

( 2 ) INFORMATION FOR SEQ ID NO:32:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: 69 2 1.1

( x i ) SEQUENCE DESCRIPTION: SEQ ID NO:32:

```
Val Lys Gln Arg Leu His Ser Val Val Arg Pro Gly
 1               5                  10
```

( 2 ) INFORMATION FOR SEQ ID NO:33:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: 7 4 1.1

( x i ) SEQUENCE DESCRIPTION: SEQ ID NO:33:

```
Val Thr Gln Arg Val Arg Ser Asn Lys Val Val Ser
 1               5                  10
```

( 2 ) INFORMATION FOR SEQ ID NO:34:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: 20 4 1.1

( x i ) SEQUENCE DESCRIPTION: SEQ ID NO:34:

```
His Val Glu Lys Ile Lys Arg Leu Asn Lys Val Val
 1               5                  10
```

( 2 ) INFORMATION FOR SEQ ID NO:35:

( i ) SEQUENCE CHARACTERISTICS:
   ( A ) LENGTH: 12 amino acids
   ( B ) TYPE: amino acid
   ( C ) STRANDEDNESS: single
   ( D ) TOPOLOGY: linear ( i i ) MOLECULE TYPE: peptide ( v i i ) IMMEDIATE SOURCE:
   ( B ) CLONE: 23 4 1.2

( x i ) SEQUENCE DESCRIPTION: SEQ ID NO:35:

Arg Leu Lys Thr Arg Leu Asn Lys Val Val Met Asp
1               5                   10

( 2 ) INFORMATION FOR SEQ ID NO:36:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( v i i ) IMMEDIATE SOURCE:
      ( B ) CLONE: 63 2 0.4

( x i ) SEQUENCE DESCRIPTION: SEQ ID NO:36:

Val Arg Met Asn Lys Val Val Cys Glu Lys Leu Trp
1               5                   10

( 2 ) INFORMATION FOR SEQ ID NO:37:

( i ) SEQUENCE CHARACTERISTICS:
      ( A ) LENGTH: 11 amino acids
      ( B ) TYPE: amino acid
      ( C ) STRANDEDNESS: single
      ( D ) TOPOLOGY: linear ( i i ) MOLECULE TYPE: peptide ( v i i ) IMMEDIATE SOURCE:
      ( B ) CLONE: 49 3 0.3

( x i ) SEQUENCE DESCRIPTION: SEQ ID NO:37:

Asp Leu Lys Arg Leu Asn Arg Val Val Gly His
1               5                   10

( 2 ) INFORMATION FOR SEQ ID NO:38:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( v i i ) IMMEDIATE SOURCE:
      ( B ) CLONE: 19 4 0.8

( x i ) SEQUENCE DESCRIPTION: SEQ ID NO:38:

Arg Ile Arg Asn Asn Lys Val Ile Ala Arg Pro Val
1               5                   10

( 2 ) INFORMATION FOR SEQ ID NO:39:

( i ) SEQUENCE CHARACTERISTICS:
      ( A ) LENGTH: 12 amino acids
      ( B ) TYPE: amino acid
      ( C ) STRANDEDNESS: single (D) TOPOLOGY: linear (i i) MOLECULE TYPE: peptide (v i i) IMMEDIATE SOURCE:
    (B) CLONE: 36 4 0.5

(x i) SEQUENCE DESCRIPTION: SEQ ID NO:39:

| Ser | Arg | Val | Arg | Ser | Asn | Lys | Val | Ile | Met | Ser | Ile |
|---|---|---|---|---|---|---|---|---|---|---|---|
| 1 | | | | 5 | | | | | 10 | | |

(2) INFORMATION FOR SEQ ID NO:40:

(i) SEQUENCE CHARACTERISTICS:
        (A) LENGTH: 12 amino acids
        (B) TYPE: amino acid
        (C) STRANDEDNESS: single
        (D) TOPOLOGY: linear (i i) MOLECULE TYPE: peptide (v i i) IMMEDIATE SOURCE:
        (B) CLONE: 77 2 0.6

(x i) SEQUENCE DESCRIPTION: SEQ ID NO:40:

| Ser | Cys | Arg | Leu | Asn | Lys | Val | Ile | Ala | Arg | Pro | Val |
|---|---|---|---|---|---|---|---|---|---|---|---|
| 1 | | | | 5 | | | | | 10 | | |

(2) INFORMATION FOR SEQ ID NO:41:

(i) SEQUENCE CHARACTERISTICS:
        (A) LENGTH: 12 amino acids
        (B) TYPE: amino acid
        (C) STRANDEDNESS: single
        (D) TOPOLOGY: linear (i i) MOLECULE TYPE: peptide (v i i) IMMEDIATE SOURCE:
        (B) CLONE: 33 4 0.5

(x i) SEQUENCE DESCRIPTION: SEQ ID NO:41:

| Arg | Ala | Leu | Ser | Lys | Asp | Arg | Leu | Asn | Lys | Val | Thr |
|---|---|---|---|---|---|---|---|---|---|---|---|
| 1 | | | | 5 | | | | | 10 | | |

(2) INFORMATION FOR SEQ ID NO:42:

(i) SEQUENCE CHARACTERISTICS:
        (A) LENGTH: 12 amino acids
        (B) TYPE: amino acid
        (C) STRANDEDNESS: single
        (D) TOPOLOGY: linear (i i) MOLECULE TYPE: peptide (v i i) IMMEDIATE SOURCE:
        (B) CLONE: 58 3 1.1

(x i) SEQUENCE DESCRIPTION: SEQ ID NO:42:

| Cys | Thr | Thr | Glu | Arg | Ser | Arg | Gln | Trp | Lys | Val | Thr |
|---|---|---|---|---|---|---|---|---|---|---|---|
| 1 | | | | 5 | | | | | 10 | | |

(2) INFORMATION FOR SEQ ID NO:43:

(i) SEQUENCE CHARACTERISTICS:
        (A) LENGTH: 12 amino acids
        (B) TYPE: amino acid
        (C) STRANDEDNESS: single
        (D) TOPOLOGY: linear (i i) MOLECULE TYPE: peptide ( v i i ) IMMEDIATE SOURCE:
        ( B ) CLONE: 16 4 1.1

( x i ) SEQUENCE DESCRIPTION: SEQ ID NO:43:

Ala Arg Pro Trp Lys Ile Thr Arg Asn Glu Pro Gly
1               5                   10

( 2 ) INFORMATION FOR SEQ ID NO:44:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: 72 2 0.3

( x i ) SEQUENCE DESCRIPTION: SEQ ID NO:44:

Gly Val Ser Glu Cys Arg Lys Trp Lys Ile Val Gln
1               5                   10

( 2 ) INFORMATION FOR SEQ ID NO:45:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: 6 4 1.2

( x i ) SEQUENCE DESCRIPTION: SEQ ID NO:45:

Thr Thr Leu Arg Arg Tyr Lys Val Thr Gly Glu Arg
1               5                   10

( 2 ) INFORMATION FOR SEQ ID NO:46:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: 34 4 1.1

( x i ) SEQUENCE DESCRIPTION: SEQ ID NO:46:

Ile Ala Asp Arg Arg Pro Tyr Arg Val Thr Arg Pro
1               5                   10

( 2 ) INFORMATION FOR SEQ ID NO:47:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: 76 2 1.2

( x i ) SEQUENCE DESCRIPTION: SEQ ID NO:47:

```
    Ala  Gly  Lys  Val  Leu  Arg  Ala  Tyr  Lys  Ile  Val  Glu
    1              5                        10
```

( 2 ) INFORMATION FOR SEQ ID NO:48:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: 8 4 1.0

( x i ) SEQUENCE DESCRIPTION: SEQ ID NO:48:

```
    Gln  Lys  Arg  Leu  Met  Lys  Val  Ile  Phe  Glu  Gly  Arg
    1              5                        10
```

( 2 ) INFORMATION FOR SEQ ID NO:49:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: 55 3 1.0

( x i ) SEQUENCE DESCRIPTION: SEQ ID NO:49:

```
    Glu  Val  Pro  His  Arg  Phe  Arg  Trp  Thr  Lys  His  Met
    1              5                        10
```

( 2 ) INFORMATION FOR SEQ ID NO:50:

( i ) SEQUENCE CHARACTERISTICS:
        ( A ) LENGTH: 24 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: 13 4 0.1

( x i ) SEQUENCE DESCRIPTION: SEQ ID NO:50:

```
    Ser  Thr  Thr  Glu  Arg  Arg  Ser  Phe  Lys  Val  Ser  Ser  Leu  Ala  Val  Leu
    1              5                        10                       15

Ala  Asp  Glu  Arg  Arg  Phe  Ser  Ala
                   20
```

( 2 ) INFORMATION FOR SEQ ID NO:51:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: 14 4 0.2

( x i ) SEQUENCE DESCRIPTION: SEQ ID NO:51:

```
Arg Leu Pro Gly Arg Met Phe Lys Val Ser Ser Leu Ala Val Leu Ala
1               5                   10                  15

Asp Glu Arg Arg Phe Ser Ala
                20
```

( 2 ) INFORMATION FOR SEQ ID NO:52:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: 28 4 0.1

( x i ) SEQUENCE DESCRIPTION: SEQ ID NO:52:

```
Val Gly Ser Phe Lys Arg Thr Phe Lys Val Ser Cys
1               5                   10
```

( 2 ) INFORMATION FOR SEQ ID NO:53:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: 29 4 0.1

( x i ) SEQUENCE DESCRIPTION: SEQ ID NO:53:

```
Arg Gly Arg Met Phe Lys Val Ser Ser Leu Ala Val Leu Ala Asp Glu
1               5                   10                  15

Arg Arg Phe Ser Ala
                20
```

( 2 ) INFORMATION FOR SEQ ID NO:54:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: 54 3 0.1

( x i ) SEQUENCE DESCRIPTION: SEQ ID NO:54:

```
Pro Gly Arg Trp Val Arg Gly Val Gly Ile Arg Cys Phe Lys Val Ser
1               5                   10                  15

Ser Leu Ala Val Leu Ala Asp Glu Arg Arg Phe Ser Ala
                20                  25
```

( 2 ) INFORMATION FOR SEQ ID NO:55:

( i ) SEQUENCE CHARACTERISTICS:
        ( A ) LENGTH: 22 amino acids
        ( B ) TYPE: amino acid
        ( C ) STRANDEDNESS: single
        ( D ) TOPOLOGY: linear ( i i ) MOLECULE TYPE: peptide (v i i) IMMEDIATE SOURCE:
 (B) CLONE: 60 2 0.1

(x i) SEQUENCE DESCRIPTION: SEQ ID NO:55:

Arg Met Ser Arg Leu Phe Lys Val Ser Ser Leu Ala Val Leu Ala Asp
1               5                   10                  15

Glu Arg Arg Phe Ser Ala
            20

(2) INFORMATION FOR SEQ ID NO:56:

(i) SEQUENCE CHARACTERISTICS:
  (A) LENGTH: 28 amino acids
  (B) TYPE: amino acid
  (C) STRANDEDNESS: single
  (D) TOPOLOGY: linear (i i) MOLECULE TYPE: peptide (v i i) IMMEDIATE SOURCE:
  (B) CLONE: 1 4 0.1

(x i) SEQUENCE DESCRIPTION: SEQ ID NO:56:

Pro Asp Val Leu Arg Ala Val Ala Thr Arg Gln His Lys Val Ser Ser
1               5                   10                  15

Leu Ala Val Leu Ala Asp Glu Arg Arg Phe Ser Ala
            20                  25

(2) INFORMATION FOR SEQ ID NO:57:

(i) SEQUENCE CHARACTERISTICS:
  (A) LENGTH: 12 amino acids
  (B) TYPE: amino acid
  (C) STRANDEDNESS: single
  (D) TOPOLOGY: linear (i i) MOLECULE TYPE: peptide (v i i) IMMEDIATE SOURCE:
  (B) CLONE: 27 4 0.2

(x i) SEQUENCE DESCRIPTION: SEQ ID NO:57:

Arg Val Arg Gly His Arg Val Val Met Tyr Asn Glu
1               5                   10

(2) INFORMATION FOR SEQ ID NO:58:

(i) SEQUENCE CHARACTERISTICS:
  (A) LENGTH: 12 amino acids
  (B) TYPE: amino acid
  (C) STRANDEDNESS: single
  (D) TOPOLOGY: linear (i i) MOLECULE TYPE: peptide (v i i) IMMEDIATE SOURCE:
  (B) CLONE: 64 2 0.1

(x i) SEQUENCE DESCRIPTION: SEQ ID NO:58:

Glu Cys Leu His Arg Arg Val His Lys Ile Leu Ser
1               5                   10

(2) INFORMATION FOR SEQ ID NO:59:

(i) SEQUENCE CHARACTERISTICS:
  (A) LENGTH: 12 amino acids
  (B) TYPE: amino acid
  (C) STRANDEDNESS: single
  (D) TOPOLOGY: linear ( i i ) MOLECULE TYPE: peptide ( v i i ) IMMEDIATE SOURCE:
    ( B ) CLONE: 61 2 0.1

( x i ) SEQUENCE DESCRIPTION: SEQ ID NO:59:

Gly Leu Lys Cys Arg Pro Met Lys Val Asn Ala Asp
1                    5                            10

( 2 ) INFORMATION FOR SEQ ID NO:60:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: 50 3 0.1

( x i ) SEQUENCE DESCRIPTION: SEQ ID NO:60:

Arg His Arg Pro Phe Gly Trp Val Asn Lys Arg Ser
1                    5                            10

( 2 ) INFORMATION FOR SEQ ID NO:61:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: 52 3 0.2

( x i ) SEQUENCE DESCRIPTION: SEQ ID NO:61:

Ala Ala Arg Leu Phe Ser Gln Ile Arg Arg Phe Pro
1                    5                            10

( 2 ) INFORMATION FOR SEQ ID NO:62:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: 53 3 0.1

( x i ) SEQUENCE DESCRIPTION: SEQ ID NO:62:

Arg Val Arg Trp His Met Val Thr Gly Asp Lys Gly
1                    5                            10

( 2 ) INFORMATION FOR SEQ ID NO:63:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( v i i ) IMMEDIATE SOURCE:
        ( B ) CLONE: 31 4 0.1

( x i ) SEQUENCE DESCRIPTION: SEQ ID NO:63:

Arg Phe Arg Asn Cys Ser Ile Ile Ser Ala Arg Gly
1               5                   10

( 2 ) INFORMATION FOR SEQ ID NO:64:

( i ) SEQUENCE CHARACTERISTICS:
           ( A ) LENGTH: 12 amino acids
           ( B ) TYPE: amino acid
           ( C ) STRANDEDNESS: single
           ( D ) TOPOLOGY: linear ( i i ) MOLECULE TYPE: peptide ( v i i ) IMMEDIATE SOURCE:
           ( B ) CLONE: 62 2 0.1

( x i ) SEQUENCE DESCRIPTION: SEQ ID NO:64:

Tyr Gly Val Pro Arg Ile val Ala His Gln Leu Met
1               5                   10

( 2 ) INFORMATION FOR SEQ ID NO:65:

( i ) SEQUENCE CHARACTERISTICS:
           ( A ) LENGTH: 5 amino acids
           ( B ) TYPE: amino acid
           ( C ) STRANDEDNESS: single
           ( D ) TOPOLOGY: linear ( i i ) MOLECULE TYPE: peptide ( x i ) SEQUENCE DESCRIPTION: SEQ ID NO:65:

Gly Ala Asp Gly Ala
1               5

( 2 ) INFORMATION FOR SEQ ID NO:66:

( i ) SEQUENCE CHARACTERISTICS:
           ( A ) LENGTH: 7 amino acids
           ( B ) TYPE: amino acid
           ( C ) STRANDEDNESS: single
           ( D ) TOPOLOGY: linear ( i i ) MOLECULE TYPE: peptide ( x i ) SEQUENCE DESCRIPTION: SEQ ID NO:66:

Arg Gln Phe Lys Val Val Thr
1               5

( 2 ) INFORMATION FOR SEQ ID NO:67:

( i ) SEQUENCE CHARACTERISTICS:
           ( A ) LENGTH: 4 amino acids
           ( B ) TYPE: amino acid
           ( C ) STRANDEDNESS: single
           ( D ) TOPOLOGY: linear ( i i ) MOLECULE TYPE: peptide ( x i ) SEQUENCE DESCRIPTION: SEQ ID NO:67:

Gly Lys Arg Xaa
1

( 2 ) INFORMATION FOR SEQ ID NO:68:

( i ) SEQUENCE CHARACTERISTICS:
           ( A ) LENGTH: 53 base pairs
           ( B ) TYPE: nucleic acid
           ( C ) STRANDEDNESS: single ( D ) TOPOLOGY: linear ( i i ) MOLECULE TYPE: DNA ( x i ) SEQUENCE DESCRIPTION: SEQ ID NO:68:

GCGGGCTAGC TAACTAATGG AGGATACATA AATGAAACCA GTAACGTTAT ACG        53

( 2 ) INFORMATION FOR SEQ ID NO:69:

( i ) SEQUENCE CHARACTERISTICS:
                ( A ) LENGTH: 46 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:69:

CGTTCCGAGC TCACTGCCCG CTCTCGAGTC GGGAAACCTG TCGTGC        46

( 2 ) INFORMATION FOR SEQ ID NO:70:

( i ) SEQUENCE CHARACTERISTICS:
                ( A ) LENGTH: 51 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:70:

CCTCCATATG AATTGTGAGC GCTCACAATT CGGTACAGCC CCATCCCACC C        51

( 2 ) INFORMATION FOR SEQ ID NO:71:

( i ) SEQUENCE CHARACTERISTICS:
                ( A ) LENGTH: 51 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:71:

CGCCATCGAT CAATTGTGAG CGCTCACAAT TCAGGATGTG TGTGATGAAG A        51

( 2 ) INFORMATION FOR SEQ ID NO:72:

( i ) SEQUENCE CHARACTERISTICS:
                ( A ) LENGTH: 72 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:72:

TCGAGAGCGG GCAGGGGCC GACGGGCCT ACGGTGGTTT CCTGCGTCGT CAGTTCAAAG        60

TTGTAACCTA AT        72

( 2 ) INFORMATION FOR SEQ ID NO:73:

( i ) SEQUENCE CHARACTERISTICS:
                ( A ) LENGTH: 72 base pairs
                ( B ) TYPE: nucleic acid
                ( C ) STRANDEDNESS: single
                ( D ) TOPOLOGY: linear ( i i ) MOLECULE TYPE: DNA ( x i ) SEQUENCE DESCRIPTION: SEQ ID NO:73:

CTAGATTAGG TTACAACTTT GAACTGACGA CGCAGGAAAC CACCGTAGGC CCCGTCGGCC     60

CCCTGCCCGC TC     72

( 2 ) INFORMATION FOR SEQ ID NO:74:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:74:

GGGCCTAATT AATTA     15

( 2 ) INFORMATION FOR SEQ ID NO:75:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:75:

AGCTTAATTA ATTAGGCCCC GT     22

( 2 ) INFORMATION FOR SEQ ID NO:76:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:76:

GTGGCGCCNN KNNKNNKNNK NNKNNKNNKN NKNNKNNKNN KNNKTAAGGT CTCG     54

( 2 ) INFORMATION FOR SEQ ID NO:77:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:77:

GGCGCCACCG T     11

( 2 ) INFORMATION FOR SEQ ID NO:78:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:78:

AGCTCGAGAC CTTA                                                                                      14

( 2 ) INFORMATION FOR SEQ ID NO:79:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:79:

TATTTGCACG GCGTCACACT T                                                                              21

( 2 ) INFORMATION FOR SEQ ID NO:80:

( i ) SEQUENCE CHARACTERISTICS:
        ( A ) LENGTH: 47 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:80:

CCGCGCCTGG GCCCAGGGAA TGTAATTGAG CTCCGCCATC GCCGCTT                                                  47

( 2 ) INFORMATION FOR SEQ ID NO:81:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:81:

CGATGGCGGA GCTCAATTAC ATTCCCNNKN NKNNKNNKNN KAAACCAGTA ACGTTATACG                                    60

AT                                                                                                   62

( 2 ) INFORMATION FOR SEQ ID NO:82:

( i ) SEQUENCE CHARACTERISTICS:
        ( A ) LENGTH: 59 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:82:

CGATGGCGGA GCTCAATTAC ATTCCCNNKN NKNNKNNKAA ACCAGTAACG TTATACGAT                                     59

( 2 ) INFORMATION FOR SEQ ID NO:83:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:83:

CGCCCGCCAA GCTTAGGTTA CAACTTTGAA CTGACGMNNM NNMNNMNNGG GAATGTAATT                                    60

CAGCTCCGCC AT                                                                                        72

( 2 ) INFORMATION FOR SEQ ID NO:84:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:84:

GAATTCAATT GTGAGCGCTC ACAATTGAAT TC        32

( 2 ) INFORMATION FOR SEQ ID NO:85:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:85:

ACCACCTCCG G        11

( 2 ) INFORMATION FOR SEQ ID NO:86:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:86:

TTACTTAGTT A        11

( 2 ) INFORMATION FOR SEQ ID NO:87:

( i ) SEQUENCE CHARACTERISTICS:
        ( A ) LENGTH: 49 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:87:

```
Met Lys Pro Val Thr Leu Tyr Asp Val Ala Glu Tyr Ala Gly Val Ser
 1               5                  10                  15
Tyr Gln Thr Val Ser Arg Val Val Asn Gln Ala Ser His Val Ser Ala
                20                  25                  30
Lys Thr Arg Glu Lys Val Glu Ala Ala Met Ala Glu Leu Asn Tyr Ile
                35                  40                  45
Pro
```

( 2 ) INFORMATION FOR SEQ ID NO:88:

( i ) SEQUENCE CHARACTERISTICS:
        ( A ) LENGTH: 93 base pairs
        ( B ) TYPE: nucleic acid
        ( C ) STRANDEDNESS: double
        ( D ) TOPOLOGY: linear ( i i ) MOLECULE TYPE: DNA ( i x ) FEATURE:
  ( A ) NAME/KEY: CDS
  ( B ) LOCATION: 1..84

( x i ) SEQUENCE DESCRIPTION: SEQ ID NO:88:

```
CTC  GAG  AGC  GGG  CAG  GTG  GTG  CAT  GGG  GAG  CAG  GTG  GGT  GGT  GAG  GCC           48
Leu  Glu  Ser  Gly  Gln  Val  Val  His  Gly  Glu  Gln  Val  Gly  Gly  Glu  Ala
1                  5                       10                      15

TCC  GGG  GCC  GTT  AAC  GGC  CGT  GGC  CTA  GCT  GGC  CAA  TAAGTCGAC                    93
Ser  Gly  Ala  Val  Asn  Gly  Arg  Gly  Leu  Ala  Gly  Gln
                20                       25
```

( 2 ) INFORMATION FOR SEQ ID NO:89:

( i ) SEQUENCE CHARACTERISTICS:
    ( A ) LENGTH: 28 amino acids
    ( B ) TYPE: amino acid
    ( D ) TOPOLOGY: linear ( i i ) MOLECULE TYPE: protein ( x i ) SEQUENCE DESCRIPTION: SEQ ID NO:89:

```
Leu  Glu  Ser  Gly  Gln  Val  Val  His  Gly  Glu  Gln  Val  Gly  Gly  Glu  Ala
1                  5                       10                      15

Ser  Gly  Ala  Val  Asn  Gly  Arg  Gly  Leu  Ala  Gly  Gln
                20                       25
```

( 2 ) INFORMATION FOR SEQ ID NO:90:

( i ) SEQUENCE CHARACTERISTICS:
    ( A ) LENGTH: 90 base pairs
    ( B ) TYPE: nucleic acid
    ( C ) STRANDEDNESS: double
    ( D ) TOPOLOGY: linear ( i i ) MOLECULE TYPE: DNA ( i x ) FEATURE:
    ( A ) NAME/KEY: CDS
    ( B ) LOCATION: 1..60

( x i ) SEQUENCE DESCRIPTION: SEQ ID NO:90:

```
CTC  GAG  AGC  GGG  CAG  GTG  GTG  CAT  GGG  GAG  CAG  GTG  GGT  GGT  GAG  GCC           48
Leu  Glu  Ser  Gly  Gln  Val  Val  His  Gly  Glu  Gln  Val  Gly  Gly  Glu  Ala
1                  5                       10                      15

TCC  GGA  GGT  GGT  TAACTAAGTA  AAGCTGGCCA  ATAAGTCGAC                                   90
Ser  Gly  Gly  Gly
                20
```

( 2 ) INFORMATION FOR SEQ ID NO:91:

( i ) SEQUENCE CHARACTERISTICS:
    ( A ) LENGTH: 20 amino acids
    ( B ) TYPE: amino acid
    ( D ) TOPOLOGY: linear ( i i ) MOLECULE TYPE: protein ( x i ) SEQUENCE DESCRIPTION: SEQ ID NO:91:

```
Leu  Glu  Ser  Gly  Gln  Val  Val  His  Gly  Glu  Gln  Val  Gly  Gly  Glu  Ala
1                  5                       10                      15

Ser  Gly  Gly  Gly
                20
```

( 2 ) INFORMATION FOR SEQ ID NO:92:

( i ) SEQUENCE CHARACTERISTICS:

( A ) LENGTH: 48 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:92:

Lys Pro Val Thr Leu Tyr Asp Val Ala Glu Tyr Ala Gly Val Ser Tyr
1               5                   10                  15

Gln Thr Val Ser Arg Val Val Asn Gln Ala Ser His Val Ser Ala Lys
                20                  25                  30

Thr Arg Glu Lys Val Glu Ala Ala Met Ala Glu Leu Asn Tyr Ile Pro
            35                  40                  45

( 2 ) INFORMATION FOR SEQ ID NO:93:

( i ) SEQUENCE CHARACTERISTICS:
( A ) LENGTH: 45 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:93:

Arg Thr Ser Asn Val Ile Arg Cys Arg Arg Val Cys Arg Cys Leu Leu
1               5                   10                  15

Ser Asp Arg Phe Pro Arg Gly Glu Pro Gly Gln Pro Arg Phe Cys Glu
                20                  25                  30

Asn Ala Gly Lys Ser Gly Ser Gly Asp Gly Gly Ala Asp
            35                  40

( 2 ) INFORMATION FOR SEQ ID NO:94:

( i ) SEQUENCE CHARACTERISTICS:
( A ) LENGTH: 41 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:94:

Leu Ser Asn Val Ile Arg Cys Arg Arg Val Cys Arg Cys Leu Leu Ser
1               5                   10                  15

Asp Arg Phe Pro Arg Gly Glu Pro Gly Gln Pro Arg Phe Cys Glu Asn
                20                  25                  30

Ala Gly Lys Ser Gly Ser Gly Asp Gly
            35                  40

( 2 ) INFORMATION FOR SEQ ID NO:95:

( i ) SEQUENCE CHARACTERISTICS:
( A ) LENGTH: 35 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:95:

Val Ser Tyr Arg Thr Val Ser Arg Val Val Asn Gln Ala Gly His Val
1               5                   10                  15

Pro Ala Lys Thr Arg Glu Lys Val Val Ala Ala Met Ala Glu Leu Asn
                20                  25                  30

Tyr Ile Pro
          35

( 2 ) INFORMATION FOR SEQ ID NO:96:

( i ) SEQUENCE CHARACTERISTICS:
        ( A ) LENGTH: 43 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:96:

Lys Pro Val Thr Leu Tyr Asp Val Ala Glu Tyr Ala Gly Val Ser Tyr
 1               5                  10                 15

Arg Thr Val Ser Arg Val Val Asn Gln Ala Ser His Val Ser Ala Lys
             20                  25                 30

Thr Arg Glu Lys Val Glu Ala Ala Thr Ala Glu
         35                  40

( 2 ) INFORMATION FOR SEQ ID NO:97:

( i ) SEQUENCE CHARACTERISTICS:
        ( A ) LENGTH: 49 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:97:

Met Lys Pro Val Thr Leu Tyr Asp Val Ala Glu Tyr Ala Gly Val Ser
 1               5                  10                 15

Tyr Arg Thr Val Ser Arg Val Val Asn Gln Ala Ser His Val Ser Ala
             20                  25                 30

Lys Thr Arg Glu Lys Val Glu Ala Ala Met Ala Glu Leu Asn Tyr Ile
         35                  40                 45

Pro ( 2 ) INFORMATION FOR SEQ ID NO:98:

( i ) SEQUENCE CHARACTERISTICS:
        ( A ) LENGTH: 48 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:98:

Lys Pro Val Thr Leu Tyr Asp Val Ala Glu Tyr Ala Gly Val Ser Tyr
 1               5                  10                 15

Gln Thr Val Ser Arg Val Val Asn Gln Ala Ser His Val Ser Ala Lys
             20                  25                 30

Thr Gly Glu Glu Val Glu Ala Ala Met Ala Gly Leu Asn Tyr Ile Pro
         35                  40                 45

( 2 ) INFORMATION FOR SEQ ID NO:99:

( i ) SEQUENCE CHARACTERISTICS:
        ( A ) LENGTH: 49 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:99:

```
Met  Lys  Pro  Val  Thr  Leu  Tyr  Asp  Val  Ala  Glu  Tyr  Ala  Gly  Thr  Ser
1                   5                        10                       15
Tyr  Gln  Thr  Pro  Ser  Arg  Val  Val  Asn  Gln  Ala  Ser  His  Val  Ser  Ala
                20                       25                       30
Lys  Thr  Arg  Glu  Lys  Val  Glu  Ala  Ala  Met  Ala  Glu  Leu  Asn  Tyr  Ile
              35                       40                       45
Pro
```

( 2 ) INFORMATION FOR SEQ ID NO:100:

( i ) SEQUENCE CHARACTERISTICS:
        ( A ) LENGTH: 48 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:100:

```
Lys  Pro  Val  Thr  Leu  Tyr  Asp  Val  Ala  Glu  Tyr  Ala  Gly  Val  Ser  Tyr
1                   5                        10                       15
Arg  Thr  Val  Ser  Arg  Val  Val  Asn  Gln  Ala  Ser  Leu  Val  Ser  Ala  Lys
                20                       25                       30
Thr  Arg  Glu  Lys  Glu  Glu  Ala  Ala  Met  Ala  Glu  Leu  Asn  Tyr  Ile  Pro
              35                       40                       45
```

( 2 ) INFORMATION FOR SEQ ID NO:101:

( i ) SEQUENCE CHARACTERISTICS:
        ( A ) LENGTH: 48 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:101:

```
Lys  Pro  Val  Thr  Leu  Tyr  Asp  Val  Ala  Glu  Tyr  Ala  Gly  Val  Ser  Tyr
1                   5                        10                       15
Arg  Thr  Val  Ser  Arg  Val  Val  Asn  Gln  Ala  Ser  His  Val  Ser  Ala  Lys
                20                       25                       30
Thr  Arg  Glu  Lys  Val  Glu  Ala  Ala  Met  Ala  Glu  Leu  Asn  Tyr  Ile  Pro
              35                       40                       45
```

( 2 ) INFORMATION FOR SEQ ID NO:102:

( i ) SEQUENCE CHARACTERISTICS:
        ( A ) LENGTH: 49 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:102:

```
Met  Lys  Pro  Val  Thr  Leu  Tyr  Asp  Val  Ala  Glu  Tyr  Ala  Gly  Val  Ser
1                   5                        10                       15
Tyr  Gln  Thr  Asp  Ser  Arg  Val  Glu  Asn  Gln  Ala  Ser  His  Val  Ser  Ala
                20                       25                       30
Lys  Thr  Arg  Glu  Lys  Val  Glu  Ala  Ala  Met  Ala  Glu  Leu  Asn  Tyr  Ile
```

(2) INFORMATION FOR SEQ ID NO:103:

(i) SEQUENCE CHARACTERISTICS:
        (A) LENGTH: 49 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:103:

```
Met Lys Met Val Thr Leu Tyr Asp Val Ala Glu Tyr Ala Gly Val Ser
  1               5                  10                  15
Tyr Gln Thr Val Ser Arg Val Val Asn Gln Ala Ser His Val Ser Ala
             20                  25                  30
Lys Thr Arg Glu Lys Val Glu Ala Ala Met Ala Glu Leu Asn Tyr Ile
         35                  40                  45
Pro
```

(2) INFORMATION FOR SEQ ID NO:104:

(i) SEQUENCE CHARACTERISTICS:
        (A) LENGTH: 48 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:104:

```
Lys Pro Val Thr Leu Tyr Asp Val Ala Glu Tyr Ala Gly Val Ser Tyr
  1               5                  10                  15
Arg Thr Val Ser Arg Val Val Asn Gln Ala Ser His Ala Ser Ala Lys
             20                  25                  30
Thr Arg Glu Lys Val Glu Ala Ala Met Thr Glu Leu Asn Tyr Ile Pro
         35                  40                  45
```

(2) INFORMATION FOR SEQ ID NO:105:

(i) SEQUENCE CHARACTERISTICS:
        (A) LENGTH: 49 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:105:

```
Met Lys Pro Val Thr Leu Tyr Asp Val Ala Glu Tyr Ala Gly Ala Ser
  1               5                  10                  15
Tyr Gln Thr Val Ser Arg Val Val Asn Gln Ala Ser His Val Ser Ala
             20                  25                  30
Lys Thr Arg Glu Lys Val Glu Ala Ala Met Ala Glu Leu Asn Tyr Val
         35                  40                  45
Pro
```

(2) INFORMATION FOR SEQ ID NO:106:

(i) SEQUENCE CHARACTERISTICS:
        (A) LENGTH: 48 amino acids
        (B) TYPE: amino acid ( C ) STRANDEDNESS: single
( D ) TOPOLOGY: linear ( i i ) MOLECULE TYPE: peptide ( x i ) SEQUENCE DESCRIPTION: SEQ ID NO:106:

| Lys | Pro | Val | Thr | Leu | Tyr | Asp | Val | Ala | Glu | Tyr | Ala | Gly | Val | Ser | Tyr |
|---|---|---|---|---|---|---|---|---|---|---|---|---|---|---|---|
| 1 | | | | 5 | | | | | 10 | | | | | 15 | |
| Gln | Thr | Val | Ser | Arg | Val | Val | Asn | Gln | Ala | Ser | His | Val | Ser | Ala | Lys |
| | | | 20 | | | | | 25 | | | | | 30 | | |
| Thr | Arg | Glu | Lys | Val | Gly | Ala | Ala | Met | Ala | Glu | Leu | Asn | Tyr | Ile | Pro |
| | | 35 | | | | | 40 | | | | | 45 | | | |

( 2 ) INFORMATION FOR SEQ ID NO:107:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:107:

Xaa Xaa Xaa Xaa Xaa
1                   5

( 2 ) INFORMATION FOR SEQ ID NO:108:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:108:

Xaa Xaa Xaa Xaa
1

( 2 ) INFORMATION FOR SEQ ID NO:109:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:109:

Gly Arg Cys Arg
1

( 2 ) INFORMATION FOR SEQ ID NO:110:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:110:

Gly Pro Asn Gln Arg Gln Phe Lys Val Val Thr
1               5                   10

( 2 ) INFORMATION FOR SEQ ID NO:111:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:111:

```
Val Tyr Cys Arg
1
```

( 2 ) INFORMATION FOR SEQ ID NO:112:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:112:

```
Asp His Pro Val Arg Gln Phe Lys Val Val Thr
1               5                   10
```

( 2 ) INFORMATION FOR SEQ ID NO:113:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:113:

```
Thr Val Val Leu
1
```

( 2 ) INFORMATION FOR SEQ ID NO:114:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:114:

```
Arg Arg Tyr Pro Arg Gln Phe Lys Val Val Thr
1               5                   10
```

( 2 ) INFORMATION FOR SEQ ID NO:115:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:115:

```
Lys Met Cys Met
1
```

( 2 ) INFORMATION FOR SEQ ID NO:116:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:116:

```
Pro Ala Gln Ser Arg Gln Phe Lys Val Val Thr
 1               5                   10
```

( 2 ) INFORMATION FOR SEQ ID NO:117:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:117:

```
Leu Arg Arg Cys
 1
```

( 2 ) INFORMATION FOR SEQ ID NO:118:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:118:

```
Leu Ser Lys Arg Arg Gln Phe Lys Val Val Thr
 1               5                   10
```

( 2 ) INFORMATION FOR SEQ ID NO:119:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:119:

```
Arg Ser Gln Glu Arg Gln Phe Lys Val Val Thr
 1               5                   10
```

( 2 ) INFORMATION FOR SEQ ID NO:120:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:120:

```
Ser Cys Val Pro
 1
```

( 2 ) INFORMATION FOR SEQ ID NO:121:

( i ) SEQUENCE CHARACTERISTICS:
         ( A ) LENGTH: 11 amino acids
         ( B ) TYPE: amino acid
         ( C ) STRANDEDNESS: single
         ( D ) TOPOLOGY: linear ( i i ) MOLECULE TYPE: peptide ( x i ) SEQUENCE DESCRIPTION: SEQ ID NO:121:

```
Lys Arg Arg Val Arg Gln Phe Lys Val Val Thr
 1           5                   10
```

( 2 ) INFORMATION FOR SEQ ID NO:122:

( i ) SEQUENCE CHARACTERISTICS:
         ( A ) LENGTH: 11 amino acids
         ( B ) TYPE: amino acid
         ( C ) STRANDEDNESS: single
         ( D ) TOPOLOGY: linear ( i i ) MOLECULE TYPE: peptide ( x i ) SEQUENCE DESCRIPTION: SEQ ID NO:122:

```
Glu His Ala Arg Arg Gln Phe Lys Val Val Thr
 1           5                   10
```

( 2 ) INFORMATION FOR SEQ ID NO:123:

( i ) SEQUENCE CHARACTERISTICS:
         ( A ) LENGTH: 94 base pairs
         ( B ) TYPE: nucleic acid
         ( C ) STRANDEDNESS: double
         ( D ) TOPOLOGY: linear ( i i ) MOLECULE TYPE: DNA ( i x ) FEATURE:
         ( A ) NAME/KEY: CDS
         ( B ) LOCATION: 1..84

( x i ) SEQUENCE DESCRIPTION: SEQ ID NO:123:

```
GAA GCG GCG ATG GCG GAG CTG AAT TAC ATT CCC CGG TCG CAG GAG GCC      48
Glu Ala Ala Met Ala Glu Leu Asn Tyr Ile Pro Arg Ser Gln Glu Ala
 1               5                   10                  15

TCC GGG GCC GTT AAC GGC CGT GGC CTA GCT GGC CAA TAAGGTCGAC           94
Ser Gly Ala Val Asn Gly Arg Gly Leu Ala Gly Gln
             20                  25
```

( 2 ) INFORMATION FOR SEQ ID NO:124:

( i ) SEQUENCE CHARACTERISTICS:
         ( A ) LENGTH: 28 amino acids
         ( B ) TYPE: amino acid
         ( D ) TOPOLOGY: linear ( i i ) MOLECULE TYPE: protein ( x i ) SEQUENCE DESCRIPTION: SEQ ID NO:124:

```
Glu Ala Ala Met Ala Glu Leu Asn Tyr Ile Pro Arg Ser Gln Glu Ala
 1               5                   10                  15

Ser Gly Ala Val Asn Gly Arg Gly Leu Ala Gly Gln
             20                  25
```

( 2 ) INFORMATION FOR SEQ ID NO:125:

( i ) SEQUENCE CHARACTERISTICS:
         ( A ) LENGTH: 122 base pairs ( B ) TYPE: nucleic acid
( C ) STRANDEDNESS: double
( D ) TOPOLOGY: linear ( i i ) MOLECULE TYPE: DNA ( x i ) SEQUENCE DESCRIPTION: SEQ ID NO:125:

```
GAAGCGGCGA TGGCGGAGCT GAATTACATT CCCCGGTCGC AGGAGGCCTC CGGAGGTGGT      60
NNKNNKNNKN NKNNKNNKNN KNNKNNKNNK NNKNNKTAAC TAAGTAAAGC TGGCCAATAA     120
GT                                                                   122
```

( 2 ) INFORMATION FOR SEQ ID NO:126:

( i ) SEQUENCE CHARACTERISTICS:
( A ) LENGTH: 32 amino acids
( B ) TYPE: amino acid
( D ) TOPOLOGY: linear ( i i ) MOLECULE TYPE: protein ( x i ) SEQUENCE DESCRIPTION: SEQ ID NO:126:

```
Glu Ala Ala Met Ala Glu Leu Asn Tyr Ile Pro Arg Ser Gln Glu Ala
 1               5                  10                  15
Ser Gly Gly Gly Xaa Xaa Xaa Xaa Xaa Xaa Xaa Xaa Xaa Xaa Xaa Xaa
            20                  25                  30
```

( 2 ) INFORMATION FOR SEQ ID NO:127:

( i ) SEQUENCE CHARACTERISTICS:
( A ) LENGTH: 8 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:127:

```
Lys Gln Phe Lys Val Thr Lys Thr
 1               5
```

( 2 ) INFORMATION FOR SEQ ID NO:128:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:128:

```
Phe His Val Thr Gly Lys Ala Trp Cys Pro Leu Arg
 1               5                  10
```

( 2 ) INFORMATION FOR SEQ ID NO:129:

( i ) SEQUENCE CHARACTERISTICS:
( A ) LENGTH: 12 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:129:

```
Thr Phe Lys Val Val Pro Gln Met Glu Gly Met Thr
 1               5                  10
```

( 2 ) INFORMATION FOR SEQ ID NO:130:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:130:

```
Glu Val Gln Ile Arg Ser Phe Arg Val Gly Lys Val
1               5                   10
```

( 2 ) INFORMATION FOR SEQ ID NO:131:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:131:

```
Tyr Leu Ser Thr Glu Arg Pro Arg Arg Met Phe His Leu Thr Lys
1               5                   10                  15
```

( 2 ) INFORMATION FOR SEQ ID NO:132:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:132:

```
Val Arg Met His Lys Val Ser Glu Gln Ser Arg Phe
1               5                   10
```

( 2 ) INFORMATION FOR SEQ ID NO:133:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:133:

```
His Ser Arg Ala Phe Arg Ala Thr Lys Ser Val Val
1               5                   10
```

( 2 ) INFORMATION FOR SEQ ID NO:134:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:134:

```
Arg His His Met Phe Ser Val Thr Arg Ile Trp Asp
1               5                   10
```

( 2 ) INFORMATION FOR SEQ ID NO:135:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:135:

```
Ala Phe Ala Val Thr His Lys Arg Asn Arg Gly Tyr
1               5                   10
```

( 2 ) INFORMATION FOR SEQ ID NO:136:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:136:

```
Arg Ser Leu Ala Gly Arg Arg Phe Arg Ile Leu Gly Asn
1               5                   10
```

( 2 ) INFORMATION FOR SEQ ID NO:137:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:137:

```
Ile Glu His Pro Tyr Arg Ile Asp Arg Met Val Met
1               5                   10
```

( 2 ) INFORMATION FOR SEQ ID NO:138:

( i ) SEQUENCE CHARACTERISTICS:
        ( A ) LENGTH: 14 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:138:

```
His Arg Ser Leu Pro Ser Thr Arg Arg Phe Arg Leu Thr Lys
1               5                   10
```

( 2 ) INFORMATION FOR SEQ ID NO:139:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:139:

```
Phe Ser Val Val Arg Gly Cys Arg Ile Phe Arg Ile Asn
1               5                   10
```

( 2 ) INFORMATION FOR SEQ ID NO:140:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:140:

```
Gln Phe Arg Val Val Thr Leu Thr Ser Pro Leu Ala
 1               5                  10
```

( 2 ) INFORMATION FOR SEQ ID NO:141:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:141:

```
Leu Ala Arg Pro Phe Arg Arg Ala Lys Leu Asp Gly
 1               5                  10
```

( 2 ) INFORMATION FOR SEQ ID NO:142:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:142:

```
Leu Leu Arg Arg Pro Phe Met Val Asn Arg Asn Thr
 1               5                  10
```

( 2 ) INFORMATION FOR SEQ ID NO:143:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:143:

```
His Arg Tyr Asn Arg Thr Val Gly Ile Asn Glu Val
 1               5                  10
```

( 2 ) INFORMATION FOR SEQ ID NO:144:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:144:

```
Arg Arg Arg Arg Asn Cys Gln Ile Val Gly Tyr Trp
 1               5                  10
```

( 2 ) INFORMATION FOR SEQ ID NO:145:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:145:

```
Arg Gly Leu Met Arg Arg Ser Tyr Lys Thr Val
1               5                   10
```

( 2 ) INFORMATION FOR SEQ ID NO:146:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:146:

```
Met Gly Gly Arg Arg Val Arg Leu Ala Arg Ile Ile Asn
1               5                   10
```

( 2 ) INFORMATION FOR SEQ ID NO:147:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:147:

```
Ser Gly Arg Pro Phe Arg Met Glu Arg Gln Arg Pro
1               5                   10
```

( 2 ) INFORMATION FOR SEQ ID NO:148:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Region
    ( B ) LOCATION: 5
    ( D ) OTHER INFORMATION: /note="Xaa is unknown."

( x i ) SEQUENCE DESCRIPTION: SEQ ID NO:148:

```
Lys Met Val Arg Xaa Ile Phe Arg Thr Ile Pro Gly
1               5                   10
```

( 2 ) INFORMATION FOR SEQ ID NO:149:

( i ) SEQUENCE CHARACTERISTICS:
    ( A ) LENGTH: 9 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:149:

Leu Arg Arg Met Arg Val Val Ile Arg
1               5

( 2 ) INFORMATION FOR SEQ ID NO:150:

( i ) SEQUENCE CHARACTERISTICS:
       ( A ) LENGTH: 13 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:150:

Lys Trp Ser Gly Leu Gly Gly Gly Arg Val Leu Val Asn
1               5                   10

( 2 ) INFORMATION FOR SEQ ID NO:151:

( i ) SEQUENCE CHARACTERISTICS:
       ( A ) LENGTH: 12 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:151:

Arg Arg Trp Ala Thr Ser Gly Pro Arg Gln Leu Tyr
1               5                   10

( 2 ) INFORMATION FOR SEQ ID NO:152:

( i ) SEQUENCE CHARACTERISTICS:
       ( A ) LENGTH: 13 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:152:

Glu Pro Lys Phe Lys Asn Phe Arg Val Val Phe Gln Asn
1               5                   10

( 2 ) INFORMATION FOR SEQ ID NO:153:

( i ) SEQUENCE CHARACTERISTICS:
       ( A ) LENGTH: 13 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:153:

Arg Trp Phe Ser Pro Gly Arg Arg Ala Phe Met Val Asn
1               5                   10

( 2 ) INFORMATION FOR SEQ ID NO:154:

( i ) SEQUENCE CHARACTERISTICS:
       ( A ) LENGTH: 12 amino acids
       ( B ) TYPE: amino acid
       ( C ) STRANDEDNESS: single
       ( D ) TOPOLOGY: linear ( i i ) MOLECULE TYPE: peptide ( x i ) SEQUENCE DESCRIPTION: SEQ ID NO:154:

Gly Arg Pro Phe Arg Gln Asn Ser Pro Val Val Phe
1               5                       10

( 2 ) INFORMATION FOR SEQ ID NO:155:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:155:

Trp Val Pro Arg Met Gly Arg His Leu Ser Thr Leu
1               5                       10

( 2 ) INFORMATION FOR SEQ ID NO:156:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:156:

Arg Thr Arg His Val Phe Lys Val Ile His Gly Phe
1               5                       10

( 2 ) INFORMATION FOR SEQ ID NO:157:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:157:

Asn Ala Arg Arg Met Tyr Ser Val Ala Gly Met Asp
1               5                       10

( 2 ) INFORMATION FOR SEQ ID NO:158:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:158:

Trp Arg Lys Phe Ala Leu Leu Gly Ser Gly Pro Thr
1               5                       10

( 2 ) INFORMATION FOR SEQ ID NO:159:

( i ) SEQUENCE CHARACTERISTICS:
      ( A ) LENGTH: 12 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:159:

His Arg Ala Tyr Arg Ile Ala Thr Met Phe Ser Gly
1               5                       10

( 2 ) INFORMATION FOR SEQ ID NO:160:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:160:

Arg Gly Leu Met Arg Arg Ser Thr Lys Thr Val
1               5                   10

( 2 ) INFORMATION FOR SEQ ID NO:161:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:161:

Ala Arg His Arg Met Phe Gln Trp Ala Met Val Gly
1               5                       10

( 2 ) INFORMATION FOR SEQ ID NO:162:

( i ) SEQUENCE CHARACTERISTICS:
    ( A ) LENGTH: 12 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:162:

Ile Met Ile Gly Lys Glu Gly Ala Val Ser Ser Ser
1               5                       10